US008933282B2

(12) United States Patent
McAuliffe

(10) Patent No.: US 8,933,282 B2
(45) Date of Patent: Jan. 13, 2015

(54) FUEL COMPOSITIONS COMPRISING ISOPRENE DERIVATIVES

(75) Inventor: Joseph C. McAuliffe, Sunnyvale, CA (US)

(73) Assignee: Danisco US Inc., Palo Alto, CA (US)

( * ) Notice: Subject to any disclaimer, the term of this patent is extended or adjusted under 35 U.S.C. 154(b) by 855 days.

(21) Appl. No.: 13/163,601

(22) Filed: Jun. 17, 2011

(65) Prior Publication Data

US 2012/0157725 A1 Jun. 21, 2012

Related U.S. Application Data

(60) Provisional application No. 61/356,017, filed on Jun. 17, 2010, provisional application No. 61/426,481, filed on Dec. 22, 2010.

(51) Int. Cl.
| | |
|---|---|
| C07C 1/00 | (2006.01) |
| C12P 5/02 | (2006.01) |
| B01J 31/00 | (2006.01) |
| B01J 31/10 | (2006.01) |
| B01J 31/22 | (2006.01) |
| C10G 29/20 | (2006.01) |

(Continued)

(52) U.S. Cl.
CPC ............... *C12P 5/026* (2013.01); *B01J 31/003* (2013.01); *B01J 31/10* (2013.01); *B01J 31/2273* (2013.01); *B01J 31/2278* (2013.01); *C10G 29/205* (2013.01); *C10G 45/00* (2013.01); *C10G 45/32* (2013.01); *C10G 45/34* (2013.01); *C10G 45/58* (2013.01); *C10G 45/60* (2013.01); *C10G 65/043* (2013.01); *C10G 65/06* (2013.01); *C10G 69/123* (2013.01); *C12P 5/02* (2013.01); *C10L 1/04* (2013.01); *B01J 23/38* (2013.01); *B01J 23/70* (2013.01); *B01J 2231/543* (2013.01); *B01J 2531/821* (2013.01); *C10G 2400/22* (2013.01); *C10G 2300/1011* (2013.01); *Y02E 50/343* (2013.01); *C10G 2300/1081* (2013.01); *C10G 2400/20* (2013.01); *C10G 2300/807* (2013.01)
USPC .............. 585/240; 585/242; 585/615; 44/605

(58) Field of Classification Search
USPC ............................ 585/240, 242, 615; 44/605
See application file for complete search history.

(56) References Cited

U.S. PATENT DOCUMENTS

| | | |
|---|---|---|
| 3,185,739 A | 5/1965 | Gray et al. |
| 3,418,386 A | 12/1968 | Hayes |

(Continued)

FOREIGN PATENT DOCUMENTS

| | | |
|---|---|---|
| EP | 0 215 594 A2 | 3/1987 |
| EP | 0 215 594 A3 | 3/1987 |

(Continued)

OTHER PUBLICATIONS

Adams, J. et al. (1986). "Reactions of The Conjugated Dienes Butadiene and Isoprene Alone and With Methanol Over Ion-Exchanged Montmorillonites," *Clays and Clay Minerals* 34(3):287-294.

(Continued)

*Primary Examiner* — Nina Bhat
(74) *Attorney, Agent, or Firm* — Morrison & Foerster LLP

(57) ABSTRACT

Methods, compositions and systems using isoprene from a bioisoprene composition derived from renewable carbon for production of a variety of hydrocarbon fuels, fuel additives, and additives for fine chemistry and other uses is described.

17 Claims, 20 Drawing Sheets

(51) Int. Cl.

| | |
|---|---|
| *C10G 45/00* | (2006.01) |
| *C10G 45/32* | (2006.01) |
| *C10G 45/34* | (2006.01) |
| *C10G 45/58* | (2006.01) |
| *C10G 45/60* | (2006.01) |
| *C10G 65/04* | (2006.01) |
| *C10G 65/06* | (2006.01) |
| *C10G 69/12* | (2006.01) |
| *C10L 1/04* | (2006.01) |
| *B01J 23/38* | (2006.01) |
| *B01J 23/70* | (2006.01) |

(56) References Cited

U.S. PATENT DOCUMENTS

| | | |
|---|---|---|
| 3,689,585 A | 9/1972 | Morikawa |
| 3,917,730 A | 11/1975 | Tkatchenko |
| 3,932,550 A | 1/1976 | Morikawa et al. |
| 3,954,665 A | 5/1976 | Tkatchenko |
| 4,144,278 A | 3/1979 | Strope |
| 4,166,076 A | 8/1979 | Roobeek et al. |
| 4,181,707 A | 1/1980 | Strope |
| 4,189,403 A | 2/1980 | Roobeek et al. |
| 4,283,305 A | 8/1981 | Chauvin et al. |
| 4,507,516 A | 3/1985 | Hirooka et al. |
| 4,570,029 A | 2/1986 | Kulprathipanja et al. |
| 4,593,140 A | 6/1986 | Mortreux et al. |
| 4,652,527 A | 3/1987 | Stirling |
| 4,683,202 A | 7/1987 | Mullis |
| 4,703,007 A | 10/1987 | Mulholland et al. |
| 4,740,222 A | 4/1988 | Mehra |
| 4,818,250 A | 4/1989 | Whitworth |
| 4,973,787 A | 11/1990 | Colvin |
| 5,329,057 A | 7/1994 | Diesen et al. |
| 5,446,102 A | 8/1995 | Oziomek et al. |
| 5,476,956 A | 12/1995 | Hillion et al. |
| 5,545,789 A | 8/1996 | Duisters et al. |
| 5,575,822 A | 11/1996 | Wilkins, Jr. |
| 5,849,970 A | 12/1998 | Fall et al. |
| 5,874,276 A | 2/1999 | Fowler et al. |
| 5,906,662 A | 5/1999 | McCombes |
| 6,022,725 A | 2/2000 | Fowler et al. |
| 6,106,888 A | 8/2000 | Dale et al. |
| 6,176,176 B1 | 1/2001 | Dale et al. |
| 6,235,954 B1 | 5/2001 | Wu et al. |
| 6,268,328 B1 | 7/2001 | Mitchinson et al. |
| 6,429,349 B1 | 8/2002 | Grimes et al. |
| 6,537,336 B2 | 3/2003 | Lancome et al. |
| 6,660,898 B1 | 12/2003 | Pyhalahti et al. |
| 6,896,708 B2 | 5/2005 | Conner et al. |
| 6,949,686 B2 | 9/2005 | Kaminsky et al. |
| 7,014,750 B2 | 3/2006 | Boger et al. |
| 7,132,527 B2 | 11/2006 | Payne et al. |
| 7,169,588 B2 | 1/2007 | Burch et al. |
| 7,241,587 B2 | 7/2007 | Dodge et al. |
| 7,262,041 B2 | 8/2007 | Baldwin et al. |
| 7,338,541 B2 | 3/2008 | Connor et al. |
| 7,399,323 B2 | 7/2008 | Renninger et al. |
| 7,964,762 B2 * | 6/2011 | Bouvart et al. ............ 585/330 |
| 8,173,410 B2 | 5/2012 | Bott et al. |
| 8,450,549 B2 * | 5/2013 | McAuliffe et al. ......... 585/508 |
| 2002/0107423 A1 | 8/2002 | Miyamoto et al. |
| 2007/0191662 A1 | 8/2007 | Oikarinen et al. |
| 2008/0009656 A1 | 1/2008 | D'Amore et al. |
| 2008/0038805 A1 | 2/2008 | Melis |
| 2008/0092829 A1 | 4/2008 | Renninger et al. |
| 2008/0236029 A1 | 10/2008 | Wilkins |
| 2008/0244961 A1 | 10/2008 | Rusek et al. |
| 2009/0020090 A1 | 1/2009 | Ryder et al. |
| 2009/0031617 A1 | 2/2009 | O'Rear |
| 2009/0087890 A1 | 4/2009 | Pyle et al. |
| 2009/0099059 A1 | 4/2009 | Kuppert et al. |
| 2009/0099400 A1 | 4/2009 | Hamamatsu et al. |
| 2009/0099401 A1 | 4/2009 | D'Amore et al. |
| 2009/0145021 A1 | 6/2009 | Guay et al. |
| 2009/0203102 A1 | 8/2009 | Cervin et al. |
| 2009/0203520 A1 | 8/2009 | Blankenship et al. |
| 2009/0287032 A1 | 11/2009 | Brehme et al. |
| 2010/0094072 A1 | 4/2010 | Randolph et al. |
| 2010/0099932 A1 | 4/2010 | Alianell et al. |
| 2010/0145120 A1 * | 6/2010 | Bouvart et al. ............ 585/324 |
| 2010/0196977 A1 | 8/2010 | Chotani et al. |
| 2011/0040058 A1 | 2/2011 | Mcauliffe et al. |
| 2011/0046422 A1 * | 2/2011 | McAuliffe et al. .......... 585/16 |
| 2011/0172475 A1 * | 7/2011 | Peters et al. ............... 585/254 |
| 2011/0178261 A1 | 7/2011 | Feher et al. |
| 2013/0186360 A1 | 7/2013 | Reid |

FOREIGN PATENT DOCUMENTS

| | | |
|---|---|---|
| EP | 0 215 594 B1 | 3/1987 |
| EP | 0 215 594 B2 | 3/1987 |
| EP | 0 238 023 A2 | 9/1987 |
| EP | 0 238 023 A3 | 9/1987 |
| EP | 0 238 023 B1 | 9/1987 |
| EP | 0 283 023 B2 | 9/1987 |
| EP | 0 244 234 A2 | 11/1987 |
| EP | 0 244 234 A3 | 11/1987 |
| EP | 0 244 234 B1 | 11/1987 |
| EP | 0 244 234 B2 | 11/1987 |
| EP | 0 397 266 A2 | 11/1990 |
| EP | 0 137 280 B1 | 3/1992 |
| GB | 1 312 987 A | 4/1973 |
| JP | 48-064049 A | 9/1973 |
| JP | 58-055434 A | 4/1983 |
| JP | 59-065026 A | 4/1984 |
| SU | 493455 A1 | 7/1973 |
| SU | 615056 A1 | 7/1978 |
| TW | 200925264 A | 6/2009 |
| WO | WO-95/04134 A1 | 2/1995 |
| WO | WO-96/35796 A1 | 11/1996 |
| WO | WO-98/02506 A1 | 1/1998 |
| WO | WO-98/02550 A2 | 1/1998 |
| WO | WO-98/02550 A3 | 1/1998 |
| WO | WO-2004/033646 A2 | 4/2004 |
| WO | WO-2004/033646 A3 | 4/2004 |
| WO | WO-2005/001036 A2 | 1/2005 |
| WO | WO-2006/051011 A1 | 5/2006 |
| WO | WO-2007/089901 A2 | 8/2007 |
| WO | WO-2007/089901 A3 | 8/2007 |
| WO | WO-2007/089901 A9 | 8/2007 |
| WO | WO-2008/003078 A2 | 1/2008 |
| WO | WO-2008/003078 A3 | 1/2008 |
| WO | WO-2008/003078 A8 | 1/2008 |
| WO | WO-2008/046106 A2 | 4/2008 |
| WO | WO-2008/137092 A2 | 11/2008 |
| WO | WO-2008/137092 A3 | 11/2008 |
| WO | WO-2009/064910 A2 | 5/2009 |
| WO | WO-2009/064910 A3 | 5/2009 |
| WO | WO-2009/076676 A2 | 6/2009 |
| WO | WO-2009/076676 A3 | 6/2009 |
| WO | WO-2010/003007 A2 | 1/2010 |
| WO | WO-2010/003007 A3 | 1/2010 |
| WO | WO-2010/005525 A1 | 1/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |

OTHER PUBLICATIONS

Akhtar, M. K. et al. (2008). "Deletion of *iscR* Stimulates Recombinant Clostridial Fe—Fe Hydrogenase Activity and $H_2$-Accumulation in *Escherichia coli* BL21(DE3)," *Appl. Microbiol. Biotechnol.* 78:853-862.

Anderson, M. S. et al. (1989). "Isopentenyl Diphosphate: Dimethylallyl Diphosphate Isomerase. An Improved Purification of the Enzyme and Isolation of the Gene From *Saccharomyces cerevisiae*," *J. Biol. Chem.* 264(32):19169-19175.

(56) References Cited

OTHER PUBLICATIONS

De Andrade, D. F. et al. (2010). "Methods For The Determination of Conjugated Dienes In Petroleum Products: A Review," *Fuel* (doi:10.1016/j.fuel.2010.01.003), pp. 1-10.
Aon, J. et al. (Feb. 2008). "Suppressing Posttranslational Gluconoylation of Heterologous Proteins by Metabolic Engineering of *Escherichia coli*," *Applied and Environmental Microbiology* 74(4):950-958.
Aoshima, S. et al. (2009). "A Renaissance in Living Cationic Polymerization," *Chem. Rev.* 109(11):5245-5287.
Billups, W. E. et al. (May 16, 1973). "A Synthesis of (±)-Grandisol," *J. Am. Chem. Soc.* 95(10):3438-3439.
Boel, E. et al. (1984). "Two Different Types of Intervening Sequences in the Glucoamylase Gene from *Aspergillus niger*," *The EMBO Journal* 3(7):1581-1585.
Bond, G. C. et al. (1996). "Catalytic Hydrogenation In The Liquid Phase. Part 1. Hydrogenation of Isoprene Catalysed By Palladium, Palladium-Gold and Palladium-Silver Catalysts," *J. Mol. Catalysis A: Chemical* 109:261-271.
Bouvier, F. et al. (2005). "Biogenesis, Molecular Regulation and Function of Plant Isoprenoids," *Progress in Lipid Res.* 44:357-429.
Bowen, L. E. et al. (2007). "The Selective Trimerisation of Isoprene With Chromium N,N-bis(diarylphosphino)Amine Catalysts," *Chem. Commun.* 2835-2837.
Brown, L. et al. (Aug. 26, 1996). "Enyzymatic Saccharification of Lignocellulosic Biomass," *NREL standard assay method Lap-009*, Procedure # 009, 9 pages.
Bunge, M. et al. (Apr. 2008). "On-Line Monitoring of Microbial Volatile Metabolites by Proton Transfer Reaction-Mass Spectrometry," *Applied and Environmental Microbiology* 74(7):2179-2186.
Burgdorf, T. et al. (2005). "[NiFe]-Hydrogenases of *Ralstonia eutropha* H16: Modular Enzymes For Oxygen-Tolerant Biological Hydrogen Oxidation," *J. Mol. Microbiol. Biotechnol.* 10(2-4):181-196.
Campbell, E. I. et al. (1989). "Improved Transformation Efficiency of *Aspergillus niger* Using the Homologus *nia*D Gene for Nitrate Reductase," *Curr. Genet.* 16:53-56.
Campbell, J. W. et al. (Oct. 2001). "*Escherichia coli* FadR Positively Regulates Transcription of the *fab*B Fatty Acid Biosynthetic Gene," *J. Bacteriol.* 183(20):5982-5990.
Cao, Q-N. et al. (2000). "Penicillopepsin-JT2, a Recombinant Enzyme from *Penicillium janthinellum* and the Contribution of a Hydrogen Bond in Subsite $S_3$ to $k_{cat}$," *Protein Science* 9:991-1001.
Chang, J.-R. et al. (1997). "Catalytic Properties of Eggshell Pd/δ-$Al_2O_3$ Catalysts For Isoprene-Selective Hydrogenation: Effects of Water Poisoning," *Ind. Eng. Chem. Res.* 36:4094-4099.
Chauvin, Y. et al. (1995). "Flüssige 1,3-Dialkylimidazoliumsalze als Lösungsmittel für die Katalyse in Zweiphasensystem: Durch Rhodiumkomplexe Katalysierte Hydierung, Isomerisierung und Hydroformylierung von Alkenen," *Angew. Chem.* 107(23/24):2941-2943, English translation of abstract only (one page).
Chou, C.-J. et al. (2008). "Hydrogenesis in Hyperthermophilic Microorganisms: Implications for Biofuels," *Metabol. Eng.* 10:394-404.
Coplen, T. B. et al. (2006). "New Guidelines for $\delta^{13}C$ Measurements," *Anal. Chem.* 78:2439-2441.
Datsenko, K. et al. (2000). "One-Step Inactivation of Chromosomal Genes In *Escherichia coli* K-12 Using PCR Products," *PNAS* 97(12):6640-6645.
Denis, P. et al. (1990). "Regiocontrolled and Stereocontrolled C—C bond Formation via Linear Dimerization of Conjugated Dienes Catalyzed by Nickel-Aminophosphinite Complexes," *J. Am. Chem. Soc.* 112(3):1292-1294.
Denis, P. et al. (1991). "Linear Dimerization of Conjugated Dienes: A Chemo, Regio and Enantioselective Reaction Catalyzed by Nickel Complexes," *J. Mol. Catalysis* 68(2):159-175.
Dhe-Paganon, S. et al. (1994). "Mechanism of Mevalonate Pyrophosphate Decarboxylase: Evidence for a Carbocationic Transition State," *Biochemistry* 33(45):13355-13362.
Doppelt, P. et al. (1996). "Synthesis and Characterization of a Bis(μ-β-Diketonato)bis(1,2,5,6-η)-1,5-Dimethyl-1,5-cyclooctadiene)disilver Complex. An Intermediate in the Synthesis of an Isomerically Pure (β-Diketonato)((1,2,5,6-η)-1,5-Dimethyl-1,5-Cyclooctadiene)copper(I) Complex," *Inorg. Chem.* 35(5):1286-1291.
Doumith, M. et al. (2000). "Analysis of Genes Involved in 6-Deoxyhexose Biosynthesis and Transfer In *Saccharopolyspora erythraea*," *Mol. Gen. Genet.* 264:477-485.
Funk, T. et al. (2005). "Chemoselective Construction of Substituted Conjugated Dienes Using An Olefin Cross-Metathesis Protocol," *Organic Letters* 7(2):187-190.
GenBank Accession No. AAQ16588, last updated on Feb. 15, 2005, located at <http://www.ncbi.nlm.nih.gov/protein/AAQ16588>, last visited on May 29, 2012, 2 pages.
GenBank Accession No. AAQ84170, last updated on Feb. 15, 2005, located at <http://www.ncbi.nlm.nih.gov/protein/AAQ84170>, last visited on Dec. 22, 2011, 2 pages.
GenBank Accession No. ACD70404, last updated on May 27, 2008, located at <http://www.ncbi.nlm.nih.gov/protein/ACD70404>, last visited on May 29, 2012, 2 pages.
GenBank Accession No. AJ457070, last updated on Apr. 15, 2005, located at <http://www.ncbi.nlm.nih.gov/nuccore/38092202>, last visited on Jun. 2, 2010, 2 pages.
GenBank Accession No. AY182241, last updated on May 4, 2004, located at <http://www.ncbi.nlm.nih.gov/nuccore/32265057>, last visited on Jun. 2, 2010, 2 pages.
GenBank Accession No. AY279379, last updated on Mar. 11, 2005, located at <http://www.ncbi.nlm.nih.gov/nuccore/30984014>, last visited on Jun. 2, 2010, 2 pages.
GenBank Accession No. AY316691, last updated on Feb. 15, 2005, located at <http://www.ncbi.nlm.nih.gov/nuccore/35187003>, last visited on Jun. 2, 2010, 2 pages.
GenBank Accession No. AY341431, last updated on Feb. 15, 2005, located at <http://www.ncbi.nlm.nih.gov/nuccore/33358228>, last visited on Jun. 2, 2010, 3 pages.
GenBank Accession No. BAD98243, last updated on May 10, 2005, located at <http://www.ncbi.nlm.nih.gov/protein/BAD98243>, last visited on Jun. 19, 2012, 2 pages.
GenBank Accession No. CAC35696, last updated Apr. 15, 2005, located at <http://www.ncbi.nlm.nih.gov/protein/CAC35696>, last visited on Nov. 1, 2011, 1 page.
GenBank Accession No. CAJ29303, last updated on Jan. 10, 2007, located at <http://www.ncbi.nlm.nih.gov/protein/CAJ29303>, last visited on May 29, 2012, 1 page.
GenBank Accession No. CAL69918, last updated on Aug. 14, 2008, located at <http://www.ncbi.nlm.nih.gov/protein/CAL69918>, last visited on May 29, 2012, 2 pages.
GenBank Accession No. D86235, last updated on Oct. 29, 1997, located at <http://www.ncbi.nlm.nih.gov/nuccore/D86235>, last visited on Feb. 27, 2012, 2 pages.
GenBank Accession No. NC_003901.1, last updated May 11, 2011, located at <http://www.ncbi.nlm.nih.gov/nuccore/NC_003901.1>, last visited on Oct. 27, 2011, 360 pages.
Goedegebuur, F. et al. (2002). "Cloning and Relational Analysis of 15 Novel Fungal Endoglucanases form Family 12 Glycosyl Hydrolase," *Curr. Genet.* 41:89-98.
Granollers, M. et al. (2010). "Isoamylene Trimerization In Liquid-Phase Over Ion Exchange Resins and Zeolites," *Ind. Eng. Chem. Res.* 49(8):3561-3570.
Graves, D. C. (Nov. 2001). "Alkylation Options For Isobutylene and Isopentane," *Stratco Inc.*, 12 pages.
Grawert, T. et al. (2004, e-pub. Sep. 21, 2004). "IspH Protein of *Escherichia coli*: Studies on Iron—Sulfur Cluster Implementation and Catalysis," *J. Am. Chem. Soc.* 126:12847-12855.
Greenberg, J.P. et al. (1993). "Sub-Parts Per Billion Detection of Isoprene Using a Reduction Gas Detector with a Portable Gas Chromatograph," *Atmosph. Environ.* 27A(16):2689-2692.
Hammond, G. S. et al. (Dec. 1963). "Mechanisms of Photochemical Reactions in Solution. XVI.[1] Photosensitized Dimerization of Conjugated Dienes," *J. Org. Chem.* 28:3297-3303.

(56) References Cited

OTHER PUBLICATIONS

Harkki, A. et al. (Jun. 1989). "A Novel Fungal Expression System: Secretion of Active Calf Chymosin From the Filamentous Fungus *Trichoderma reesei*," *Bio./Technol.* 7:596-603.

Harkki, A. et al. (Mar. 1991). "Genetic Engineering of *Trichoderma* To Produce Strains with Novel Cellulase Profiles," *Enzyme Microb. Technol.* 13:277-233.

Hedl, M. et al. (Apr. 2002). "*Enterococcus faecalis* Acetoacetyl-Coenzyme A Thiolase/3-Hydroxy-3-Methyglutaryl-Coenzyme A Reductase, A Dual-Function Protein of Isopentenyl Diphosphate Biosynthesis," *J. Bacteriol.* 184(8):2116-2122.

Hensen, K. et al. (1997). "Alkoxylation of Limonene and Alpha-Pinene Over Beta Zeolite As Heterogeneous Catalyst," *Applied Catalysis A: General* 149(2):311-329.

Hoeffler, J.-F. et al. (2002). "Isoprenoid Biosynthesis via the Methylerythritol Phosphate Pathway. Mechanistic Investigations of the 1-Deoxy-$_D$-Xylulose 5-Phosphate Reductoisomerase," *Eur. J. Biochem.* 269:4446-4457.

Hsieh, Y.-P. (1992). "Division S-3—Soil Microbiology & Biochemistry," *Soil Sci. Soc. Am J.* 56(2):460-464.

Huchette, D. et al. (1979). "Cyclodimerization Selective Des Diolefines-1,3 Catalysee Par Fe(NO)$_2$," *Tetrahedron Letters* 12:1035-1038.

Hunter, B. K. (1985). "Formaldehyde Metabolism by *Escherichia coli*. Carbon and Solvent Deuterium Incorporation into Glycerol, 1,2-Propanediol, and 1,3-Propanediol," *Biochemistry* 24(15):4148-4155.

Ilmén, M. et al. (Apr. 1997). "Regulation of Cellulase Gene Expression in the Filamentous Fungus *Trichoderma reesei*," *Appl. Environ. Microbiol.* 63(4):1298-1306.

Innis, M. A. et al. (Apr. 5, 1985). "Expression, Glycosylation, and Secretion of an *Aspergillus* Glucoamylase by *Saccharomyces cerevisiae*," *Science* 228:21-26.

Itoh, K. et al. (1994). "Stoichiometric and Catalytic Dimerization of Conjugated Dienes With (C$_5$R$_5$)Ru(diene)$^+$," *Organometallics* 13(3):1020-1029.

Jackstell, R. et al. (2007). "Telomerization and Dimerization of Isoprene by in situ Generated Palladium-Carbene Catalysts," *J. Organometallic Chem.* 692(21):4737-4744.

Julsing, M. K. et al. (2007). "Functional Analysis of Genes Involved in the Biosynthesis of Isoprene in *Bacillus subtilis*," *Applied Microbiol. Biotechnol.* 75:1377-1384, 8 pages.

Kelly, J. M. et al. (1985). "Transformation of *Aspergillus niger* by the *amdS* Gene of *Aspergillus nidulans*," *The EMBO Journal* 4(2):475-479.

King, P. W. et al. (2006). "Functional Studies of [FeFe] Hydrogenase Maturation in an *Escherichia coli* Biosynthetic System," *J. Bacteriol.* 188(6):2163-2172.

Koga, Y. et al. (Mar. 2007). "Biosynthesis of Ether-Type Polar Lipids in Archaea and Evolutionary Considerations," *Microbiology and Molecular Biology Reviews* 71(1):97-120.

Kovach, M.E. et al. (1995). "Four New Derivatives of The Broad-Host-Range Cloning Vector pBBR1MCS, Carrying Different Antibiotic-Resistance Cassettes," *Gene* 166(1):175-176.

Kranz, K. (2003). "Alkylation Chemistry—Mechanisms, Operating Variables, and Olefin Interactions," *Stratco*, 29 pages.

Ladygina, N. et al. (2006). "A Review On Microbial Synthesis of Hydrocarbons," *Process Biochemistry* 41:1001-1014.

Ligabue, R. A. et al. (2001). "Liquid-Liquid Two-Phase Cyclodimerization of 1,3-dienes by Iron-Nitrosyl Dissolved In Ionic Liquids," *J. Mol. Cat. A: Chem.* 169(1-2):11-17.

Lindberg, P. et al. (2010). "Engineering a Platform for Photosynthetic Isoprene Production in Cyanobacteria, Using *Synechocystis* as the Model Organism," *Metabolic Engineering* 12:70-79.

Lüttgen, H. et al. (Feb. 1, 2000). "Biosynthesis of Terpenoids: YchB Protein of *Escherichia coli* Phosphorylates the 2-Hydroxy Group of 4-Diphosphocytidyl-2C-Methyl-$_D$-Erythritol," *PNAS* 97(3):1062-1067.

Maeda, T. et al. (2007). "Enhanced Hydrogen Production from Glucose By Metabolically Engineered *Escherichia coli*," *Appl. Microbiol. Biotechnol.* 77(4):879-890, 12 pages.

Maness, P. et al. (Jun. 2002). "Characterization of the Oxygen Tolerance of a Hydrogenase Linked to a Carbon Monoxide Oxidation Pathway in *Rubrivivax gelatinosus*," *Appl. Environ. Microbiol.* 68(6):2633-2636.

Marchionna, M. et al. (2001). "Light Olefins Dimerization to High Quality Gasoline Components," *Catalysis Today* 65:397-403.

Masotti, H. et al. (1991). "Dimerisation De Dienes Conjugues A L'Aide De Complexes Du Nickel En Presence De Ligands De Type Aminophosphinite Etude d'Optimisation," *Bulletin des Societes Chimiques Belges* 100(1):63-77.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Murphy, M. J. et al. (Sep. 2004). "Compendium of Experimental Cetane Number Data," *NREL*, NREL/SR-540-36805, 51 pages.

Nagy, L. E. et al. (2007). "Application of Gene-Shuffling for the Rapid Generation of Novel [FeFe]-Hydrogenase Libraries," *Biotechnol. Lett.* 29(3):421-430.

Neidhardt, F. C. et al. (Sep. 1974). "Culture Medium for Enterobacteria," *J. Bacteriology* 119(3):736-747.

Nunberg, J. H. et al. (Nov. 1984). "Molecular Cloning and Characterization of the Glucoamylase Gene of *Aspergillus awamori*," *Mol. Cell. Biol.* 4(11):2306-2315.

Oulmouden, A. et al. (1991). "Nucleotide Sequence of the *ERG12* Gene of *Saccharomyces cerevisiae* Encoding Mevalonate Kinase," *Curr. Genet.* 19:9-14.

Penttilä, M. et al. (1987). "A Versatile Transformation System for the Cellulolytic Filamentous Fungus *Trichoderma reesei*," *Gene* 61:155-164.

Perego, M. (1993). "Integrational Vectors for Genetic Manipulation in *Bacillus subtilis*," Chapter 42 in *Bacillus subtilis and Other Gram-Positive Bacteria: Biochemistry, Physiology, and Molecular Genetics*, Sonenshein et al. eds., American Society for Microbiology: Washington, D.C., pp. 615-624.

Pereira, R. C. C. et al. (2006). "Effect of Mono-Olefins and Diolefins On The Stability of Automotive Gasoline," *Fuel* 85:1860-1865.

Peterson, J. R. et al. (1999). "Improved Amylene Alkylation Economics," *Stratco*, pp. 1-9.

Pommer, H. et al. (1975). "Industrial Synthesis of Terpene Compounds," *Pure Appl. Chem.* 43:527-551.

Rohdich, F. et al. (Oct. 12, 1999). "Cytidine 5'-Triphosphate-Dependent Biosynthesis of Isoprenoids: YgbP Protein of *Escherichia coli* Catalyzes the Formation of 4-Diphosphocytidyl-2-*C*-Methylerythritol," *PNAS* 96(21):11758-11763.

Rohdich, F. et al. (Jun. 6, 2000). "Biosynthesis of Terpenoids: 4-Diphosphocytidyl-2C-Methyl-$_D$-Erythritol Synthase of *Arabidopsis thaliana*," *PNAS* 97(12):6451-6456.

Sanchez, C. et al. (Apr. 2002). "The Biosynthetic Gene Cluster For The Antitumor Rebeccamycin: Characterization and Generation of Indolocarbazole Derivatives," *Chem. Biol.* 9(4):519-531.

Schnitzler, J.-P. et al. (2005). "Biochemical Properties of Isoprene Synthase In Poplar (*Populus x canescens*)," *Planta* 222:777-786.

Seedorf, H. et al. (Feb. 12, 2008). "The Genome of *Clostridium kluyveri*, A Strict Anaerobe With Unique Metabolic Features," *PNAS* 105(6):2128-2133.

Sharkey, T. D. et al. (Feb. 2005). "Evolution of the Isoprene Biosynthetic Pathway in Kudzu," *Plant Physiology* 137:700-712.

Sheir-Neiss, G. et al. (1984). "Characterization of the Secreted Cellulases of *Trichoderma reesei* Wild Type and Mutants During Controlled Fermentations," *Appl. Microbiol. Biotechnol.* 20(1):46-53.

Silver, G. M. et al. (1991). "Enzymatic Synthesis of Isoprene from Dimethylallyl Diphosphate in Aspen Leaf Extracts," *Plant Physiol.* 97:1588-1591.

Silver, G. M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Sprenger, G. A. et al. (Nov. 1997). "Identification of a Thiamin-Dependent Synthase in *Escherichia coli* Required for the Formation

(56) References Cited

OTHER PUBLICATIONS of the 1-Deoxy-$_D$-Xylulose 5-Phosphate Precursor to Isoprenoids, Thiamin, and Pyridoxol," *PNAS* 94:12857-12862.

Suga, K. et al. (1972). "Thermal Isomerization of 1,5-Dimethyl-1-Cyclooctene," *Israel J. Chem.* 10(1):15-18.

Suga, K. et al. (1973). "The Oligomerisation of Isoprene Catalysed by Nickel Naphthenate and Isoprene Magnesium," *J. Appl. Chem. Biotechnol.gy* 23(2):131-138.

Sulter, G. J. et al. (1990). "Proliferation and Metabolic Significance of Peroxisomes in *Candida boidinii* During Growth on D-Alanine or Oleic Acid as the Sole Carbon Source," *Arch. Microbiol.* 153:485-489.

Sutherlin, A. et al. (Aug. 2002). "*Enterococcus faecalis* 3-Hydroxy-3-Methylglutaryl Coenzyme A Synthase, an Enzyme of Isopentenyl Diphosphate Biosynthesis," *J. Bacteriol.* 184(15):4065-4070.

Teymouri, F. et al. (2005, e-pub. Feb. 24, 2005). "Optimization of the Ammonia Fiber Explosion (AFEX) Treatment Parameters for Enzymatic Hydrolysis of Corn Stover," *Bioresource Technology* 96:2014-2018.

Tracy, N. I. et al. (2009). "Hydrogenated Monoterpenes As Diesel Fuel Additives," *Fuel* 88:2238-2240.

Tsay, Y.H. et al. (Feb. 1991). "Cloning and Characterization of *ERG8*, an Essential Gene of *Saccharomyces cerevisiae* That Encodes Phosphomevalonate Kinase," *Mol. Cell. Biol.* 11(2):620-631.

Vardar-Schara, G. et al. (2008). "Metabolically Engineered Bacteria For Producing Hydrogen Via Fermentation," *Microbial Biotechnol.* 1(2):107-125.

Wagner, W.P. et al. (Aug. 1999). "Three Distinct Phases of Isoprene Formation During Growth and Sporulation of *Bacillus subtilis*," *Journal of Bacteriology* 181(15):4700-4703.

Ward, M. et al. (1993). "Use of *Aspergillus* Overproducing Mutants, Cured For Integrated Plasmid, To Overproduce Heterologous Proteins," *Appl. Microbiol. Biotechnol.* 39(6):738-743.

Weber, D. et al. (1997). C-Pattern of Natural Glycerol: Origin and Practical Importance, *J. Agric.Food Chem.* 45:2042-2046.

Withers, S. et al. (Oct. 2007, e-pub. Aug. 10, 2007). "Identification of Isopentenol Biosynthetic Genes from *Bacillus subtilis* by a Screening Method Based on Isoprenoid Precursor Toxicity," *Appl. Environ Microbiol.* 73(19):6277-6283.

Woerlee, E. F. G. et al. (1984). "Metathesis of Conjugated Dienes: A Possible Way to Synthesise Insect Pheromones and Other Speciality Chemicals," *Applied Catalysis* 10:219-229.

Woodward, J. et al. (Jun. 29, 2000). "Enzymatic Production of Biohydrogen," *Nature* 405(6790):1014-1015.

World-wide web (2012) URL located at www.expasy.org, last visited on May 29, 2012, Swiss Institute of Bioinformatics Swiss-Prot group CMU—1 rue Michel Servet, CH-1211 Geneva 4, Switzerland, one page.

World-wide web (Sep. 21, 2011). URL located at fgsc.net, last visited on Jul. 11, 2012, "Fungal Genetics Stock Center Catalogue of Strains," FGSC, one page.

World-wide web (2012). URL located at http://www.genome.jp/kegg/, last visited on Aug. 22, 2012, one page.

Yamada, K. et al. (1989). "Production of Glycerol from Methanol by a Mutant Strain of *Candida boidinii* No. 2201," *Agric. Biol. Chem.* 53(2):541-543.

Yelton, M. M. et al. (Mar. 1984). "Transformation of *Aspergillus nidulans* by Using a *trpC* Plasmid," *PNAS* 81:1470-1474.

Yoshida, A. et al. (2007, e-pub. Nov. 17, 2006). "Efficient Induction of Formate Hydrogen Lyase of Aerobically Grown *Escherichia coli* in a Three-Step Biohydrogen Production Process," *Appl. Microbiol. Biotechnol.* 74:754-760.

Zabetakis, M. G. (1965). "Flammability Characteristics of Combustible Gases and Vapors," published by the former U.S. Bureau of Mines, Bulletin 627, 123 pages.

Zakharkin, L. I. et al. (1976). "Dimerization of Isoprene in Methanol Using Palladium Complexes," Translated from *Izvestiya Akademii Nauk SSSR, Seriya Khimicheskaya*, 9:2099-2100, published in Sep. 1976, *Russ. Chem. Bull.* pp. 1967-1968.

Zakharkin, L. I. et al. (1987). "Cyclooligomerization of Isoprene On Complexed Nickel and Iron Catalysts," Translated from *Zhurnal Obshchei Khimii* (*Russian Journal of General Chemistry*) 57(11):2551-2556, Nov. 1987, original article submitted on Aug. 5, 1986, English translation of article published by Plenum Publishing Corporation in 1988, pp. 2271-2275.

Zepeck, F. et al. (2005, e-pub. Oct. 14, 2005). "Biosynthesis of Isoprenoids. Purification and Properties of IspG Protein from *Escherichia coli*," *J. Org. Chem.* 70:9168-9174.

Zweni, P. P. et al. (2006). "Silica-Supported Dendrimer-Palladium Complex-Catalyzed Selective Hydrogenation of Dienes to Monoolefins," *Adv. Synth. Catal.* 348:725-731.

International Search Report mailed on Sep. 6, 2011, for PCT Patent Application No. PCT/US2011/040977, filed on Jun. 17, 2011, 2 pages.

* cited by examiner

Figure 1
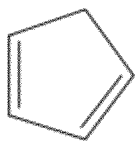
cyclopentadiene
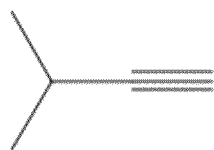
"isopryne" = 3-Me-1-butyne
trans-piperylene
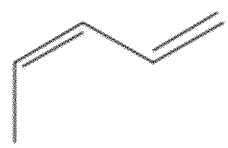
cis-piperylene
1-pentyne
pent-4-ene-1-yne
trans-pent-3-ene-1-yne
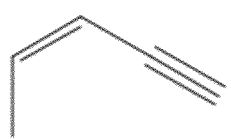
cis-pent-3-ene-1-yne

FUEL COMPOSITIONS COMPRISING ISOPRENE DERIVATIVES

CROSS REFERENCE TO RELATED APPLICATION

This application claims priority to U.S. Provisional Application No. 61/356,017, filed Jun. 17, 2010, and U.S. Provisional Application No. 61/426,481, filed Dec. 22, 2010, both of which are incorporated herein by reference in its entirety.

BACKGROUND OF THE INVENTION

The development of renewable transportation fuels is one of the key challenges of the twenty-first century. The current market is dominated by ethanol derived from yeast fermentation of sucrose and starch, and to a lesser extent by biodiesel (fatty acid esters) derived from triglycerides. Ethanol has limitations as a liquid fuel with a lower energy density relative to hydrocarbons. In addition, ethanol cannot be transported in conventional infrastructure due to its affinity for water and corrosive nature. Processes for the conversion of renewable carbon sources (biomass, sugars, oils) to hydrocarbon fuels offer an attractive alternative to bioethanol.

Isoprene (2-methyl-1,3-butadiene) is a key industrial chemical used primarily for the production of synthetic rubber. Currently isoprene is derived from petrochemical sources either directly by cracking of naphtha and other light petroleum fractions, or indirectly through chemical synthesis (See, for examples, H. Pommer and A. Nurrenbach, Industrial Synthesis of Terpene Compounds, *Pure Appl. Chem.*, 1975, 43, 527-551; H. M. Weitz and E. Loser, Isoprene, in *Ullmann's Encyclopedia of Industrial Chemistry*, Seventh Edition, Electronic Release, Wiley-VCH Verlag GMBH, Weinheim, 2005; and H. M. Lybarger, Isoprene in *Kirk-Othmer Encyclopedia of Chemical Technology*, 4th ed., Wiley, New York (1995), 14, 934-952.) The resulting crude isoprene streams are typically subjected to extensive purification processes in order to remove numerous chemically similar impurities, many of which can interfere with subsequent transformation of isoprene to polymers and other chemicals.

In contrast, isoprene derived from biological sources contains very few hydrocarbon impurities and instead contains a number of oxygenated compounds such as ethanol, acetaldehyde and acetone. Many of these compounds can be easily removed by contact with water or passage through alumina or other adsorbents.

Due to the requirement of extensive purification and cost associated with obtaining high purity isoprene, isoprene derived from petroleum processes have not been a viable starting material for further processing to produce fuels. Cost effective methods are desirable for converting biologically produced isoprene to valuable chemical products, fuel in particular, taking advantage of the high purity and/or the unique impurity profiles of bioisoprene compositions.

All patents, patent applications, documents, and articles cited herein are herein incorporated by reference in their entirety.

BRIEF SUMMARY OF THE INVENTION

The invention provides, inter alia, for compositions and methods for producing a fuel constituent from a bioisoprene composition. More specifically, it provides compositions and methods for using a unique combination of starting materials and chemical reactions to convert isoprene in a bioisoprene composition to fuel constituents.

Accordingly, in one aspect, the invention provides for methods of chemically transforming a substantial portion of the isoprene in the bioisoprene composition to one or more non-isoprene compounds by: (a) contacting the bioisoprene composition with a catalyst for olefin metathesis to produce one or more olefin products and then catalytically hydrogenating the one or more olefin products to form one or more alkane fuel constituents; (b) partially hydrogenating the bioisoprene composition to produce an isoamylene and then alkylating the isoamylene with an isoparaffin to form a high octane alkylate fuel constituent; or (c) partially hydrogenating the bioisoprene composition to produce an isoamylene, then contacting the isoamylene with a catalyst for olefin metathesis to produce one or more olefin products, and then catalytically hydrogenating the one or more olefin products to form one or more alkane fuel constituents. In one embodiment, at least about 95% of isoprene in the bioisoprene composition is converted to non-isoprene compounds. In another embodiment, the bioisoprene composition comprises or contains greater than about 2 mg of isoprene and comprises or contains greater than or about 99.94% isoprene by weight compared to the total weight of all C5 hydrocarbons in the composition. In another embodiment, the olefin metathesis catalyst comprises or involves, at least, a metal complex. In another embodiment, the metal complex is a rhenium complex, a ruthenium complex, a rhodium complex, an osmium complex, a tungsten complex, a molybdenum complex or a titanium complex. In another embodiment, the olefin product comprises a higher (>C5) olefin or a lower (<C5) olefin or both. In another embodiment, the one or more olefin products from isoprene metathesis comprise one or more olefins selected from the group consisting of ethylene, isobutylene and olefins containing 6, 8 and 12 carbon atoms (e.g., dimethylhexatrienes). In another embodiment, the step of partially hydrogenating the bioisoprene composition comprises contacting the bioisoprene composition with hydrogen gas and a catalyst for catalyzing partial hydrogenation of isoprene. In another embodiment, the catalyst for catalyzing partial hydrogenation of isoprene comprises a palladium catalyst. In other embodiments, the step of alkylating the isoamylene with an isoparaffin comprises contacting the isoamylene with the isoparaffin in the presence of an acid catalyst. In another embodiment, the acid catalyst is hydrofluoric acid, sulfuric acid, fluorosulfonic acid or perhaloalkylsulfonic acid. In other embodiments, the isoparaffin is propane, isobutane or isopentane. In some embodiments, the olefin metathesis catalyst for isoamylene metathesis is different from the olefin metathesis catalyst for bioisoprene metathesis. In some embodiments, the olefin metathesis catalyst for isoamylene metathesis is the same as the olefin metathesis catalyst for bioisoprene metathesis. In some embodiments, the olefin product from isoamylene metathesis comprises one or more olefins selected from the group consisting of ethylene and olefins containing 6, 8 and 12 carbon atoms (e.g., dimethylhexenes).

In another aspect, the invention provides systems for producing a fuel constituent from a bioisoprene composition comprising a bioisoprene composition and: (a) (i) one or more catalysts for catalyzing metathesis of isoprene in the bioisoprene composition to form an olefin product, and (ii) a catalyst capable of hydrogenating the olefin product to form an alkane fuel constituent; or (b) (i) a chemical capable of partially hydrogenating isoprene in the bioisoprene composition to produce an isoamylene, and (ii) a isoparaffin for alkylating the isoamylene derived from the bioisoprene composition to produce a fuel constituent; or (c) (i) a chemical capable of partially hydrogenating isoprene in the bioisoprene composition to produce an isoamylene, (ii) one or more catalysts for catalyzing metathesis of the isoamylene produced from partial hydrogenation of the bioisoprene composition to form an olefin product, and (iii) a catalyst capable of hydrogenating the olefin product to form an alkane fuel constituent; wherein a substantial portion of the isoprene in the bioisoprene composition is chemically converted to one or more non-isoprene compounds. In one embodiment, the bioisoprene composition comprises greater than about 2 mg of isoprene and comprises greater than or about 99.94% isoprene by weight compared to the total weight of all C5 hydrocarbons in the composition. In other embodiments, the catalyst for catalyzing metathesis of isoprene comprises a rhenium complex, a ruthenium complex, a rhodium complex, an osmium complex, a tungsten complex, a molybdenum complex or a titanium complex. In other embodiments, the olefin product comprises a higher (>C5) olefin or a lower (<C5) olefin or both. In other embodiments, the olefin product comprises one or more olefins selected from the group consisting of ethylene, isobutylene, dimethylhexatrienes and cyclic olefins containing 6, 8 and 12 carbon atoms. In other embodiments, the catalyst for hydrogenating the one or more olefin products to form one or more alkane fuel constituents comprises a catalyst selected from the group consisting of palladium catalysts, nickel catalysts, cobalt catalysts, ruthenium catalysts and rhodium catalysts. In other embodiments, the chemical capable of partially hydrogenating isoprene in the bioisoprene composition to produce an isoamylene comprises a hydrogen gas and a catalyst for catalyzing partial hydrogenation of isoprene. In other embodiments, the catalyst for catalyzing partial hydrogenation of isoprene comprises a palladium catalyst. In other embodiments, the isoparaffin for alkylating the isoamylene is propane, isobutane or isopentane. In other embodiments, the system further comprises an acid catalyst for alkylating isoamylene. In other embodiments, the catalyst for alkylating isoamylene is hydrofluoric acid, sulfuric acid, fluorosulfonic acid or perhaloalkylsulfonic acid. In some embodiments, the catalyst for catalyzing metathesis of isoamylene comprises a rhenium complex, a ruthenium complex, a rhodium complex, an osmium complex, a tungsten complex, a molybdenum complex or a titanium complex. In some embodiments, the olefin metathesis catalyst for isoamylene metathesis is different from the olefin metathesis catalyst for bioisoprene metathesis. In some embodiments, the olefin metathesis catalyst for isoamylene metathesis is the same as the olefin metathesis catalyst for bioisoprene metathesis. In other embodiments, the olefin product comprises a higher (>C5) olefin or a lower (<C5) olefin or both. In some embodiments, the olefin product from isoamylene metathesis comprises one or more olefins selected from the group consisting of ethylene and olefins containing 6, 8 and 12 carbon atoms (e.g., dimethylhexenes).

In another aspect, the invention provides fuel constituents produced by any method described herein. In other embodiments, the fuel constituents have a $\delta^{13}C$ value which is greater than −22‰ or within the range of −32‰ to −24‰.

In another aspect, the invention provides fuel compositions comprising a fuel constituent produced by any method described herein. In one embodiment, the fuel composition is substantially free of isoprene. In other embodiments, the fuel composition has $\delta^{13}C$ value which is greater than −22‰ or within the range of −32‰ to −24‰.

In another aspect, the invention provides methods for producing a fuel constituent from a bioisoprene composition comprising: (i) contacting a bioisoprene composition with an acid catalyst to produce one or more mixed olefin products (e.g., C5-C50 olefins) comprising higher molecular weight olefin products (e.g., C16-C50 olefins) and lower molecular weight olefin products (e.g., C5-C15 olefins); (ii) converting the higher molecular weight olefin products (e.g.; C16-C50 olefins) to lower molecular weight olefin products (e.g.; C5-C15 olefins); and (iii) hydrogenating the lower molecular weight olefin products (e.g.; C5-C15 olefins) to produce saturated hydrocarbon (e.g.; C5-C15 alkanes) fuel constituents; wherein a substantial portion of the isoprene in the bioisoprene composition is chemically converted to one or more non-isoprene compounds. In one embodiment, the step of converting the higher molecular weight olefin products (e.g.; C16-C50 olefins) to lower molecular weight olefin products (e.g.; C5-C15 olefins) comprises thermal cracking, steam cracking or metathesis.

In another aspect, the invention provides for systems for producing a fuel constituent comprising: (a) a fermentation system comprising bioisoprene composition; and (b) (i) one or more catalysts for catalyzing metathesis of isoprene in the bioisoprene composition to form an olefin product, and (ii) a catalyst capable of hydrogenating the olefin product to form an alkane fuel constituent, wherein a substantial portion of the isoprene in the bioisoprene composition is chemically converted to one or more non-isoprene compounds.

In another aspect, the invention provides for systems for producing a fuel constituent comprising: (a) a fermentation system comprising bioisoprene composition; and (c) (i) a chemical capable of partially hydrogenating isoprene in the bioisoprene composition to produce an isoamylene, and (ii) a isoparaffin for alkylating the isoamylene derived from the bioisoprene composition to produce a fuel constituent, wherein a substantial portion of the isoprene in the bioisoprene composition is chemically converted to one or more non-isoprene compounds.

In another aspect, the invention provides for systems for producing a fuel constituent comprising: (a) a fermentation system comprising bioisoprene composition; and (d) (i) a chemical capable of partially hydrogenating isoprene in the bioisoprene composition to produce an isoamylene, (ii) one or more catalysts for catalyzing metathesis of the isoamylene produced from partial hydrogenation of the bioisoprene composition to form an olefin product, and (iii) a catalyst capable of hydrogenating the olefin product to form an alkane fuel constituent, wherein a substantial portion of the isoprene in the bioisoprene composition is chemically converted to one or more non-isoprene compounds.

In another aspect, for any of the systems above, the fermentation system is a continuous fermentation system. In another aspect, the fermentation system is selected from the group consisting of batch fermentation, fed-batch fermentation, continuous fermentation, and continuous with recycle processes fermentation. In yet another aspect, in any of the systems described herein, at least 99% of the bioisoprene composition is in gaseous phase.

BRIEF DESCRIPTION OF THE DRAWINGS

FIG. 1 shows the structures of several impurities that are structurally similar to isoprene and may also act as polymerization catalyst poisons.

DETAILED DESCRIPTION OF THE INVENTION

Figure 2:
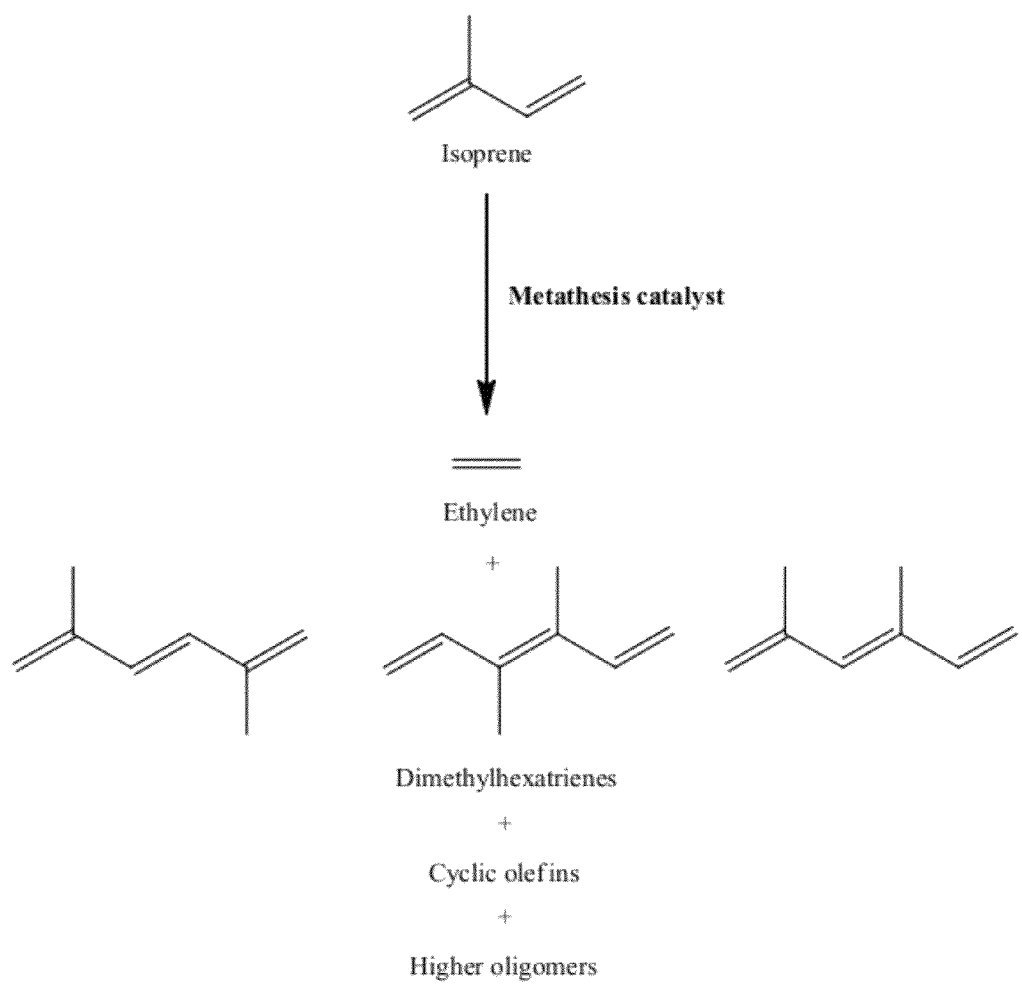
FIG. 2 shows a reaction scheme for the conversion of isoprene to ethylene, dimethylhexatrienes and higher oligomers using a metathesis catalyst.

The invention provides, inter alia, methods, compositions and systems for producing fuel constituents from isoprene. The fuel constituents can be produced by chemical transformations of a starting material that includes a commercially beneficial amount of highly pure isoprene, such as can found by starting with a bioisoprene composition. Fuel constituents that can be produced by the methods and system of the invention include, but are not limited to, hydrocarbons derived from isoprene metathesis, isoprene oligomers and alkylates of isoamylenes derived from isoprene. The fuel constituents can be used for making various fuel compositions. In addition, the products made by the chemical transformation of a bioisoprene composition have other uses as further described herein.

DEFINITIONS

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials as well as methods and materials which can be used are described herein. Accordingly, the terms defined immediately below are more fully described by reference to the Specification as a whole. All documents cited are, in relevant part, incorporated herein by reference. However, the citation of any document is not to be construed as an admission that it is prior art with respect to the present invention.

As used herein, the term "fuel constituent" refers to a compound useful as a fuel component or fuel additive.

As used herein, "at least a portion of the isoprene starting composition" can refer to at least about 1%, 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.6%, 99.7%, 99.8%, 99.9%, or 100% of the isoprene starting composition undergoing chemical transformation.

As used herein, the term "higher olefin" refers to olefins containing more carbon atoms in each molecule than that in isoprene. For examples, C6-C12 olefins and C7-C15 olefins are higher olefins.

As used herein, the term "lower olefin" refers to olefins containing fewer or equal number of carbon atoms in each molecule than that in isoprene. For examples, C2-C4 olefins and C2-C5 olefins are lower olefins.

The term "isoprene" refers to 2-methyl-1,3-butadiene (CAS#78-79-5). It can be the direct and final volatile C5 hydrocarbon product from the elimination of pyrophosphate from 3,3-dimethylallyl pyrophosphate (DMAPP), and does not involve the linking or polymerization of [an] isopentenyl diphosphate (IPP) molecule(s) to [a] DMAPP molecule(s). The term "isoprene" is not generally intended to be limited to its method of production unless indicated otherwise herein.

As used herein, "biologically produced isoprene" or "bioisoprene" is isoprene produced by any biological means, such as produced by genetically engineered cell cultures, natural microbials, plants or animals.

A "bioisoprene composition" refers to a composition that can be produced by any biological means, such as systems (e.g., cells) that are engineered to produce isoprene. It contains isoprene and other compounds that are co-produced (including impurities) and/or isolated together with isoprene. A bioisoprene composition has a different impurity profile from a petrochemically produced isoprene composition. As further detailed herein, a bioisoprene composition is distinguished from a petro-isoprene composition in that a bioisoprene composition is substantially free of any contaminating unsaturated C5 hydrocarbons that are usually present in petro-isoprene compositions, such as, but not limited to, 1,3-cyclopentadiene, trans-1,3-pentadiene, cis-1,3-pentadiene, 1,4-pentadiene, 1-pentyne, 2-pentyne, 3-methyl-1-butyne, pent-4-ene-1-yne, trans-pent-3-ene-1-yne, and cis-pent-3-ene-1-yne. If any contaminating unsaturated C5 hydrocarbons are present in the bioisoprene starting material described herein, they are present in lower levels than the levels of such contaminating unsaturated C5 hydrocarbons in petro-isoprene compositions. Accordingly, any fuel products derived from bioisoprene compositions described herein are essentially free of any such contaminating unsaturated C5 hydrocarbons, or contain such contaminating unsaturated C5 hydrocarbons at lower levels than the levels of such contaminating unsaturated C5 hydrocarbons in fuel products derived from petroleum or fossil fuels. In addition, the sulfur levels in a bioisoprene composition are lower than the sulfur levels in petro-isoprene compositions. Fuels products derived from bioisoprene compositions contain lower levels of sulfur than the levels of sulfur in fuel products derived from crude fossil oil.

"Fermentation system" as used herein refers to any cell culture system that is capable of producing bioisoprene.

The term "oligomerization" as used herein refers to a chemical process for combining two or more monomer units. "Oligomerization" of isoprene produces a derivative of isoprene derived from two or more molecules of isoprene, such as linear dimers of isoprene, cyclic dimers of isoprene, linear trimers of isoprene, cyclic trimers of isoprene and the like.

"Complete hydrogenation", "completely hydrogenate" or "fully hydrogenate" is defined as the addition of hydrogen ($H_2$), typically in the presence of a hydrogenation catalyst, to all unsaturated functional groups, such as carbon-carbon double bonds, within a precursor compound to give fully saturated product compounds. For example, complete hydrogenation of isoprene forms isopentane whereby 2 moles of $H_2$ is consumed per mole of isoprene.

"Partial hydrogenation" or "partially hydrogenate" is defined as the addition of hydrogen ($H_2$), typically in the presence of a hydrogenation catalyst, to at least one, but not all unsaturated functional groups, such as carbon-carbon double bonds, within a precursor compound. The product(s) of partial hydrogenation can be further completely hydrogenated to give fully saturated product compounds. Partial hydrogenation of a diene forms one or more mono-olefins. For example, partial hydrogenation of isoprene can give 3 isomeric isopentenes (2-methyl-1-butene, 2-methyl-2-butene and 3-methyl-1-butene) whereby 1 mole of $H_2$ is consumed per mole of isoprene.

"Selective hydrogenation" or "selectively hydrogenate" is defined as the addition of hydrogen ($H_2$), typically in the presence of a hydrogenation catalyst, to at least one, but not all unsaturated functional groups, such as carbon-carbon double bonds, within a precursor compound whereby certain unsaturated functional groups are preferentially hydrogenated over other unsaturated groups under the chosen conditions. For example, selective hydrogenation of isoprene may form preferentially 2-methyl-2-butene, 2-methyl-1-butene, 3-methyl-1-butene or a mixture thereof.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Bioisoprene Compositions and Systems

The invention provides, inter alia, methods, compositions and systems for producing fuel constituents and other products from isoprene. The fuel constituents can be produced by chemical transformations of a starting material that includes a commercially beneficial amount of highly pure isoprene, such as can found by starting with a bioisoprene composition.

Isoprene derived from petrochemical sources usually is an impure C5 hydrocarbon fraction which requires extensive purification before the material is suitable for polymerization or other chemical transformations. Several impurities are particularly problematic given their structural similarity to isoprene and the fact that they can act as polymerization catalyst poisons. Such compounds include, but are not limited to, 1,3-cyclopentadiene, cis- and trans-1,3-pentadiene, 1,4-pentadiene, 1-pentyne, 2-pentyne, 3-methyl-1-butyne, pent-4-ene-1-yne, trans-pent-3-ene-1-yne, and cis-pent-3-ene-1- yne. See, for example, FIG. 1. As detailed below, biologically produced isoprene can be substantially free of any contaminating unsaturated C5 hydrocarbons without undergoing extensive purification. The biological system producing the isoprene yields a composition that contains isoprene, in addition to other impurities that are specific for a biological system. This composition is referred to as "bioisoprene composition" herein. Some bioisoprene compositions contain ethanol, acetone, and C5 prenyl alcohols. These components are more readily removed from the isoprene stream than the isomeric C5 hydrocarbon fractions that are present in isoprene compositions derived from petrochemical sources. Further, these impurities can be managed in the bioprocess, for example by genetic modification of the producing strain, carbon feedstock, alternative fermentation conditions, recovery process modifications and additional or alternative purification methods.

Cells Capable of Isoprene Production

Microorganisms can be engineered to produce isoprene. Further, other co-products can also be made with the isoprene. The cells can be engineered to contain a heterologous nucleic acid encoding an isoprene synthase polypeptide. Various isoprene synthase polypeptides, DXP pathway polypeptides or DXS pathway polypeptides, IDI polypeptides, MVA pathway polypeptides, hydrogenase polypeptides, hydrogenase maturation or transcription factor polypeptides and nucleic acids can be used in the compositions and methods for production of the starting bioisoprene composition. Exemplary nucleic acids, polypeptides and enzymes that can be used are described in WO 2009/076676 and WO 2010/003007, both of which would also include the Appendices listing exemplary isoprene synthase, DXP pathway, MVA pathway, acetyl-CoA-acetyltransferase, HMG-CoA synthase, hydroxymethylglutaryl-CoA reductase, mevalonate kinase, phosphomevalonate kinase, diphosphomevalonate decarboxylase, isopentenyl phosphate kinases (IPK), isopentenyl-diphosphate Delta-isomerase (IDI) polypeptides and nucleic acids, and other polypeptide and nucleic acids that one of skill in the art can use to make cells which produce isoprene.

Isoprene Synthase

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase which confer additional activity may be used as well. Also included are mutant isoprene synthase polypeptides derived from any of the source organisms described herein that have at least one isoprene synthase activity.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one embodiment, DMAPP (Sigma-Aldrich, Wis.) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M $MgCl_2$, 1 mM (250 µg/ml) DMAPP, 65 µL of Plant Extract Buffer (PEB) (50 mM Tris-HCl, pH 8.0, 20 mM $MgCl_2$, 5% glycerol, and 2 mM DTT) can be added to 25 µL of cell extract in a 20 ml Headspace vial with a metal screw cap and teflon coated silicon septum (Agilent Technologies) and cultured at 37° C. for 15 minutes with shaking. The reaction can be quenched by adding 200 µL of 250 mM EDTA and quantified by GC/MS.

In some embodiments, the isoprene synthase polypeptide or nucleic acid is from the family Fabaceae, such as the Faboideae subfamily. In some embodiments, the isoprene synthase polypeptide or nucleic acid is a polypeptide or nucleic acid from *Pueraria montana* (kudzu) (Sharkey et al., Plant Physiology 137:700-712, 2005), *Pueraria lobata*, poplar (such as *Populus alba, Populus nigra, Populus trichocarpa*, or *Populus alba×tremula* (CAC35696) Miller et al., Planta 213:483-487, 2001) aspen (such as *Populus tremuloides*) Silver et al., JBC 270(22):13010-1316, 1995), or English Oak (*Quercus robur*) (Zimmer et al., WO 98/02550). Suitable isoprene synthases include, but are not limited to, those identified by Genbank Accession Nos. AY341431, AY316691, AY279379, AJ457070, and AY182241. In some embodiments, the isoprene synthase nucleic acid or polypeptide is a naturally-occurring polypeptide or nucleic acid from poplar. In some embodiments, the isoprene synthase nucleic acid or polypeptide is not a naturally-occurring polypeptide or nucleic acid from poplar.

Types of isoprene synthases which can be used and methods of making microorganisms (e.g., facultative anaerobes such as *E. coli*) encoding isoprene synthase are also described in International Patent Application Publication Nos. WO2009/076676, WO2010/003007, WO 2009/132220, WO 2010/031062, WO2010/031068, WO 2010/031076, WO2010/031077, WO2010/031079, WO2010/148150, WO2010/005525, WO 2010/078457, WO2010/124146, WO2010/148144, WO2010/148256 and U.S. patent application Ser. Nos. 12/496,573, 12/560,390, 12/560,317, 12/560,370, 12/560,305, and 12/560,366.

Exemplary DXP Pathway Polypeptides and Nucleic Acids

DXS and IDI polypeptides are part of the DXP pathway for the biosynthesis of isoprene. 1-deoxy-D-xylulose-5-phosphate synthase (DXS) polypeptides convert pyruvate and D-glyceraldehyde-3-phosphate into 1-deoxy-D-xylulose-5-phosphate. While not intending to be bound by any particular theory, it is believed that increasing the amount of DXS polypeptide increases the flow of carbon through the DXP pathway, leading to greater isoprene production.

Exemplary DXS polypeptides include polypeptides, fragments of polypeptides, peptides, and fusions polypeptides that have at least one activity of a DXS polypeptide. Standard methods known to one of skill in the art and as taught the references cited herein can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS nucleic acids include nucleic acids that encode a polypeptide, fragment of a polypeptide, peptide, or fusion polypeptide that has at least one activity of a DXS polypeptide. Exemplary DXS polypeptides and nucleic acids include naturally-occurring polypeptides and nucleic acids from any of the source organisms described herein as well as mutant polypeptides and nucleic acids derived from any of the source organisms described herein.

MVA Pathway

In some aspects of the invention, the cells described in any of the compositions or methods described herein comprise a nucleic acid encoding an MVA pathway polypeptide. In some embodiments, the MVA pathway polypeptide is an endogenous polypeptide. In some embodiments, the cells comprise one or more additional copies of an endogenous nucleic acid encoding an MVA pathway polypeptide. In some embodiments, the endogenous nucleic acid encoding an MVA pathway polypeptide operably linked to a constitutive promoter. In some embodiments, the endogenous nucleic acid encoding an MVA pathway polypeptide operably linked to a constitutive promoter. In some embodiments, the endogenous nucleic acid encoding an MVA pathway polypeptide is operably linked to a strong promoter. In a particular embodiment, the cells are engineered to over-express the endogenous MVA pathway polypeptide relative to wild-type cells.

In some embodiments, the MVA pathway polypeptide is a heterologous polypeptide. In some embodiments, the cells comprise more than one copy of a heterologous nucleic acid encoding an MVA pathway polypeptide. In some embodiments, the heterologous nucleic acid encoding an MVA pathway polypeptide is operably linked to a constitutive promoter. In some embodiments, the heterologous nucleic acid encoding an MVA pathway polypeptide is operably linked to a strong promoter.

Exemplary MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonate decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

In one embodiment, aerobes are engineered with isoprene synthase using standard techniques known to one of skill in the art. In another embodiment, anaerobes are engineered with isoprene synthase and one or more MVA pathway polypeptides using standard techniques known to one of skill in the art. In yet another embodiment, either aerobes or anaerobes are engineered with isoprene synthase, one or more MVA pathway polypeptides and/or one or more DXP pathway polypeptides using standard techniques known to one of skill in the art.

Types of MVA pathway polypeptides and/or DXP pathway polypeptides which can be used and methods of making microorganisms (e.g., facultative anaerobes such as E. coli) encoding MVA pathway polypeptides and/or DXP pathway polypeptides are also described in International Patent Application Publication Nos. WO2009/076676, WO2010/003007, WO 2009/132220, WO 2010/031062, WO2010/031068, WO 2010/031076, WO2010/031077, WO2010/031079, WO2010/148150, WO2010/005525, WO 2010/078457, WO2010/124146, WO2010/148144, WO2010/148256 and U.S. patent application Ser. Nos. 12/496,573, 12/560,390, 12/560,317, 12/560,370, 12/560,305, and 12/560,366.

One of skill in the art can readily select and/or use suitable promoters to optimize the expression of isoprene synthase or and one or more MVA pathway polypeptides and/or one or more DXP pathway polypeptides in anaerobes. Similarly, one of skill in the art can readily select and/or use suitable vectors (or transfer vehicle) to optimize the expression of isoprene synthase or and one or more MVA pathway polypeptides and/or one or more DXP pathway polypeptides in anaerobes. In some embodiments, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some embodiments, an isoprene synthase or MVA pathway nucleic acid integrates into a chromosome of the cells without a selective marker.

In some embodiments, the vector is a shuttle vector, which is capable of propagating in two or more different host species. Exemplary shuttle vectors are able to replicate in E. coli and/or Bacillus subtilis and in an obligate anaerobe, such as Clostridium. Upon insertion of an isoprene synthase or MVA pathway nucleic acid into the shuttle vector using techniques well known in the art, the shuttle vector can be introduced into an E. coli host cell for amplification and selection of the vector. The vector can then be isolated and introduced into an obligate anaerobic cell for expression of the isoprene synthase or MVA pathway polypeptide.

Exemplary IDI Polypeptides and Nucleic Acids

Isopentenyl diphosphate isomerase polypeptides (isopentenyl-diphosphate delta-isomerase or IDI) catalyses the interconversion of isopentenyl diphosphate (IPP) and dimethyl allyl diphosphate (DMAPP) (e.g., converting IPP into DMAPP and/or converting DMAPP into IPP). While not intending to be bound by any particular theory, it is believed that increasing the amount of IDI polypeptide in cells increases the amount (and conversion rate) of IPP that is converted into DMAPP, which in turn is converted into isoprene. Exemplary IDI polypeptides include polypeptides, fragments of polypeptides, peptides, and fusions polypeptides that have at least one activity of an IDI polypeptide. Standard methods can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Source Organisms

Isoprene synthase and/or MVA pathway nucleic acids (and their encoded polypeptides) and/or DXP pathway nucleic acids (and their encoded polypeptides) can be obtained from any organism that naturally contains isoprene synthase and/or MVA pathway nucleic acids and/or DXP pathway nucleic acids. As noted above, isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. DXP pathway nucleic acids can be obtained, e.g., from any organism that contains the DXP pathway.

Exemplary sources for isoprene synthases, MVA pathway polypeptides and/or DXP pathway polypeptides and other polypeptides (including nucleic acids encoding any of the polypeptides described herein) which can be used are also described in International Patent Application Publication Nos. WO2009/076676, WO2010/003007, WO 2009/132220, WO 2010/031062, WO2010/031068, WO 2010/031076, WO2010/031077, WO2010/031079, WO2010/148150, WO2010/005525, WO 2010/078457, WO2010/124146, WO2010/148144, WO2010/148256 and U.S. patent application Ser. Nos. 12/496,573, 12/560,390, 12/560,317, 12/560,370, 12/560,305, and 12/560,366.

Host Cells

Various types of host cells can be used to produce isoprene as part of a bioisoprene composition. In some embodiments, the host cell is a yeast, such as *Saccharomyces* sp., *Schizosaccharomyces* sp., *Pichia* sp., or *Candida* sp.

In some embodiments, the host cell is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of *Archaea* such as *Methanosarcina mazei*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the host cell is a gram-positive bacterium. Non-limiting examples include strains of *Streptomyces* (e.g., *S. lividans*, *S. coelicolor*, or *S. griseus*) and *Bacillus*. In some embodiments, the source organism is a gram-negative bacterium, such as *E. coli* or *Pseudomonas* sp.

In some embodiments, the host cell is a plant, such as a plant from the family Fabaceae, such as the Faboideae subfamily. In some embodiments, the source organism is kudzu, poplar (such as *Populus albaxtremula* CAC35696), aspen (such as *Populus tremuloides*), or *Quercus robur*.

In some embodiments, the host cell is an algae, such as a green algae, red algae, glaucophytes, chlorarachniophytes, euglenids, chromista, or dinoflagellates.

In some embodiments, the host cell is a cyanobacteria, such as cyanobacteria classified into any of the following groups based on morphology: Chroococcales, Pleurocapsales, Oscillatoriales, Nostocales, or Stigonematales.

In some embodiments, the host cell is an anaerobic organisms. These organisms can include, but are not limited to, obligate anaerobes, facultative anaerobes, and aerotolerant anaerobes. Such organisms can be any of the organisms listed above, bacteria, yeast, etc. In one embodiment, the obligate anaerobes can be any one or combination selected from the group consisting of *Clostridium ljungdahlii, Clostridium autoethanogenum, Eurobacterium limosum, Clostridium carboxydivorans, Peptostreptococcus productus*, and *Butyribacterium methylotrophicum*. In other aspects, the host cell can be *Clostridium aceticum, Clostridium acetobutylicum, Moorella thermoacetica, Rhodospirillum rubrum, Desulfitobacterium hafniense, Aecetoanaerobium notera, Thermoanaerobacter kivui*, or *Acetobacterium woodi*.

In some embodiments, the cells are *Clostridium* cells. In some embodiments, the cells are selected from the group consisting of *Clostridium ljungdahlii, Clostridium aceticum, Clostridium acetobutylicum, Clostridium carboxidivorans*, and *Clostridium autoethanogenum*. In some embodiments, the cells are *acetobacterium* cells. In some embodiments, the cells are *Acetobacterium woodii*. In some embodiments, cells are acetogen cells. In some embodiments, the acetogens are selected from the group consisting of *Clostridium ljungdahlii, Clostridium aceticum, Moorella thermoacetica, Rhodospirillum rubrum, Desulfitobacterium hafniense, Clostridium carboxidivorans, Aecetoanaerobium notera, Butyribacterium methylotrophicum, Thermoanaerobacter kivui, Eubacterium limosum, Peptostreptococcus productus, Desulfococcus oleovorans, Syntrophobacter fumaroxidans*, delta proteobacterium MLMS-1, *Treponema primitia* ZAS-1, *Treponema primitia* ZAS-2, *Carboxydothermus hydrogenoformans, Sporomsa termitida, Clostridium difficile, Alkaliphilus metalliredigens*, and *Acetobacterium woodi*.

In some embodiments, the host cell is a photosynthetic cell. In other embodiments, the host cell is a non-photosynthetic cell.

Transformation Methods

Nucleic acids encoding isoprene synthase and/or MVA pathway polypeptides and/or DXP pathway polypeptides can be inserted into any host cell using standard techniques for expression of the encoded isoprene synthase and/or MVA pathway polypeptide. General transformation techniques are known in the art (see, e.g., Current Protocols in Molecular Biology (F. M. Ausubel et al. (eds) Chapter 9, 1987; Sambrook et al., Molecular Cloning: A Laboratory Manual, $2^{nd}$ ed., Cold Spring Harbor, 1989; and Campbell et al., Curr. Genet. 16:53-56, 1989 or "Handbook on Clostridia" (P. Durre, ed., 2004). For obligate anaerobic host cells, such as *Clostridium*, electroporation, as described by Davis et al., 2005 and in Examples III and IV, can be used as an effective technique. The introduced nucleic acids may be integrated into chromosomal DNA or maintained as extrachromosomal replicating sequences.

Techniques for producing isoprene in cultures of cells that produce isoprene are described in WO2009/076676, WO2010/003007, WO 2009/132220, WO 2010/031062, WO2010/031068, WO 2010/031076, WO2010/031077, WO2010/031079, WO2010/148150, WO2010/005525, WO 2010/078457, WO2010/124146, WO2010/148144, WO2010/148256 and U.S. patent application Ser. Nos. 12/496,573, 12/560,390, 12/560,317, 12/560,370, 12/560,305, and 12/560,366, the teachings of which are incorporated herein by reference for the purpose of teaching techniques for producing and recovering isoprene by such a process. In any case, WO 2009/076676, WO 2010/003007, WO 2010/031079, WO 2010/031062, WO 2010/031077, WO 2010/031068, WO 2010/031076, WO 2010/078457, US 2009/0203102 A1 and US 2010/0003716 A1 teach compositions and methods for the production of increased amounts of isoprene in cell cultures. U.S. Patent Publication No. 2009/

0203102 and U.S. Patent Publication No. 2010/0196977 further teach compositions and methods for co-production of isoprene and hydrogen from cultured cells. In particular, these compositions and methods compositions and methods increase the rate of isoprene production and increase the total amount of isoprene that is produced.

As discussed above, the amount of isoprene produced by cells can be greatly increased by introducing a heterologous nucleic acid encoding an isoprene synthase polypeptide (e.g., a plant isoprene synthase polypeptide) into the cells. Isoprene synthase polypeptides convert dimethyl allyl diphosphate (DMAPP) into isoprene.

Additionally, isoprene production by cells that contain a heterologous isoprene synthase nucleic acid can be enhanced by increasing the amount of a 1-deoxy-D-xylulose-5-phosphate synthase (DXS) polypeptide and/or an isopentenyl diphosphate isomerase (IDI) polypeptide expressed by the cells.

Iron-sulfur cluster-interacting redox polypeptide can also be used to increase the activity demonstrated by the DXP pathway polypeptides (such as HDS (GcpE or IspG) or HDR polypeptide (IspH or LytB). While not intending to be bound to a particular theory, the increased expression of one or more endogenous or heterologous iron-sulfur interacting redox nucleic acids or polypeptides improve the rate of formation and the amount of DXP pathway polypeptides containing an iron sulfur cluster (such as HDS or HDR), and/or stabilize DXP pathway polypeptides containing an iron sulfur cluster (such as HDS or HDR). This in turn increases the carbon flux to isoprene synthesis in cells by increasing the synthesis of HMBPP and/or DMAPP and decreasing the cMEPP and HMBPP pools in the DXP pathway.

Growth Conditions

The cells (e.g., aerobic or anaerobic) of any of the compositions or methods should be grown under conditions that are conducive to optimal production of isoprene. Considerations for optimization include cell culture media, oxygen levels, and conditions favorable for decoupling such that isoprene production is favored over cell growth (see, e.g., WO 2010/003007, which is incorporated herein for teaching of optimization include cell culture media, oxygen levels, and conditions favorable for decoupling). For aerobic cells, the cell culture conditions should be used that provide optimal oxygenation for cells to be able to produce isoprene.

Consideration should be paid to safety precautions for flammability, such as culturing under oxygen ranges that minimize flammability of the system. The production of isoprene within safe operating levels according to its flammability characteristics simplifies the design and construction of commercial facilities, vastly improves the ability to operate safely, and limits the potential for fires to occur. The flammability envelope is characterized by the lower flammability limit (LFL), the upper flammability limit (UFL), the limiting oxygen concentration (LOC), and the limiting temperature. For a system to be flammable, a minimum amount of fuel (such as isoprene) must be in the presence of a minimum amount of oxidant, typically oxygen. The LFL is the minimum amount of isoprene that must be present to sustain burning, while the UFL is the maximum amount of isoprene that can be present. Above this limit, the mixture is fuel rich and the fraction of oxygen is too low to have a flammable mixture. The LOC indicates the minimum fraction of oxygen that must also be present to have a flammable mixture. The limiting temperature is based on the flash point of isoprene and is that lowest temperature at which combustion of isoprene can propagate. These limits are specific to the concentration of isoprene, type and concentration of oxidant, inerts present in the system, temperature, and pressure of the system. Compositions that fall within the limits of the flammability envelope propagate combustion and require additional safety precautions in both the design and operation of process equipment. In particular, the optimal ranges for the production of isoprene are within the safe zone, i.e., the nonflammable range of isoprene concentrations. In one such aspect, the invention features a method for the production of isoprene within the nonflammable range of isoprene concentrations (outside the flammability envelope of isoprene). See, for example, WO 2010/003007, which is incorporated herein for teaching of flammability ranges.

In one embodiment, for an isoprene, $O_2$, $N_2$, and $CO_2$ mixture at 40° C. and 1 atmosphere, the LOC was determined to be 9.5 vol %. The addition of up to 30% $CO_2$ did not significantly affect the flammability characteristics of an isoprene, $O_2$, and $N_2$ mixture. Only slight variations in flammability characteristics were shown between a dry and water saturated isoprene, $O_2$, and $N_2$ system. The limiting temperature is about −54° C. Temperatures below about −54° C. are too low to propagate combustion of isoprene.

In some embodiments, the LFL of isoprene ranges from about 1.5 vol. % to about 2.0 vol %, and the UFL of isoprene ranges from about 2.0 vol. % to about 12.0 vol. %, depending on the amount of oxygen in the system. In some embodiments, the LOC is about 9.5 vol % oxygen. In some embodiments, the LFL of isoprene is between about 1.5 vol. % to about 2.0 vol %, the UFL of isoprene is between about 2.0 vol. % to about 12.0 vol. %, and the LOC is about 9.5 vol % oxygen when the temperature is between about 25° C. to about 55° C. (such as about 40° C.) and the pressure is between about 1 atmosphere and 3 atmospheres.

In some embodiments, isoprene is produced in the presence of less than about 9.5 vol % oxygen (that is, below the LOC required to have a flammable mixture of isoprene). In some embodiments in which isoprene is produced in the presence of greater than or about 9.5 vol % oxygen, the isoprene concentration is below the LFL (such as below about 1.5 vol. %). For example, the amount of isoprene can be kept below the LFL by diluting the isoprene composition with an inert gas (e.g., by continuously or periodically adding an inert gas such as nitrogen to keep the isoprene composition below the LFL). In some embodiments in which isoprene is produced in the presence of greater than or about 9.5 vol % oxygen, the isoprene concentration is above the UFL (such as above about 12 vol. %). For example, the amount of isoprene can be kept above the UFL by using a system (such as any of the cell culture systems described herein) that produces isoprene at a concentration above the UFL. If desired, a relatively low level of oxygen can be used so that the UFL is also relatively low. In this case, a lower isoprene concentration is needed to remain above the UFL.

In some embodiments in which isoprene is produced in the presence of greater than or about 9.5 vol % oxygen, the isoprene concentration is within the flammability envelope (such as between the LFL and the UFL). In some embodiments when the isoprene concentration may fall within the flammability envelope, one or more steps are performed to reduce the probability of a fire or explosion. For example, one or more sources of ignition (such as any materials that may generate a spark) can be avoided. In some embodiments, one or more steps are performed to reduce the amount of time that the concentration of isoprene remains within the flammability envelope. In some embodiments, a sensor is used to detect when the concentration of isoprene is close to or within the flammability envelope. If desired, the concentration of isoprene can be measured at one or more time points during the culturing of cells, and the cell culture conditions and/or the amount of inert gas can be adjusted using standard methods if the concentration of isoprene is close to or within the flammability envelope. In particular embodiments, the cell culture conditions (such as fermentation conditions) are adjusted to either decrease the concentration of isoprene below the LFL or increase the concentration of isoprene above the UFL. In some embodiments, the amount of isoprene is kept below the LFL by diluting the isoprene composition with an inert gas (such as by continuously or periodically adding an inert gas to keep the isoprene composition below the LFL).

In some embodiments, the amount of flammable volatiles other than isoprene (such as one or more sugars) is at least about 2, 5, 10, 50, 75, or 100-fold less than the amount of isoprene produced. In some embodiments, the portion of the gas phase other than isoprene gas comprises between about 0% to about 100% (volume) oxygen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 100% (volume) oxygen. In some embodiments, the portion of the gas phase other than isoprene gas comprises between about 0% to about 99% (volume) nitrogen, such as between about 0% to about 10%, about 10% to about 20%, about 20% to about 30%, about 30% to about 40%, about 40% to about 50%, about 50% to about 60%, about 60% to about 70%, about 70% to about 80%, about 90% to about 90%, or about 90% to about 99% (volume) nitrogen.

In some embodiments, the portion of the gas phase other than isoprene gas comprises between about 1% to about 50% (volume) $CO_2$, such as between about 1% to about 10%, about 10% to about 20%, about 20% to about 30%, about 30% to about 40%, or about 40% to about 50% (volume) $CO_2$.

In some embodiments, an isoprene composition also contains ethanol. For example, ethanol may be used for extractive distillation of isoprene, resulting in compositions (such as intermediate product streams) that include both ethanol and isoprene. Desirably, the amount of ethanol is outside the flammability envelope for ethanol. The LOC of ethanol is about 8.7 vol %, and the LFL for ethanol is about 3.3 vol % at standard conditions, such as about 1 atmosphere and about 60° F. (NFPA 69 *Standard on Explosion Prevention Systems*, 2008 edition, which is hereby incorporated by reference in its entirety, particularly with respect to LOC, LFL, and UFL values). In some embodiments, compositions that include isoprene and ethanol are produced in the presence of less than the LOC required to have a flammable mixture of ethanol (such as less than about 8.7% vol %). In some embodiments in which compositions that include isoprene and ethanol are produced in the presence of greater than or about the LOC required to have a flammable mixture of ethanol, the ethanol concentration is below the LFL (such as less than about 3.3 vol. %).

In various embodiments, the amount of oxidant (such as oxygen) is below the LOC of any fuel in the system (such as isoprene or ethanol). In various embodiments, the amount of oxidant (such as oxygen) is less than about 60, 40, 30, 20, 10, or 5% of the LOC of isoprene or ethanol. In various embodiments, the amount of oxidant (such as oxygen) is less than the LOC of isoprene or ethanol by at least 2, 4, 5, or more absolute percentage points (vol %). In particular embodiments, the amount of oxygen is at least 2 absolute percentage points (vol %) less than the LOC of isoprene or ethanol (such as an oxygen concentration of less than 7.5 vol % when the LOC of isoprene is 9.5 vol %). In various embodiments, the amount of fuel (such as isoprene or ethanol) is less than or about 25, 20, 15, 10, or 5% of the LFL for that fuel.

For facultative anaerobic cells, these cells are capable of replicating and/or producing isoprene in a fermentation system that is substantially free of oxygen.

Renewable resources are used for production of isoprene. Renewable resources refer to resources that are not fossil fuels. Generally, renewable resources are derived from living organisms or recently living organisms that can be replenished as they are consumed. Renewable resources can be replaced by natural ecological cycles or sound management practices. Non-limiting examples include biomass (e.g., switchgrass, hemp, corn, poplar, willow, sorghum, sugarcane), trees, and other plants. Non-limiting examples of renewable resources (or renewable carbon sources) include cheese whey permeate, cornsteep liquor, sugar beet molasses, barley malt, and components from any of the foregoing. Exemplary renewable carbon sources also include glucose, hexose, pentose and xylose present in biomass, such as corn, switchgrass, sugar cane, cell waste of fermentation processes, and protein by-product from the milling of soy, corn, or wheat. In some embodiments, the biomass carbon source is a lignocellulosic, hemicellulosic, or cellulosic material such as, but are not limited to, a grass, wheat, wheat straw, bagasse, sugar cane bagasse, soft wood pulp, corn, corn cob or husk, corn kernel, fiber from corn kernels, corn stover, switch grass, rice hull product, or a by-product from wet or dry milling of grains (e.g., corn, sorghum, rye, triticate, barley, wheat, and/or distillers grains). Exemplary cellulosic materials include wood, paper and pulp waste, herbaceous plants, and fruit pulp. In some embodiments, the carbon source includes any plant part, such as stems, grains, roots, or tubers. In some embodiments, all or part of any of the following plants are used as a carbon source: corn, wheat, rye, sorghum, triticate, rice, millet, barley, cassava, legumes, such as beans and peas, potatoes, sweet potatoes, bananas, sugarcane, and/or tapioca. In some embodiments, the carbon source is a biomass hydrolysate, such as a biomass hydrolysate that includes both xylose and glucose or that includes both sucrose and glucose.

Examples of other fermentation systems and culture conditions which can be used are described in WO2009/076676, WO2010/003007, WO 2009/132220, WO 2010/031062, WO2010/031068, WO 2010/031076, WO2010/031077, WO2010/031079, WO2010/148150, WO2010/005525, WO 2010/078457, WO2010/124146, WO2010/148144, WO2010/148256 and U.S. patent application Ser. Nos. 12/496,573, 12/560,390, 12/560,317, 12/560,370, 12/560, 305, and 12/560,366.

Bioreactors

A variety of different types of reactors can be used for production of isoprene from any renewable resource. There are a large number of different types of fermentation processes that are used commercially. The bioreactor can be designed to optimize the retention time of the cells, the residence time of liquid, and the sparging rate of any gas (e.g., syngas).

In various embodiments, the cells are grown using any known mode of fermentation, such as batch, fed-batch, continuous, or continuous with recycle processes. In some embodiments, a batch method of fermentation is used. Classical batch fermentation is a closed system where the composition of the media is set at the beginning of the fermentation and is not subject to artificial alterations during the fermentation. Thus, at the beginning of the fermentation the cell medium is inoculated with the desired host cells and fermentation is permitted to occur adding nothing to the system. Typically, however, "batch" fermentation is batch with respect to the addition of carbon source and attempts are often made at controlling factors such as pH and oxygen concentration. In batch systems, the metabolite and biomass compositions of the system change constantly until the time the fermentation is stopped. Within batch cultures, cells moderate through a static lag phase to a high growth log phase and finally to a stationary phase where growth rate is diminished or halted. In some embodiments, cells in log phase are responsible for the bulk of the isoprene production. In some embodiments, cells in stationary phase produce isoprene.

In some embodiments, a variation on the standard batch system is used, such as the Fed-Batch system. Fed-Batch fermentation processes comprise a typical batch system with the exception that the carbon source (e.g. syngas, glucose) is added in increments as the fermentation progresses. Fed-Batch systems are useful when catabolite repression is apt to inhibit the metabolism of the cells and where it is desirable to have limited amounts of carbon source in the cell medium. Fed-batch fermentations may be performed with the carbon source (e.g., syngas, glucose, fructose) in a limited or excess amount. Measurement of the actual carbon source concentration in Fed-Batch systems is difficult and is therefore estimated on the basis of the changes of measurable factors such as pH, dissolved oxygen, and the partial pressure of waste gases such as $CO_2$. Batch and Fed-Batch fermentations are common and well known in the art and examples may be found in Brock, Biotechnology: A Textbook of Industrial Microbiology, Second Edition (1989) Sinauer Associates, Inc.

In some embodiments, continuous fermentation methods are used. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth or isoprene production. For example, one method maintains a limiting nutrient such as the carbon source or nitrogen level at a fixed rate and allows all other parameters to moderate. In other systems, a number of factors affecting growth can be altered continuously while the cell concentration (e.g., the concentration measured by media turbidity) is kept constant. Continuous systems strive to maintain steady state growth conditions. Thus, the cell loss due to media being drawn off is balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, Biotechnology: A Textbook of Industrial Microbiology, Second Edition (1989) Sinauer Associates, Inc., which is hereby incorporated by reference in its entirety, particularly with respect to cell culture and fermentation conditions.

A variation of the continuous fermentation method is the continuous with recycle method. This system is similar to the continuous bioreactor, with the difference being that cells removed with the liquid content are returned to the bioreactor by means of a cell mass separation device. Cross-filtration units, centrifuges, settling tanks, wood chips, hydrogels, and/or hollow fibers are used for cell mass separation or retention. This process is typically used to increase the productivity of the continuous bioreactor system, and may be particularly useful for anaerobes, which may grow more slowly and in lower concentrations than aerobes.

In one embodiment, a membrane bioreactor can be used for the growth and/or fermentation of the cells described herein, in particular, if the cells are expected to grow slowly. A membrane filter, such as a crossflow filter or a tangential flow filter, can be operated jointly with a liquid fermentation bioreactor that produces isoprene gas. Such a membrane bioreactor can enhance fermentative production of isoprene gas by combining fermentation with recycling of select broth components that would otherwise be discarded. The MBR filters fermentation broth and returns the non-permeating component (filter "retentate") to the reactor, effectively increasing reactor concentration of cells, cell debris, and other broth solids, while maintaining specific productivity of the cells. This substantially improves titer, total production, and volumetric productivity of isoprene, leading to lower capital and operating costs. See, for example, PCT/US2010/0161913, which is incorporated by reference in its entirety, particularly for its teaching on various parameters for improving isoprene production by recycling retentate.

The liquid filtrate (or permeate) is not returned to the reactor and thus provides a beneficial reduction in reactor volume, similar to collecting a broth draw-off. However, unlike a broth draw-off, the collected permeate is a clarified liquid that can be easily sterilized by filtration after storage in an ordinary vessel. Thus, the permeate can be readily reused as a nutrient and/or water recycle source. A permeate, which contains soluble spent medium, may be added to the same or another fermentation to enhance isoprene production.

Exemplary Production of Bioisoprene Composition

In some embodiments, the cells are cultured in a culture medium under conditions permitting the production of isoprene by the cells.

By "peak absolute productivity" is meant the maximum absolute amount of isoprene in the off-gas during the culturing of cells for a particular period of time (e.g., the culturing of cells during a particular fermentation run). By "peak absolute productivity time point" is meant the time point during a fermentation run when the absolute amount of isoprene in the off-gas is at a maximum during the culturing of cells for a particular period of time (e.g., the culturing of cells during a particular fermentation run). In some embodiments, the isoprene amount is measured at the peak absolute productivity time point. In some embodiments, the peak absolute productivity for the cells is about any of the isoprene amounts disclosed herein.

By "peak specific productivity" is meant the maximum amount of isoprene produced per cell during the culturing of cells for a particular period of time (e.g., the culturing of cells during a particular fermentation run). By "peak specific productivity time point" is meant the time point during the culturing of cells for a particular period of time (e.g., the culturing of cells during a particular fermentation run) when the amount of isoprene produced per cell is at a maximum. The peak specific productivity is determined by dividing the total productivity by the amount of cells, as determined by optical density at 600 nm ($OD_{600}$). In some embodiments, the isoprene amount is measured at the peak specific productivity time point. In some embodiments, the peak specific productivity for the cells is about any of the isoprene amounts per cell disclosed herein.

By "peak volumetric productivity" is meant the maximum amount of isoprene produced per volume of broth (including the volume of the cells and the cell medium) during the culturing of cells for a particular period of time (e.g., the culturing of cells during a particular fermentation run). By "peak specific volumetric productivity time point" is meant the time point during the culturing of cells for a particular period of time (e.g., the culturing of cells during a particular fermentation run) when the amount of isoprene produced per volume of broth is at a maximum. The peak specific volumetric productivity is determined by dividing the total productivity by the volume of broth and amount of time. In some embodiments, the isoprene amount is measured at the peak specific volumetric productivity time point. In some embodiments, the peak specific volumetric productivity for the cells is about any of the isoprene amounts per volume per time disclosed herein.

By "peak concentration" is meant the maximum amount of isoprene produced during the culturing of cells for a particular period of time (e.g., the culturing of cells during a particular fermentation run). By "peak concentration time point" is meant the time point during the culturing of cells for a particular period of time (e.g., the culturing of cells during a particular fermentation run) when the amount of isoprene produced per cell is at a maximum. In some embodiments, the isoprene amount is measured at the peak concentration time point. In some embodiments, the peak concentration for the cells is about any of the isoprene amounts disclosed herein.

By "average volumetric productivity" is meant the average amount of isoprene produced per volume of cell broth (including the volume of the cells and the cell medium) during the culturing of cells for a particular period of time (e.g., the culturing of cells during a particular fermentation run). The average volumetric productivity is determined by dividing the total productivity by the volume of broth and amount of time. In some embodiments, the average specific volumetric productivity for the cells is about any of the isoprene amounts per volume per time disclosed herein.

By "cumulative total productivity" is meant the cumulative, total amount of isoprene produced during the culturing of cells for a particular period of time (e.g., the culturing of cells during a particular fermentation run). In some embodiments, the cumulative, total amount of isoprene is measured. In some embodiments, the cumulative total productivity for the cells is about any of the isoprene amounts disclosed herein.

As used herein, "relative detector response" refers to the ratio of the detector response (such as the peak area in a GC/MS chromatogram) for one compound (such as isoprene) to the detector response (such as the peak area in a GC/MS chromatogram) of one or more compounds (such as all C5 hydrocarbons). The detector response may be measured as described herein, such as the GC/MS analysis performed with an Agilent 6890 GC/MS system fitted with an Agilent HP-5MS GC column (30 m×250 µm; 0.25 µm film thickness). If desired, the relative detector response can be converted to a weight percentage using the response factors for each of the compounds. This response factor is a measure of how much signal is generated for a given amount of a particular compound (that is, how sensitive the detector is to a particular compound). This response factor can be used as a correction factor to convert the relative detector response to a weight percentage when the detector has different sensitivities to the compounds being compared. Alternatively, the weight percentage can be approximated by assuming that the response factors are the same for the compounds being compared. Thus, the weight percentage can be assumed to be approximately the same as the relative detector response.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 12,500, 20,000, 30,000, 40,000, 50,000, 75,000, 100,000, 125,000, 150,000, 188,000, or more nmole of isoprene/gram of cells for the wet weight of the cells/hour (nmole/$g_{wcm}$/hr). In some embodiments, the amount of isoprene is between about 2 to about 200,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr, about 5,000 to about 10,000 nmole/$g_{wcm}$/hr, about 10,000 to about 50,000 nmole/$g_{wcm}$/hr, about 50,000 to about 100,000 nmole/$g_{wcm}$/hr, about 100,000 to about 150,000 nmole/$g_{wcm}$/hr, or about 150,000 to about 200,000 nmole/$g_{wcm}$/hr. In some embodiments, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr, about 1,000 to about 5,000 nmole/$g_{wcm}$/hr, about 2,000 to about 20,000 nmole/$g_{wcm}$/hr, about 5,000 to about 50,000 nmole/$g_{wcm}$/hr, about 10,000 to about 100,000 nmole/$g_{wcm}$/hr, about 20,000 to about 150,000 nmole/$g_{wcm}$/hr, about 20,000 to about 200,000 nmole/$g_{wcm}$/hr, about 50,000 to about 500,000 nmole/$g_{wcm}$/hr, or about 100,000 to about 1,000,000 nmole/$g_{wcm}$/hr.

The amount of isoprene in units of nmole/$g_{wcm}$/hr can be measured as disclosed in U.S. Pat. No. 5,849,970, which is hereby incorporated by reference in its entirety, particularly with respect to the measurement of isoprene production. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, for example, Greenberg et al, *Atmos. Environ.* 27A:2689-2692, 1993; Silver et al., *Plant Physiol.* 97:1588-1591, 1991, which are each hereby incorporated by reference in their entireties, particularly with respect to the measurement of isoprene production). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

Exemplary Isoprene Compositions as Starting Material for Chemical Transformation to Fuel Constituents Starting compositions of isoprene are used as a starting point for making fuel constituents. It is important to use a commercially beneficial amount of highly pure isoprene as a starting point for efficiency. In one aspect, a commercially beneficial amount of highly pure isoprene is found in a bioisoprene composition. In some embodiments, the bioisoprene composition has greater than or about 2, 5, 10, 20, 30, 40, 50, 60, 70, 80, 90, 100, 200, 300, 400, 500, 600, 700, 800, 900, or 1000 mg of isoprene. In some embodiments, the bioisoprene composition has greater than or about 1, 10, 100, 1000, 10,000, 100,000, 1,000,000 Kg or more of isoprene. In some embodiments, greater than or about 20, 25, 30, 40, 50, 60, 70, 80, 90, or 95% (w/w) of the volatile organic fraction of the starting composition is isoprene.

In some embodiments, the bioisoprene composition has greater than or about 98.0, 98.5, 99.0, 99.5, or 100% isoprene by weight compared to the total weight of all C5 hydrocarbons in the starting composition. In some embodiments, the bioisoprene composition has greater than or about 99.90, 99.92, 99.94, 99.96, 99.98, or 100% isoprene by weight compared to the total weight of all C5 hydrocarbons in the starting composition. In some embodiments, the starting composition has a relative detector response of greater than or about 98.0, 98.5, 99.0, 99.5, or 100% for isoprene compared to the detector response for all C5 hydrocarbons in the starting composition. In some embodiments, the starting composition has a relative detector response of greater than or about 99.90, 99.91, 99.92, 99.93, 99.94, 99.95, 99.96, 99.97, 99.98, 99.99, or 100% for isoprene compared to the detector response for all C5 hydrocarbons in the starting composition. In some embodiments, the starting bioisoprene composition comprises between about 98.0 to about 98.5, about 98.5 to about 99.0, about 99.0 to about 99.5, about 99.5 to about 99.8, about 99.8 to 100% isoprene by weight compared to the total weight of all C5 hydrocarbons in the starting composition. In some embodiments, the starting bioisoprene composition comprises between about 99.90 to about 99.92, about 99.92 to about 99.94, about 99.94 to about 99.96, about 99.96 to about 99.98, about 99.98 to 100% isoprene by weight compared to the total weight of all C5 hydrocarbons in the starting composition.

In some embodiments, the bioisoprene composition comprises less than or about 2.0, 1.5, 1.0, 0.5, 0.2, 0.12, 0.10, 0.08, 0.06, 0.04, 0.02, 0.01, 0.005, 0.001, 0.0005, 0.0001, 0.00005, or 0.00001% C5 hydrocarbons other than isoprene (such 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne) by weight compared to the total weight of all C5 hydrocarbons in the starting composition. In some embodiments, the starting composition has a relative detector response of less than or about 2.0, 1.5, 1.0, 0.5, 0.2, 0.12, 0.10, 0.08, 0.06, 0.04, 0.02, 0.01, 0.005, 0.001, 0.0005, 0.0001, 0.00005, or 0.00001% for C5 hydrocarbons other than isoprene compared to the detector response for all C5 hydrocarbons in the starting composition. In some embodiments, the starting composition has a relative detector response of less than or about 2.0, 1.5, 1.0, 0.5, 0.2, 0.12, 0.10, 0.08, 0.06, 0.04, 0.02, 0.01, 0.005, 0.001, 0.0005, 0.0001, 0.00005, or 0.00001% for 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne compared to the detector response for all C5 hydrocarbons in the starting composition. In some embodiments, the starting bioisoprene composition comprises between about 0.02 to about 0.04%, about 0.04 to about 0.06%, about 0.06 to 0.08%, about 0.08 to 0.10%, or about 0.10 to about 0.12% C5 hydrocarbons other than isoprene (such 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne) by weight compared to the total weight of all C5 hydrocarbons in the starting composition.

In some embodiments, the starting bioisoprene composition comprises less than or about 50, 40, 30, 20, 10, 5, 1, 0.5, 0.1, 0.05, 0.01, or 0.005 µg/L of a hydrocarbon other than isoprene (such 1,3-cyclopentadiene, cis-1,3-pentadiene, trans-1,3-pentadiene, 1,4-pentadiene, 1-pentyne, 2-pentyne, 1-pentene, 2-methyl-1-butene, 3-methyl-1-butyne, pent-4-ene-1-yne, trans-pent-3-ene-1-yne, or cis-pent-3-ene-1-yne). In some embodiments, the starting bioisoprene composition comprises between about 0.005 to about 50, such as about 0.01 to about 10, about 0.01 to about 5, about 0.01 to about 1, about 0.01 to about 0.5, or about 0.01 to about 0.005 µg/L of a hydrocarbon other than isoprene. In some embodiments, the starting bioisoprene composition comprises less than or about 50, 40, 30, 20, 10, 5, 1, 0.5, 0.1, 0.05, 0.01, or 0.005 µg/L of a protein or fatty acid (such as a protein or fatty acid that is naturally associated with natural rubber).

In some embodiments, the starting bioisoprene composition comprises less than or about 10, 5, 1, 0.8, 0.5, 0.1, 0.05, 0.01, or 0.005 ppm of alpha acetylenes, piperylenes, acetonitrile, or 1,3-cyclopentadiene. In some embodiments, the starting bioisoprene composition comprises less than or about 5, 1, 0.5, 0.1, 0.05, 0.01, or 0.005 ppm of sulfur or allenes. In some embodiments, the starting bioisoprene composition comprises less than or about 30, 20, 15, 10, 5, 1, 0.5, 0.1, 0.05, 0.01, or 0.005 ppm of all acetylenes (such as 1-pentyne, 2-pentyne, 3-methyl-1-butyne, pent-4-ene-1-yne, trans-pent-3-ene-1-yne, and cis-pent-3-ene-1-yne). In some embodiments, the starting bioisoprene composition comprises less than or about 2000, 1000, 500, 200, 100, 50, 40, 30, 20, 10, 5, 1, 0.5, 0.1, 0.05, 0.01, or 0.005 ppm of isoprene dimers, such as cyclic isoprene dimers (e.g., cyclic C10 compounds derived from the dimerization of two isoprene units).

In some embodiments, the starting bioisoprene composition comprises ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), or any two or more of the foregoing. In particular embodiments, the starting bioisoprene composition comprises greater than or about 0.005, 0.01, 0.05, 0.1, 0.5, 1, 5, 10, 20, 30, 40, 60, 80, 100, or 120 µg/L of ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol (such as 3-methyl-3-buten-1-ol or 3-methyl-2-buten-1-ol), or any two or more of the foregoing. In some embodiments, the bioisoprene composition comprises between about 0.005 to about 120, such as about 0.01 to about 80, about 0.01 to about 60, about 0.01 to about 40, about 0.01 to about 30, about 0.01 to about 20, about 0.01 to about 10, about 0.1 to about 80, about 0.1 to about 60, about 0.1 to about 40, about 5 to about 80, about 5 to about 60, or about 5 to about 40 µg/L of ethanol, acetone, methanol, acetaldehyde, methacrolein, methyl vinyl ketone, 3-methylfuran, 2-methyl-2-vinyloxirane, cis- and trans-3-methyl-1,3-pentadiene, a C5 prenyl alcohol, or any two or more of the foregoing.

In some embodiments, the starting bioisoprene composition includes one or more of the following components: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, 3-hexen-1-ol, 3-hexen-1-yl acetate, limonene, geraniol (trans-3,7-dimethyl-2,6-octadien-1-ol), citronellol (3,7-dimethyl-6-octen-1-ol), (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). In various embodiments, the amount of one of these components relative to amount of isoprene in units of percentage by weight (i.e., weight of the component divided by the weight of isoprene times 100) is greater than or about 0.01, 0.02, 0.05, 0.1, 0.5, 1, 5, 10, 20, 30, 40, 50, 60, 70, 80, 90, 100, or 110% (w/w). In some embodiments, the relative detector response for the second compound compared to the detector response for isoprene is greater than or about 0.01, 0.02, 0.05, 0.1, 0.5, 1, 5, 10, 20, 30, 40, 50, 60, 70, 80, 90, 100, or 110%. In various embodiments, the amount of one of these components relative to amount of isoprene in units of percentage by weight (i.e., weight of the component divided by the weight of isoprene times 100) is between about 0.01 to about 105% (w/w), such as about 0.01 to about 90, about 0.01 to about 80, about 0.01 to about 50, about 0.01 to about 20, about 0.01 to about 10, about 0.02 to about 50, about 0.05 to about 50, about 0.1 to about 50, or 0.1 to about 20% (w/w).

In some embodiments, at least a portion of the starting bioisoprene composition is in a gas phase. In some embodiments, at least a portion of the starting bioisoprene composition is in a liquid phase (such as a condensate). In some embodiments, at least a portion of the starting bioisoprene composition is in a solid phase. In some embodiments, at least a portion of the starting bioisoprene composition is absorbed to a solid support, such as a support that includes silica and/or activated carbon. In some embodiments, the starting bioisoprene composition is mixed with one or more solvents. In some embodiments, the starting bioisoprene composition is mixed with one or more gases.

In some embodiments, the starting bioisoprene composition includes one or more of the following: an alcohol, an aldehyde, a ketone, or an ester (such as any of the alcohols, aldehydes, ketones or esters described herein). In some embodiments, the bioisoprene composition includes (i) an alcohol and an aldehyde, (ii) an alcohol and a ketone, (iii) an aldehyde and a ketone, or (iv) an alcohol, an aldehyde, and a ketone. In some embodiments, any of the isoprene compositions further includes an ester.

In some embodiments, the starting bioisoprene composition comprises one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the starting bioisoprene composition comprises 1 ppm or more of one or more of the following: methanol, acetaldehyde, ethanol, methanethiol, 1-butanol, 3-methyl-1-propanol, acetone, acetic acid, 2-butanone, 2-methyl-1-butanol, or indole. In some embodiments, the concentration of more of one or more of the following: methanol, acetaldehyde, ethanol, methanethiol, 1-butanol, 3-methyl-1-propanol, acetone, acetic acid, 2-butanone, 2-methyl-1-butanol, or indole, is between about 1 to about 10,000 ppm in a starting bioisoprene composition (such as off-gas before it is purified). In some embodiments, the starting bioisoprene composition (such as off-gas after it has undergone one or more purification steps) includes one or more of the following: methanol, acetaldehyde, ethanol, methanethiol, 1-butanol, 3-methyl-1-propanol, acetone, acetic acid, 2-butanone, 2-methyl-1-butanol, or indole, at a concentration between about 1 to about 100 ppm, such as about 1 to about 10 ppm, about 10 to about 20 ppm, about 20 to about 30 ppm, about 30 to about 40 ppm, about 40 to about 50 ppm, about 50 to about 60 ppm, about 60 to about 70 ppm, about 70 to about 80 ppm, about 80 to about 90 ppm, or about 90 to about 100 ppm. In some embodiments, the starting bioisoprene composition contains less than 1 ppm of methanethiol (a potent catalyst poison and a source of sulfur in the final fuel product) Volatile organic compounds from cell cultures (such as volatile organic compounds in the headspace of cell cultures) can be analyzed using standard methods such as those described herein or other standard methods such as proton transfer reaction-mass spectrometry (see, for example, Bunge et al., *Applied and Environmental Microbiology*, 74(7):2179-2186, 2008 which is hereby incorporated by reference in its entirety, particular with respect to the analysis of volatile organic compounds).

The invention also contemplates the use of a starting bioisoprene composition that is derived from a biological source (such as a cell culture) that co-produces isoprene and hydrogen. In some embodiments, the starting bioisoprene compositions comprise isoprene and hydrogen in ratios ranging from at least one molar percent of isoprene for every three molar percent of hydrogen to at least one molar percent of isoprene for every four molar percent of hydrogen. In some embodiments, the starting bioisoprene compositions comprise isoprene and hydrogen in ratios ranging from at least one molar percent of hydrogen for every three molar percent of isoprene to at least one molar percent of hydrogen for every four molar percent of isoprene. In some embodiments, the starting bioisoprene compositions comprise isoprene and hydrogen in molar ratios of about 1 to 9, 2 to 8, 3 to 7, 4 to 6, 5 to 5, 6 to 4, 7 to 3, 8 to 2, or 9 to 1. In some embodiments, the composition further comprises from 1 to 11 molar percent isoprene and from 4 to 44 molar percent hydrogen. In some embodiments, the composition further comprises oxygen, carbon dioxide, or nitrogen. In some embodiments, the composition further comprises from 0 to 21 molar percent oxygen, from 18 to 44 molar percent carbon dioxide, and from 0 to 78 molar percent nitrogen. In some embodiments, the composition further comprises $1.0 \times 10^{-4}$ molar percent or less of non-methane volatile impurities. In some embodiments, the non-methane volatile impurities comprise one or more of the following: 2-heptanone, 6-methyl-5-hepten-2-one, 2,4,5-trimethylpyridine, 2,3,5-trimethylpyrazine, citronellal, acetaldehyde, methanethiol, methyl acetate, 1-propanol, diacetyl, 2-butanone, 2-methyl-3-buten-2-ol, ethyl acetate, 2-methyl-1-propanol, 3-methyl-1-butanal, 3-methyl-2-butanone, 1-butanol, 2-pentanone, 3-methyl-1-butanol, ethyl isobutyrate, 3-methyl-2-butenal, butyl acetate, 3-methylbutyl acetate, 3-methyl-3-buten-1-yl acetate, 3-methyl-2-buten-1-yl acetate, 3-hexen-1-ol, 3-hexen-1-yl acetate, limonene, geraniol (trans-3,7-dimethyl-2,6-octadien-1-ol), citronellol (3,7-dimethyl-6-octen-1-ol), (E)-3,7-dimethyl-1,3,6-octatriene, (Z)-3,7-dimethyl-1,3,6-octatriene, 2,3-cycloheptenolpyridine, or a linear isoprene polymer (such as a linear isoprene dimer or a linear isoprene trimer derived from the polymerization of multiple isoprene units). In some embodiments, the non-methane volatile impurities comprise one or more of the following: the isoprene composition includes one or more of the following: an alcohol, an aldehyde, or a ketone (such as any of the alcohols, aldehydes, or ketones described herein). In some embodiments, the isoprene composition includes (i) an alcohol and an aldehyde, (ii) an alcohol and a ketone, (iii) an aldehyde and a ketone, or (iv) an alcohol, an aldehyde, and a ketone. In some embodiments, the non-methane volatile impurities comprise one or more of the following: methanol, acetaldehyde, ethanol, methanethiol, 1-butanol, 3-methyl-1-propanol, acetone, acetic acid, 2-butanone, 2-methyl-1-butanol, or indole.

Recovery

Methods and apparatus for the purification of a bioisoprene composition from fermentor off-gas which can be used are described in PCT/US2010/060552, which is incorporated herein by reference in its entirety.

A bioisoprene composition from a fermentor off-gas may contain bioisoprene with volatile impurities and bio-byproduct impurities. In some embodiments, a bioisoprene composition from a fermentor off-gas is purified using a method comprising: (a) contacting the fermentor off-gas with a solvent in a first column to form: an isoprene-rich solution comprising the solvent, a major portion of the isoprene and a major portion of the bio-byproduct impurity; and a vapor comprising a major portion of the volatile impurity; (b) transferring the isoprene-rich solution from the first column to a second column; and (c) stripping isoprene from the isoprene-rich solution in the second column to form: an isoprene-lean solution comprising a major portion of the bio-byproduct impurity and a purified isoprene composition.

Exemplary Chemical Transformations of Isoprene

Available methods for chemical transformation of petroleum-derived isoprene to fuel constituents may not be optimal for achieving the highest yields and most desirable product mixtures when used for transformation of biologically derived isoprene to fuel constituents. Isoprene derived from biological sources, as described herein, has a different composition and impurity profile than petroleum-derived isoprene, and therefore optimal yields, product mixtures, and product impurity profiles for transformation of such isoprene to fuel constituents may be different from those used for petroleum-derived isoprene. Furthermore, because of the impurity profile of petroleum-derived isoprene, such as the substantial presence of C5 compounds other than isoprene, petroleum-derived isoprene generally must be purified before it is subjected to further chemical transformations. Purification of isoprene takes time and additional resources and some of the isoprene in the crude mixture can be lost during the process, leading to lower overall yields of desired fuel constituents. In addition, isoprene is a highly reactive compound, and it tends to form gums and polymers under many reaction conditions. Most of the chemical transformations described herein are typically carried out in the liquid phase or using heterogeneous catalysis, in which the catalyst is immobilized on a solid support and the other starting materials are in the liquid phase. In some embodiments, the chemical transformations can be carried out in either the liquid or gas phase.

The invention provides methods and compositions for producing fuel constituents from a bioisoprene composition taking advantage of the accessibility and the unique impurity profiles of the bioisoprene compositions. Chemical reactions that are sensitive to hydrocarbon impurities that are present in petroleum based isoprene compositions can be carried out with bioisoprene compositions without extensive purification. Bioisoprene compositions may be used in reactions that can tolerate oxygenated compounds present in bioisoprene compositions without purification to produce fuel constituents or intermediates to fuel constituents. In some instances, the presence of oxygenated compounds enhances the reactivity of isoprene and/or improves the yields of reactions starting from isoprene.

Although current industrial use of isoprene is predominantly in the production of synthetic rubber, isoprene is a reactive conjugated diene and undergoes a varieties of chemical transformations to form oxygenates and higher molecular weight hydrocarbons. For example, Palladium(0) complexes (Pd(acac)-2-Ph$_3$P and Pd(OAc)-2-Ph$_3$P) catalyze dimerization and telomerization of isoprene in alcohol solvents to give linear isoprene dimers (e.g. 2,7-dimethyl-1,3,7-octatriene) and methoxydimethyloctadienes (Zakharkin, L. I. and Babich, S. A. *Russ. Chem. Bull.* (1976), pp 1967-1968.) Adams, J. M. and Clapp, T. V. (*Clay and Clay Minerals* (1986), 34(3), 287-294) reported reactions of isoprene over divalent and trivalent transition metal-exchanged montmorillonites (e.g. $Cr^{3+}$-montmorillonite) to give isoprene dimers and adducts with methanol. The linear dimerization of isoprene catalyzed by Ni(0)-aminophosphinite systems resulted in regioselective tail-to-tail linear dimers, accompanied by a competitive cyclodimerization reaction (Denis, Philippe; Croizy, Jean Francois; Mortreux, Andre; Petit, Francis, *Journal of Molecular Catalysis* (1991), 68(2), 159-75. Denis, Philippe; Jean, Andre; Croizy, Jean Francois; Mortreux, Andre; Petit, Francis, *Journal of the American Chemical Society* (1990), 112 (3), 1292-4.) New chiral aminophosphinite ligands, e.g., (+)-MeCH$_2$CHMeCH(NH$_2$)CH$_2$OPPh$_2$ was investigated as homogeneous catalysts in the linear dimerization of isoprene, leading to a conversion rate above 50% (Masotti, Henriette; Peiffer, Gilbert; Siv, Chan; Courbis, Pierre; Sergent, Michelle; Phan Tan Luu, Roger, *Bulletin des Societes Chimiques Belges* (1991), 100(1), 63-77.)

Thermal dimerization of isoprene at 110-250° C. in presence of dinitrocresol as polymerization inhibitor gives high yields of dimers and little polymer (U.S. Pat. No. 4,973,787.) Ni-catalyzed dimerization of isoprene yields a dimethyl-1,5-cyclooctadiene mixture consisting of 80% 1,5-dimethyl-1,5-cyclooctadiene and 20% 1,6-dimethyl-1,5-cyclooctadiene (Doppelt, Pascal; Baum, Thomas H.; Ricard, Louis, *Inorganic Chemistry* (1996), 35(5), 1286-91.) Isoprene is converted to dimethylcyclooctadienes with a catalytic amount of Cp*Ru(η4-isoprene)Cl and AgOTf (Itoh, Kenji; Masuda, Katsuyuki; Fukahori, Takahiko; Nakano, Katsumasa; Aoki, Katsuyuki; Nagashima, Hideo, *Organometallics* (1994), 13(3), 1020-9.) JP59065026A (1984) reported preparation of 1,6-dimethyl-1,5-cyclooctadiene by cyclic dimerization of isoprene in the presence of catalysts comprising Fe carboxylates or β-diketone compounds, organo-Al or Mg compounds, and 2,2'-dipyridyl derivatives having electron-donating groups. Dimethylcyclooctadiene was prepared by cyclodimerization of isoprene over 3-component catalysts containing Ni carboxylates or β-ketones, organoaluminum or organomagnesium compounds and substituted triphenylphosphite (JP58055434A, 1983.) 1,5-Dimethyl-1,5-cyclooctadiene was prepared by cyclodimerization of isoprene at 100-300° in an inert organic solvent in the presence of a homogeneous catalyst containing Fe(3) salt, organoaluminum compound and an activator (SU615056A1, 1978), in the presence of a homogeneous catalyst containing Ni acetylacetonate, a triarylphosphite and perhydroalumophenolene (SU493455A1, 1975), in the presence of a catalyst containing a mixture of a Ni carboxylate or carboxylate or chelate compounds of Ni and 1-hydroxy-3-carbonyl compounds, trialkylaluminum, dialkylmagnesium or active organo-Mg compounds obtained from conjugated dienes and Mg, triaryl phosphites and tertiary amines (JP48064049A, 1973), or in the presence of a catalyst composed of Ni naphthenate, Et$_3$Al, and tri-o-cresyl phosphate (Suga, K.; Watanabe, S.; Fujita, T.; Shimada, T., *Israel Journal of Chemistry* (1972), 10(1), 15-18.) U.S. Pat. No. 3,954,665 disclosed dimerization of isoprene in the presence of reaction products of [(η3-C6H5)NiBr]$_2$ or [M(NO)$_2$X]$_2$ (M=Fe, Co; X=Cl, I, Br) with Fe, Co, or Ni carbonyls. European Patent No. 2411 (1981) disclosed cyclodimerization of isoprene over a Fe(NO)$_2$Cl-bis(1,5-cyclooctadiene)nickel catalyst at from −5° to +20° to give 1-methyl- and 2-methyl-4-isopropenyl-1-cyclohexene and 1,4- and 2,4-dimethyl-4-vinyl-1-cyclohexene. U.S. Pat. No. 4,189,403 disclosed preparation of 1,5-dimethyl-1,5-cyclooctadiene and 1,4-dimethyl-4-vinyl-1-cyclohexene by contacting isoprene with a mixed catalyst of a tris(substituted hydrocarbyl) phosphite, arsenite, or antimonite and a Group VIII metal(0) compound (e.g. Ni acetylacetonate). Jackstell, R.; Grotevendt, A.; Michalik, D.; El Firdoussi, L.; Beller, M. *J. Organometallic Chem.* (2007) 692(21), 4737-4744 cites the use of palladium/carbene catalysts for isoprene dimerization. Bowen, L.; Charernsuk, M.; Wass, D. F. *Chem. Commun.* (2007) 2835-2837 describes the use of a chromium N,N-bis(diarylphosphino)amine catalyst for the production of linear and cyclic trimers of isoprene.

Isoprene was reportedly dimerized in the presence of a Ni catalyst to yield cis-2-isopropenyl-1-methylvinylcyclobutane (Billups, W. E.; Cross, J. H.; Smith, C. V., *Journal of the American Chemical Society* (1973), 95(10), 3438-9.) The oligomerization of isoprene [78-79-5] catalyzed by nickel naphthenate and isoprene magnesium in the presence of various phosphites as electron donors gave cyclic dimers containing dimethylcyclooctadiene [39881-79-3]; in particular 1,1,1-tris(hydroxymethyl)propane phosphite [39865-19-5] gave trimethylcyclododecatriene [39881-80-6] selectively (Suga, Kyoichi; Watanabe, Shoji; Fujita, Tsutomu; Shimada, Takashi, *Journal of Applied Chemistry & Biotechnology* (1973), 23(2), 131-8.) WO2006/051011 discloses preparation of trimethylcyclododecatriene, useful in perfumes and fragrances, by the trimerization of isoprene in the presence of a catalyst system comprising Ni and/or Ti, one or more organometallic compound, and a Group VA compound, and that the reaction is conducted in a hydroxyl group-containing solvent. The products of the chemical transformations as described herein can also be used for perfumes, fragrances, and other fine chemicals (e.g., pesticides, surfactants, lubricants, etc.). See, e.g., Monteiro, et al., *Topics in Catalysis*, Vol. 27, Nos. 1-4, February 2004. Ligabue, R. A.; Dupont, J.; de Souza, R. F., Alegre, R. S. *J. Mol. Cat. A: Chem.* (2001), 169(1-2), 11-17, describes the selective dimerization of isoprene to six-membered dimers using an iron nitrosyl catalyst in an ionic liquid. Huchette, D.; Nicole, J.; Petit, F., *Tetrahedron Letters* (1979), (12), 1035-8, describes the electrochemical generation of an iron nitrosyl catalyst and subsequent use for the dimerization of isoprene to cyclohexene dimers. Zakharkin, L. I.; Zhigareva, G. G.; Pryanishnikov, A. P. *Zhurnal Obshchei Khimii* (1987), 57(11), 2551-6, describes the cyclooligomerization of isoprene on complex nickel and iron catalysts.

Optimization of Reaction Conditions

Isoprene derived from biological sources, as described herein, can be advantageous over petroleum-based isoprene as a starting material for production of fuel constituents. Biologically derived isoprene does not contain high levels of non-isoprene C5 impurities, and therefore it may be subject to chemical transformation without prior purification. Certain impurities in petroleum-derived isoprene, such as acetylenes, may poison some of the catalysts used for production of fuel products, such as metathesis catalysts. Because such impurities are present in small amounts or are absent from biologically derived isoprene, they do not need to be separated out prior to chemical transformation. Furthermore, the presence of certain impurities in biologically derived isoprene, such as alcohols and other oxygenates, can be beneficial for some of the chemical transformations described herein, such as acid-catalyzed dimerization.

In one aspect of the invention, any of the chemical transformations described herein can be optimized for use with isoprene derived from biological sources. Reaction conditions can be optimized to achieve high yields of desired product, to achieve a particular mixture of products, to achieve a fuel constituent with particular physical properties, or to achieve a particular impurity profile in the product. In some embodiments, reaction conditions are optimized using a screening process, in which biologically produced isoprene is subject to a matrix of reaction conditions in which various reaction parameters are altered along different axes of the matrix. Reaction parameters that can be varied include, but are not limited to, reaction time, temperature, pressure, catalyst identity, solvent, co-catalyst identity, ratio of reactants to one another, vapor pressure, type of catalyst, and ratio of products to one another. In a particular embodiment, kinetic vs. thermodynamic control is the variable reaction parameter. In another particular embodiment, gas vs. liquid phase is the variable reaction parameter. Optimal reaction conditions can be determined by analysis of the products of each set of reaction conditions in the matrix, using any of the analytical methods described herein, with respect to the goal of the particular optimization screen done. The screening can be carried out in an iterative process, in which desirable reaction conditions can be narrowed down through consecutive rounds of screening. In some embodiments, the optimal conditions for a particular chemical transformation using biologically derived isoprene are different than conditions for the same chemical transformation on petroleum-derived isoprene. Particular chemical transformation that may be desirable or that may provide a starting point for the optimization process are described in more detail as follows.

Isoprene Metathesis

Although isoprene undergoes a variety of chemical reactions and olefin metathesis is becoming widely used in synthesis of organic compounds, examples for olefin metathesis of isoprene have been scarce. Woerlee, et all (*Applied Catalysis*, 10 (1984) 219-229) reported a $Re_2O_7/Al_2O_3$—$Sn(CH_3)_4$ metathesis catalyst transforming conjugated dienes into alkenes, trienes and tetraenes at room temperature, but observed that conjugated dienes with isopropenyl group are inert. Accordingly, one aspect of this invention provides methods and compositions for producing fuel constituents from a bioisoprene composition (e.g., gaseous phase) using olefin metathesis whereby isoprene is converted to a mixture of olefins though the cleavage and reformation of carbon-carbon double bonds. The reaction conditions, catalysts, co-catalysts, promoters and solvents may be optimized systematically to achieve a desired composition or molecular weight distribution of the olefin product mixture. For example, to produce a fuel constituent suitable for use in a diesel fuel after complete hydrogenation of an olefin mixture from isoprene metathesis, the desired olefin mixture is a C10-C20 olefin mixture. When the metathesis reaction reaches an equilibrium or steady state mixture, the undesirable fractions in the olefin mixture may be separated from the desirable fractions and subject to further metathesis for molecular weight redistribution. In a continuous process, the undesirable fractions separated may be cycled back into the vessel for isoprene metathesis. For example, in a method for producing a fuel constituent suitable for use in a diesel fuel, the undesirable <C10 and >C20 olefin fractions are separated from the desirable C10-C20 olefin fractions, e.g. by fractional distillation, and subject to another metathesis reaction or cycled back into the isoprene metathesis mixture in a continuous process.

In some embodiments, the invention provides a method for producing a fuel constituent from a bioisoprene composition comprising chemically transforming a substantial portion of the isoprene in the bioisoprene composition to non-isoprene compounds by contacting the bioisoprene composition with a catalyst for olefin metathesis to produce one or more olefin products and then catalytically hydrogenating the olefin product to form an alkane fuel constituent. In some embodiments, isoprene undergoes metathesis to form one or more higher or lower olefins, such as ethylene, isobutylene, dimethylhexenes, and other branched and cyclic olefinic compounds (FIG. 2). In some instances, the predominant product in the metathesis mixture is a cyclic olefin. Such reactions are typically catalyzed by metal-complexes, such as chloride, oxides, or other compounds containing Mo, Ru, W, Re, Os, Ir, Ti, V, Cr, Co, Nb, Rh, or Ta. Typical metathesis co-catalysts are EtAlCl$_2$, R$_3$AlCl$_2$, R$_3$Al, and R$_4$Sn (R=Ph, Me, Et, or Bu). Typical metathesis promoters are O$_2$, EtOH, and PhOH. In a particular embodiment, the metathesis catalysts is a Schrock-carbene complex or a Grubbs-class catalyst. Other metathesis catalysts have been described, many of which have been shown to have good industrial applicability, such as WO$_3$/SiO$_2$, naphtha steam crackers containing an integrated metathesis unit, Re$_2$O$_7$/Al$_2$O$_3$, alumina-supported molybdate metathesis catalysts, highly active ruthenium complexes (e.g., [RuCl$_2$(=CHPh)(H$_2$IPr)(PCy$_3$)], Grubbs catalyst), WCl$_6$-based catalysts, RuCl$_3$/HCl, tetrakis(tridodecylammonium)octa-molybdate activated with a mixture of Et$_2$AlCl, propanol, and SiCl$_4$, and heterogeneous rhenium oxide catalysts. (See, for example, J. C. Mol. *J. Mol. Catalysis. A: Chemical* 213 (2004) 39-45.) In a particular embodiment, metathesis is carried out via the Shell higher olefins process (SHOP), which utilizes a homogeneous nickel-phosphine catalyst (preferably at 90-100° C. and 100-110 bar) in a polar solvent (preferably 1,4-butanediol). Examples have also been described in which metathesis of conjugated dienes is carried out using a ruthenium benzylidene (Grubbs-type) catalyst. Use of steric or electronic protection of one of the conjugated double bonds led to selective reaction of one or the other double bond. (See T. W. Funk et al. *Org. Lett.* 7 (2005) 187-190.) Hydrogenation of the products of isoprene metathesis gives compounds suitable for use in fuel compositions.

In some embodiments, the invention provides a continuous process for conversion of a bioisoprene composition into fuel constituents via olefin metathesis comprising (i) contacting a bioisoprene composition with an catalyst for olefin metathesis to form an olefin mixture in a metathesis reactor; (ii) fractionating the olefin mixture to a first light fraction and a first heavy fraction comprising C7-C50 olefins; (iii) returning the first light fraction to the metathesis reactor for further metathesis; (iv) fractionating the first heavy fraction to a second light fraction to a second light fraction and a second heavy fraction; (v) returning the second heavy fraction to the metathesis reactor for further disproportionation; and (vi) hydrogenating the second light fraction to produce a fuel constituent. The olefin mixture formed in the metathesis reactor can be a statistical distribution of products comprising C2-C50 olefins. The first fractionation may be carried out in a first distillation column where the overhead fraction is the first light fraction comprising light components such as C2-C6 olefins or <C7 olefins. These light components include ethylene, propylene, isobutylene, isoprene and other light olefins. The first heavy fraction from the first distillation column may enter a second fractionation column where the desired linear and cyclic components in the C7 to C15 range are removed in the overhead fraction. In some embodiments, the second light fraction consists of C7-C15 olefins. In some embodiments, the second heavy fraction comprises C16-C50 olefins. Olefins in the second light fraction can be subjected to subsequent hydrotreating or hydrogenation to produce a fuel constituent. The second heavy fraction from the second distillation column may be recycled to the metathesis reactor where they are subjected to olefin disproportionation resulting in a distribution of products in the C2 to C50 range which are then fractionated by distillation as described above. One embodiment of the method is depicted in the flow diagram shown in FIG. 3.

The overall distribution of products produced in the metathesis reactor can be modulated through an optional light-olefin co-feed consisting of ethylene or mixtures of ethylene and other light olefins (<C5). The ratio of light olefin co-feed to the bioisoprene feed can range from 1:100 to 2:1. Higher light olefin co-feed to bioisoprene feed ratios tend to lower the average molecular weight of the products and reduce the amount of undesired heavy fractions emerging from the metathesis reactor. A light olefin co-feed can also help prevent the formation of involatile gums and polymers (>C50) in the metathesis reactor that might otherwise deactivate the metathesis catalyst (see Oziomek U.S. Pat. No. 5,446,102).

Acid Catalyzed Oligomerization

Figure 4:
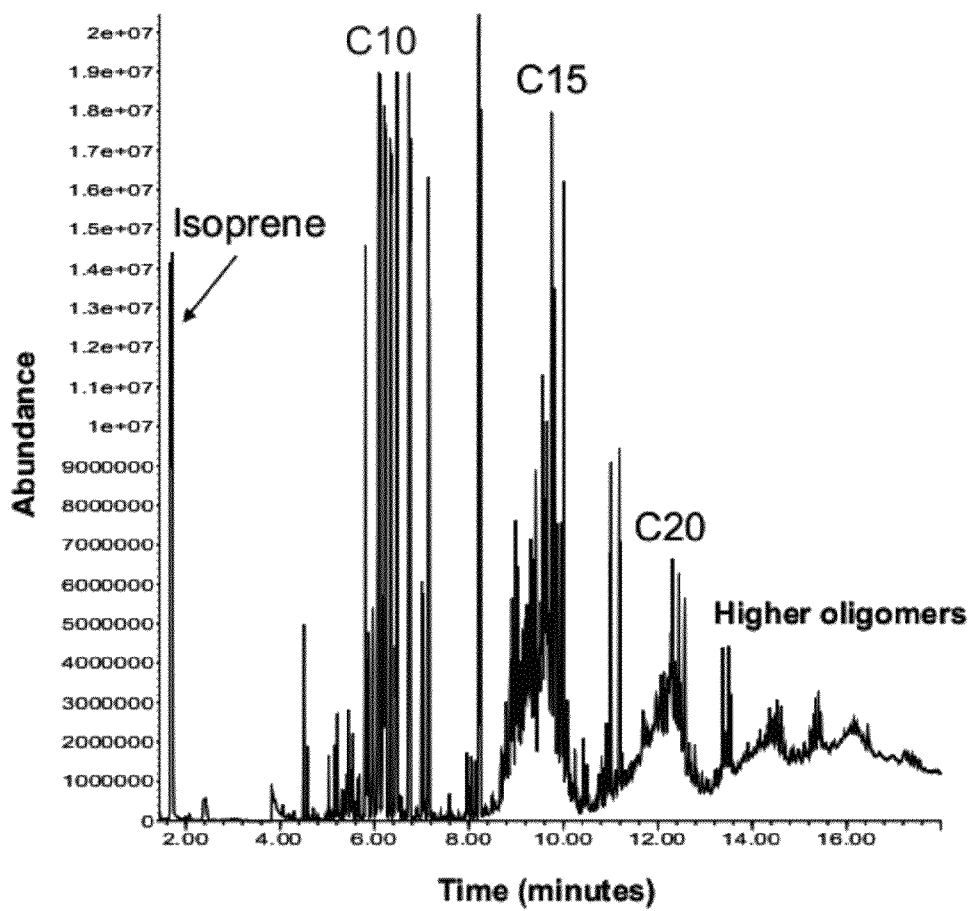
FIG. 4 shows the GC/MS Total Ion Chromatogram for products derived from Amberlyst 15 acid resin-catalyzed oligomerization of isoprene in a bioisoprene composition.

Isoprene is readily oligomerized in the presence of an acid catalyst to give a complex array of compounds including dimers, trimers, higher oligomers, aromatic products, and polymeric products. FIG. 4 and the Examples section show an example of the complex product mixture when isoprene is treated with an Amberlyst 15 acid resin in toluene. Kinetic control of the reaction can favor certain products, for example lower oligomers, although gum formation and coking are known issues leading to catalyst deactivation. Processes for the direct oligomerization of isoprene need to have a reasonable selectivity for the desired products.

Accordingly, the invention provides a method for producing fuel constituents by acid catalyzed oligomerization of a bioisoprene composition whereby the oxygenated compounds present in the bioisoprene composition, such as alcohols, enhance the selectivity for a desired product. (see, e.g. Marchionna (*Catalysis Today* 65 (2001) 397-403, 399). The reaction conditions, the catalyst and the solvent used can be optimized to produce efficiently fuel constituents of desired molecular weight. For example, conditions that provide short reaction time tend to favor kinetic products that have relatively low molecular weight, such as C7 to C15 hydrocarbons suitable for "gasoline" or fuels used in automobiles. The efficiency for converting bioisoprene to lower molecular weight hydrocarbons may be further improved by recycling the higher molecular weight olefinic oligomers initially produced, for examples by thermal cracking, steam cracking or olefin metathesis. Equilibrium would be shifted to desired products by their continuous removal from the reactor. In some embodiments, the higher molecular weight olefins are treated with an appropriate catalyst for olefin metathesis such as a rhenium catalyst or other metal-complex, such as chloride, oxides, or other compounds containing Mo, Ru, W, Re, Os, Ir, Ti, V, Cr, Co, Nb, Rh, or Ta to produce lower molecular weight olefins, which may be combined with the initial lower molecular weight olefins for further processing such as complete hydrogenation to produce saturated alkane fuel constituents, or be fed into the acid catalyzed oligomerization reaction.

In one aspect, the invention provides a method for producing a fuel constituent from a bioisoprene composition comprising: (i) contacting a bioisoprene composition with an acid catalyst to produce mixed olefin products (e.g., C5-C50 olefins) containing higher molecular weight olefin products (e.g., C16-C50 olefins) and lower molecular weight olefin products (e.g., C5-C15 olefins); (ii) converting the higher molecular weight olefin products to lower molecular weight olefins; and (iii) hydrogenating the lower molecular weight olefin products (e.g., C5-C15 olefins) to produce saturated hydrocarbons (e.g., C5-C15 alkanes) as fuel constituents. Preferably, a substantial portion of the isoprene in the bioisoprene composition is chemically converted to non-isoprene compounds. In some embodiments, step (i) is carried out using a suitable catalyst and under conditions of kinetic control which favors formation of lower oligomers. In some embodiments, step (ii) is carried out by an olefin metathesis reaction that converts the higher oligomers to lower molecular weight olefins. The hydrogenation step (iii) may be carried out using a variety of hydrogenation catalysts such as a heterogeneous palladium catalyst, including palladium on carbon (Pd/C), palladium on alumina (Pd/Al$_2$O$_3$), or palladium on silica (Pd/SiO$_2$) in grades ranging from 0.1% Pd to 20% Pd (w/w) relative to the support material.

Catalysts and conditions for polymerization of isoprene have been well studied and certain conditions have been shown to enhance polymerization (see Sadahito A. and Shokyoku K. *Chem. Rev.* 2009, 109, 5245-5287.) Thus, in some embodiments, conditions that tend to stabilize carbocations and thus promote living carbocationic polymerization should be avoided in acid catalyzed oligomerization of bioisoprene compositions.

Alkylation of Isoamylenes by Isoparaffins

Figure 5:
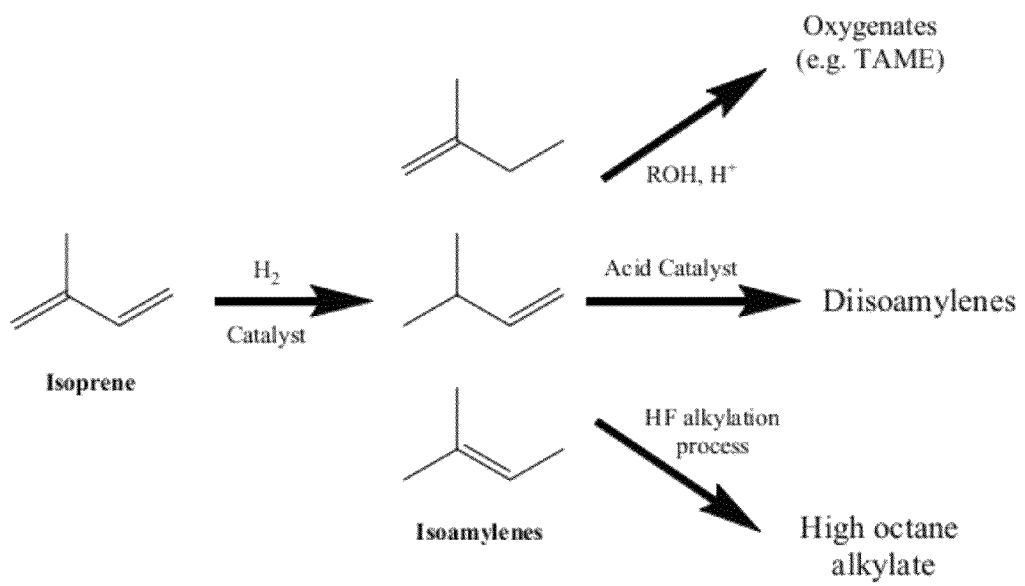
FIG. 5 shows a reaction scheme for conversion of isoamylenes to fuels and fuel intermediates.

Partial hydrogenation of isoprene gives a mixture of isoamylenes that may be transformed to other valuable products us fuel. However, production of fuel from isoprene derived isoamylenes has not been commercially feasible, partially due to the extensive purification required for petroleum derived isoprene compositions. Thus, one aspect of the invention provides a method for producing a fuel constituent from a bioisoprene composition without extensive purification by partially hydrogenating the bioisoprene composition to form one or more isoamylenes and the isoamylenes produced is converted to fuel constituents by further chemical transformations such as dimerization, reaction with alcohols and alkylation by isoparaffins (FIG. 5).

In some embodiments, the method for producing a fuel constituent from a bioisoprene composition comprises chemically transforming a substantial portion of the isoprene in the bioisoprene composition to one or more non-isoprene compounds by partially hydrogenating the bioisoprene composition to produce an isoamylene and then alkylating the isoamylene with an isoparaffin to form an alkylate fuel constituent. In some embodiments, isoparaffins and olefins derived from biologically produced isoprene can be alkylated to make high-octane alkylates.

Methods for alkylation are well established and have been employed by refineries on a large scale. Feedstocks can include olefins such as propylene, 2-butene, isobutylene, and isoamylenes. Isoparaffins can include propane, isobutane and isopentane. In some embodiments, the isopentane used in isoamylene alkylation is derived from bioisoprene from a bioisoprene composition by complete hydrogenation. In some embodiments, the catalyst is hydrofluoric acid. Less toxic catalysts have also been described, such as an acid component (such as sulfuric acid, a fluorosulfonic acid, a perhaloalkylsulfonic acid, and ionic liquid, or a mixture of Bronsted and/or Lewis acids) mixed with a polymer component. (See, for example, US 2010/0094072.) U.S. Pat. No. 6,429,349 B1 describes a method of alkylating C3-C5 olefins by mixtures of isobutene and isopentane with an acid catalyst to form a high octane alkylate that has relatively low Reid vapor pressure (RVP). Acid catalysts suitable for this transformation include hydrofluoric acid, sulfuric acid, a halogenated sulfuric acid, and a halogenated sulfonic acid. K. Kranz has described alkylation of C3-C5 olefins with isobutene in the presence of a strong acid catalyst, such as hydrofluoric acid or sulfuric acid (*Alkylation Chemistry: Mechanisms, operating variables, and olefin interactions*, STRATCO, Leawood Kans., May 2003). Kranz describes a number of factors that impact the product quality and operating cost of alkylation: 1) Maintaining a high isobutene concentration reduces the likelihood of olefin-olefin polymerization that will result in lower octane; 2) Keeping the temperature in the neighborhood of 50° C. to minimize polymerization, which can result from high temperatures and avoid slowing the settling rate of the acid from the alkylate, which can result from low temperatures; and 3) Maintaining a high sulfuric acid concentration (such as above 90% sulfuric acid) to minimize polymerization and red oil production. (See also J. R. Peterson et al. *Improved Amylene Alkylation Economics.* STRATCO, Inc. 1999.) Alkylation of C3-C5 olefins with isopentane has also been described and shown to give high octane products. (See D. C. Graves. *Alkylation Options for Isobutylene and Isopentane*, STRATCO, Leawood, Kans., November 2001.) Cruz et al. *Reactive & Functional Polymers* 65: 149-160 (2005) describes the effects of alcohols on dimerization of isoamylenes and discloses fuel properties of diisoamylenes. US 2010/0094072 describes improved catalysts for olefin alkylation. US 2009/0099400 describes the use of solid phosphoric acid catalyst for dimerizing olefins. As with any of the references cited herein, all of these references are incorporated in their entirety for their teachings, particularly for the aspects described above.

Isoamylene Metathesis

The isoamylenes produced from partial hydrogenation of bioisoprene may be converted to fuel constituents by metathesis followed by hydrogenation.

In some embodiments, the invention provides a method for producing a fuel constituent from a bioisoprene composition comprising chemically transforming a substantial portion of the isoprene in the bioisoprene composition to one or more non-isoprene compounds by partially hydrogenating the bioisoprene composition to produce one or more isoamylene products, contacting the one or more isoamylene products with a catalyst for olefin metathesis to produce one or more olefin products, and then catalytically hydrogenating the one or more olefin products to form one or more alkane fuel constituents. In some embodiments, the isoamylene undergoes metathesis to form one or more higher or lower olefins, such as ethylene and/or dimethylhexenes (e.g., 3,4-dimenthylhexenes). Such reactions are typically catalyzed by metal-complexes, such as chloride, oxides, or other compounds containing Mo, Ru, W, Re, Os, Ir, Ti, V, Cr, Co, Nb, Rh, or Ta. Typical metathesis co-catalysts are EtAlCl$_2$, R$_3$AlCl$_2$, R$_3$Al, and R$_4$Sn (R=Ph, Me, Et, or Bu). Typical metathesis promoters are O$_2$, ethanol, and phenol. In a particular embodiment, the metathesis catalysts is a Schrock-carbene complex or a Grubbs-class catalyst. Other metathesis catalysts have been described, many of which have been shown to have good industrial applicability, such as WO$_3$/SiO$_2$, naphtha steam crackers containing an integrated metathesis unit, Re$_2$O$_7$/Al$_2$O$_3$, alumina-supported molybdate metathesis catalysts, highly active ruthenium complexes (e.g., [RuCl$_2$(=CHPh) (H$_2$IPr)(PCy$_3$)], Grubbs catalyst), WCl$_6$-based catalysts, RuCl$_3$/HCl, tetrakis(tridodecylammonium)octamolybdate activated with a mixture of Et$_2$AlCl, propanol, and SiCl$_4$, and heterogeneous rhenium oxide catalysts. (See, for example, J. C. Mol. *J. Mol. Catalysis. A: Chemical* 213 (2004) 39-45.) In a particular embodiment, metathesis is carried out via the Shell higher olefins process (SHOP), which utilizes a homogeneous nickel-phosphine catalyst (preferably at 90-100° C. and 100-110 bar) in a polar solvent (preferably 1,4-butanediol). Examples have also been described in which metathesis of conjugated dienes is carried out using a ruthenium benzylidine (Grubbs-type) catalyst. Use of steric or electronic protection of one of the conjugated double bonds led to selective reaction of one or the other double bond. (See T. W. Funk et al.

*Org. Lett.* 7 (2005) 187-190.) Hydrogenation of the products of isoamylene metathesis gives compounds suitable for use in fuel compositions.

Use of Bioisoprene Off-Gas

In one aspect of the invention, a fuel constituent is produced from isoprene directly from the off-gas of bioisoprene production. Accordingly, the fuel constituent is produced from a bioisoprene composition in the gas phase. Production of fuel directly from bioisoprene in off-gas removes the need for recovery and/or purification of the isoprene prior to subjecting it to any of the chemical transformations described herein, thereby decreasing the number of steps required to produce the fuel constituent and also preventing loss of isoprene starting material that may occur upon recovery and/or purification prior to chemical transformation of the isoprene. In some embodiments, therefore, any of the chemical transformations on isoprene described herein can be carried out in the gas phase. Furthermore, the chemical transformations can be optimized to transform isoprene into a desired fuel constituent in an industrially useful yield in the presence of other compounds or impurities that may be present in the off-gas, such as $CO_2$ or oxygenates. In many cases, the optimal conditions for chemical transformation of isoprene in the off-gas will be different than the optimal conditions for chemical transformation of purified isoprene. In some embodiments, the catalyst and other reactants used to transform the isoprene in the off-gas into a fuel constituent are in the solid, liquid or gas phase.

In some embodiments, the gaseous isoprene starting composition undergoes a chemical reaction upon contact with a catalyst to produce an isoprene derivative. The catalyst can be selected from cationic, anionic, coordination, free radical or other catalyst classes. In some embodiments, the gaseous isoprene starting composition undergoes oligomerization or reaction using traditional hydrocarbon cationic catalysis, such as that used to covert isobutylene to isooctane, e.g. sulfuric, phosphoric and other mineral acids, sulfonic acids, fluorosulfonic acids, zeolites and acidic clays. In other embodiments, the isoprene starting composition undergoes dimerization or reaction with other olefins using traditional hydrocarbon cationic catalysis. See, for example, H. M. Lybarger. Isoprene in Kirk-Othmer Encyclopedia of Chemical Technology, 4th ed., Wiley, New York (1995), 14, 934-952. Acid catalysts in both liquid and solid forms can be used. In one embodiment, the solid forms are used. Examples of solid acid resins include Amberlyst 15, 35, XE586, XN1010 (Rohm and Haas) and similar acidic ion-exchange resins. Acidic molecular sieves are other catalysts which can use used, including a medium-pore acid molecular sieve such as ZSM-5, ferrierite, ZSM-22 and ZSM-23. Additional acid catalysts include mineral acids adsorbed onto an inorganic carrier, for example phosphoric acid on silica gel.

In certain embodiments, organometallic catalysts can be used for the conversion of gas-phase isoprene compositions to fuel constituents. For example, many of the catalysts listed herein can be rendered into solid form by adsorption onto a carrier. In one such embodiment a solid palladium catalyst is used to catalyze a telomerization reaction to produce C10 and C15 alcohols from isoprene and water in the presence of carbon dioxide (Inoue (1993) *Bull. Chem. Soc. Jpn.*, 56: 637-638.) Anionic catalysts can also be used for the chemical conversion of isoprene to derivatives. Examples of suitable anionic catalysts include alkyl lithiums, alkali metals, alkali amide salts and other strong bases with pK. Anionic catalysts which can be used include, but are not limited to, n-butyl lithium, lithium naphthalenide and sodium naphthalenide. In most cases a highly pure gas-phase isoprene composition is required in order to avoid quenching of the anionic catalyst by water or other acidic substances. Gas-phase isoprene compositions free from acidic hydrocarbons including acetylenes and 1,3-cyclopentadiene are likewise capable of a reacting with anionic catalysts for conversion of isoprene to fuel constituents.

In certain embodiments, the highly pure isoprene starting material is a gas-phase bioisoprene composition. In other embodiments the isoprene starting material is a fermentation off-gas comprising bioisoprene. In further embodiments the fermentation off-gas comprising bioisoprene is treated to lower the content of water vapor, oxygen, carbon dioxide or other bio-byproduct impurities. In one embodiment, the isoprene content of the fermentation off-gas is enriched by removal of a portion of the permanent gases ($N_2$, $O_2$, $CO_2$) present in the original composition.

The humidity content of the off-gas has an effect on both the extent of conversion and the nature of the resulting compounds. In some instances high humidity is desirable, for example when oxygenated derivatives are sought, or to limit the amount of higher oligomers formed from isoprene. In other cases, humidity might be reduced to maximize the extent of conversion or to minimize the production of oxygenated (hydrated) products. A desiccant, such as silica or molecular sieves, can be used to lower the humidity of the off-gas if desired. Alternatively, the humidity level of an isoprene-containing off-gas can be lowered by condensation of water vapor with a condenser prior to contact with an acid resin. In some instances the presence of oxygenated impurities in the isoprene-containing off-gas (e.g. alcohols) can improve the outcome of the reaction by moderating the reactivity of the acid catalyst and thereby minimizing the formation of higher oligomers, aromatics etc. [Cruz (2005) *React. Func. Poly.*, 65:149-160.]. In one embodiment, the fermentation off-gas containing isoprene is passed through a dehumidifier to remove water vapor, followed by an adsorbent bed to remove oxygenated impurities. Suitable adsorbents include silica, Selexsorb™, zeolites, clays, activated carbon and other materials.

The degree to which isoprene derived from a bioisoprene composition needs to be purified depends on the nature of the catalyst and the process conditions used to convert the isoprene to derivatives. In certain embodiments fermentation off-gas comprising bioisoprene undergoes minimal processing before being subject to chemical catalysis.

In one embodiment, gas-phase isoprene derived from a bioisoprene composition is converted into oligomers (C10 dimers, C15 trimers, C20 tetramers etc.) through contact with a solid acid catalyst. In another embodiment, fermentation off-gas comprising bioisoprene is converted to a gas-phase composition containing isoprene derivatives upon contact with a solid acid catalyst. The reaction can be performed in a vial or vessel containing a gas-phase isoprene composition and a solid acid catalyst. Alternately, fermentation off-gas containing isoprene can be run through a bed or column containing the solid acid catalyst, resulting in the conversion of a portion of the isoprene into isoprene derivatives useful as fuel constituents. The products can be separated from the unreacted isoprene by any effective means, including distillation, membrane separation, absorption/stripping or other separation methods.

In another embodiment, a gas-phase isoprene composition can be converted into aromatic compounds through contact with a solid acid catalyst. For example, a gas-phase isoprene composition can be converted into m-cymene and p-cymene (3-isopropyltoluene and 4-isopropyltoluene) by treatment with Amberlyst 15 acid resin, along with other isoprene derivatives including 3-methyl-2-butanone, isoprene dimers, trimers and tetramers (See Example 5, FIG. 15A-C). The dominant compounds produced in this manner are listed in Table 1.

The amount of isoprene in the gas phase composition can range from 0.01% (100 ppmv) to 100% v/v or any number in between. In certain embodiments, gas-phase isoprene concentrations range from 0.2% to 20%, or 0.2% to 10% v/v or any number in between.

The ratio of products obtained from gas-phase catalysis of isoprene compositions is a function of the concentration of isoprene, the presence of other components in the gas-phase composition, the catalyst used, the contact time with the catalyst and other process conditions (e.g., temperature, pressure).

Figure 16:
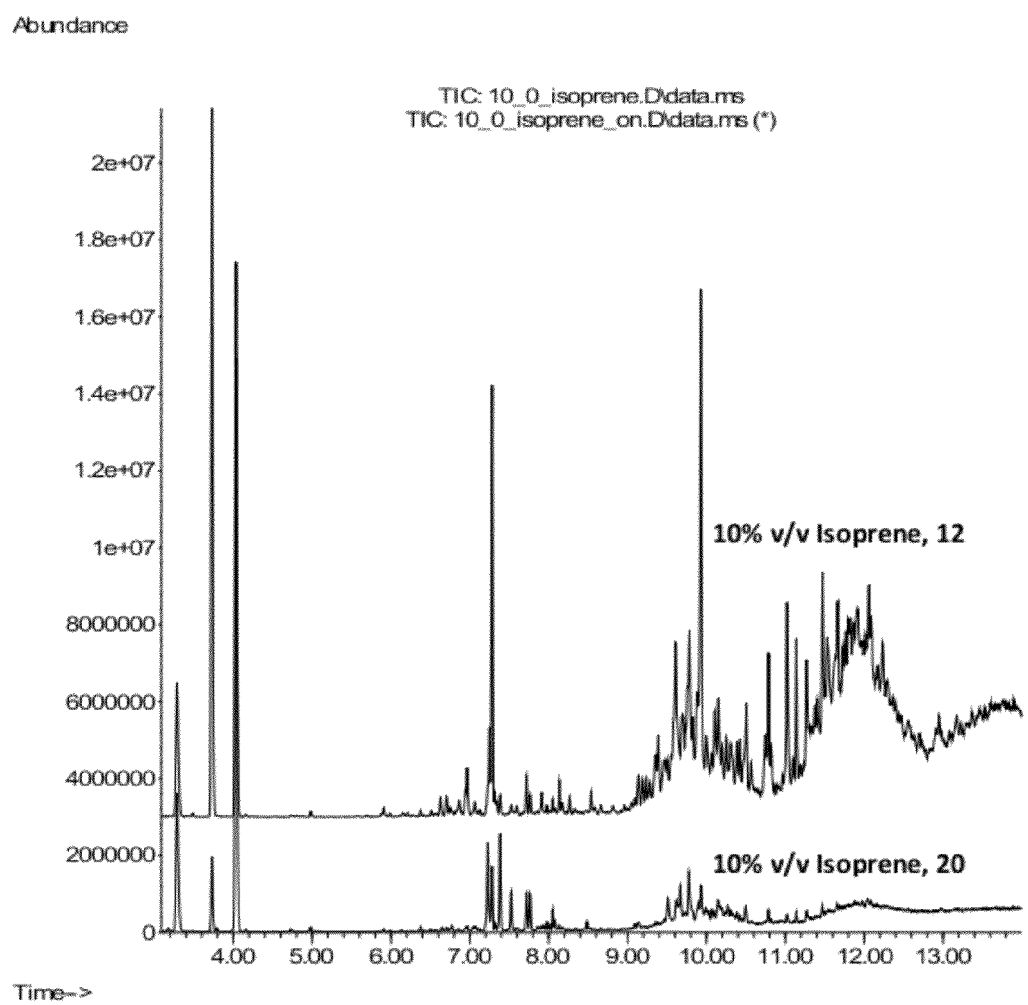
FIG. 16 shows a comparison of the products obtained upon reaction of isoprene vapor (10% v/v) and Amberlyst 15 acid resin in a 20 mL headspace vial for a) 12 hours (indicated by "10% v/v Isoprene, 12") and b) 20 minutes (indicated by "10% v/v Isoprene, 20").

Contact time with the catalyst can be varied to control the ending product produced. In general, the shorter the contact time with the catalyst produces shorter fuel constituents (e.g., C5-C10 or <C5 products) whereas longer contact time with the catalyst produces longer fuel constituents (e.g., >C10 products) Shorter contact time can be used to produce shorter compounds, such as C5 compounds. In one embodiment, shorter contact time can be about 20 seconds to about 12 hours and any number in between. In other embodiments, contact times of at least about 25 seconds, 30 seconds, 35 seconds, 40 seconds, 45 seconds, 50 seconds, 55 seconds, or 1, 2, 3, 4, 5, 6, 7, 8, 9, 10, 11, 12, 13, 14, 15, 16, 17, 18, 19, 20, 25, 30, 35, 40, 45, 50, 55 minutes or 1, 2, 3, 4, 5, 6, 7, 8, 9, 10, 11, 12 hours can be used. In other embodiments, contact time longer than about 12 hours can be used to make the shorter fuel constituents. Longer contact time can be used to produce longer fuel constituents. Non-limiting examples of longer contact times that can be used include, but are not limited to: at least about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours. For example, FIG. 16 shows the result of reaction of a gas-phase isoprene composition with Amberlyst 15 acid resin over 20 minutes or 12 hours. The longer contact time resulted in an increase in the amount of C10 aromatic compounds relative to C10 dimers.

TABLE 1

Compounds derived from treatment of gas-phase isoprene with Amberlyst 15 catalyst.

| Compound | Retention Time (min) and Mass Spectra (m/z) |
|---|---|
| 2-methyl-3-buten-2-ol | 3.18 min; m/z 71, 59, 43 |
| 3-methyl-2-butanone | 3.73 min; m/z 86, 71, 43 |
| 2-methylbutanal | 3.79 min; m/z 86, 71, 43 |
| 3-methyl-2-buten-1-ol | 4.98 min; m/z 86, 68, 56, 41 |
| 1-methyl-4-(isopropylidene)cyclohexene* | 7.23 min; m/z 136, 121, 105, 93, 77, 43 |
| Isopropyltoluene (3- and 4-) | 7.283 min; m/z 134, 119, 91 |
| 1,8-cineole (1,3,3-trimethyl-2-oxabicyclo-[2,2,2]octane) | 7.385 min; m/z 154, 139, 111, 81, 43 |
| 1-methyl-4-(isopropyl)-1,4-cyclohexadiene* | 7.525 min; m/z 136, 121, 105, 93, 77, 43 |
| $C_{10}H_{16}$ isoprene dimers | 7.765, 8.052 min; m/z/136 |
| 4-acetyl-1-methylcyclohexane | 8.070 min; m/z 138, 123, 95, 67, 43 |
| α-terpenol (2-(4-methylcyclohex-3-en-1-yl)-propan-2-ol) | 8.485 min; m/z 136, 121, 93, 81, 67, 59 |
| $C_{15}H_{24}$ isoprene trimers (linear and cyclic) | 9-10.5 min; m/z 204, 161, 133, 119 |
| $C_{15}H_{24}$ isoprene tetramers (linear and cyclic) | 11-13 min; m/z 272, 204, 161, 133, 119 |

*Or $C_{10}H_{16}$ hydrocarbon isomer. Structural assignments made on the basis of best MS spectral match to the NIST2.0 GC/MS library using Chemstation software (Agilent).

In another embodiment, a gas-phase isoprene composition is converted in to oxygenated isoprene derivatives (e.g., alcohols, esters, carboxylic acids, ketones, ethers, aldehydes, oxiranes, pyrans, etc.) through contact with a catalyst and an oxygen source. The oxygen source can be oxygen, hydrogen peroxide, water, carbon dioxide, or other oxygen-containing molecule. The conversion of gas-phase isoprene compositions into oxygenated derivatives can be catalyzed by an acidic catalyst, an organometallic catalyst, or any other suitable catalyst. For example, a gas-phase isoprene composition can be treated with 10% phosphoric acid on silica gel to produce a mixture of oxygenated compounds with molecular formulas $C_5H_{10}O$ and $C_{10}H_{18}O$), in addition to minor amounts of isoprene dimers and trimers (See Example 6, FIG. 17). The major products of this conversion are listed in the Table 2.

TABLE 2

Compounds derived from treatment of gas-phase isoprene with 10% $H_3PO_4$ on silica.

| Compound | Retention Time (min) and Mass Spectra (m/z) |
|---|---|
| 2-methyl-3-buten-2-ol | 3.18 min; m/z 71, 59, 43 |
| 3-methyl-2-butanone | 3.73 min; m/z 86, 71, 43 |
| 3-methyl-3-buten-1-ol | 4.51 min; m/z 86, 68, 56, 41 |
| 3-methyl-2-buten-1-ol | 4.98 min; m/z 86, 71, 53, 41 |
| 2H-pyran, 2-ethenyltetrahydro-2,6,6-trimethyl- | 6.859 min; m/z 139, 121, 93, 71, 43 |
| 1,4-cineole (1-Isopropyl-4-methyl-7-oxabicyclo[2.2.1]heptanes) | 7.206 min; m/z 154, 139, 125, 111, 71, 55, 43 |
| Isopropyltoluene (3- and 4-) | 7.283 min; m/z 134, 119, 91 |
| 1,8-cineole (1,3,3-trimethyl-2-oxabicyclo-[2,2,2]octane) | 7.385 min; m/z 154, 139, 111, 81, 43 |
| 4-acetyl-1-methylcyclohexane | 8.070 min; m/z 138, 123, 95, 67, 43 |
| α-terpenol (2-(4-methylcyclohex-3-en-1-yl)-propan-2-ol) | 8.485 min; m/z 136, 121, 93, 81, 67, 59 |

Figure 18:
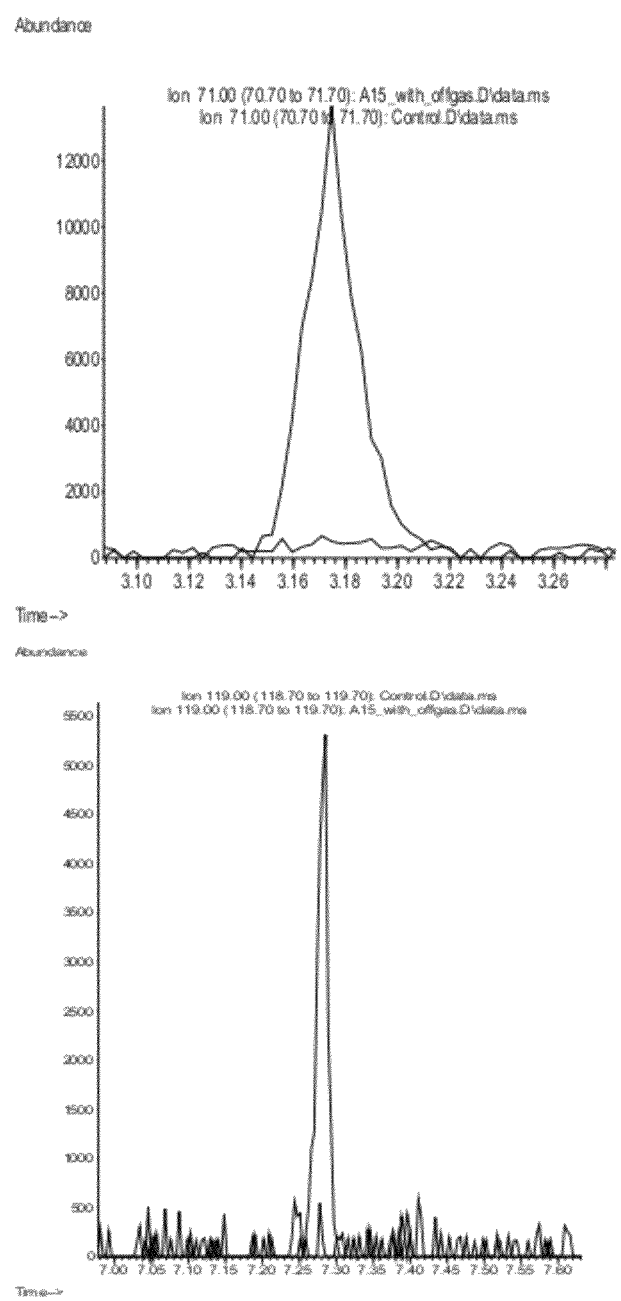
FIG. 18 shows GC/MS ion extracted chromatograms of the products derived from treatment of fermentation off-gas containing bioisoprene with Amberlyst 15 acid resin, compared to a control. 2-Methyl-3-buten-2-ol elutes at 3.18 minutes and isopropyltoluene elutes at 7.28 minutes.
Figure 19:
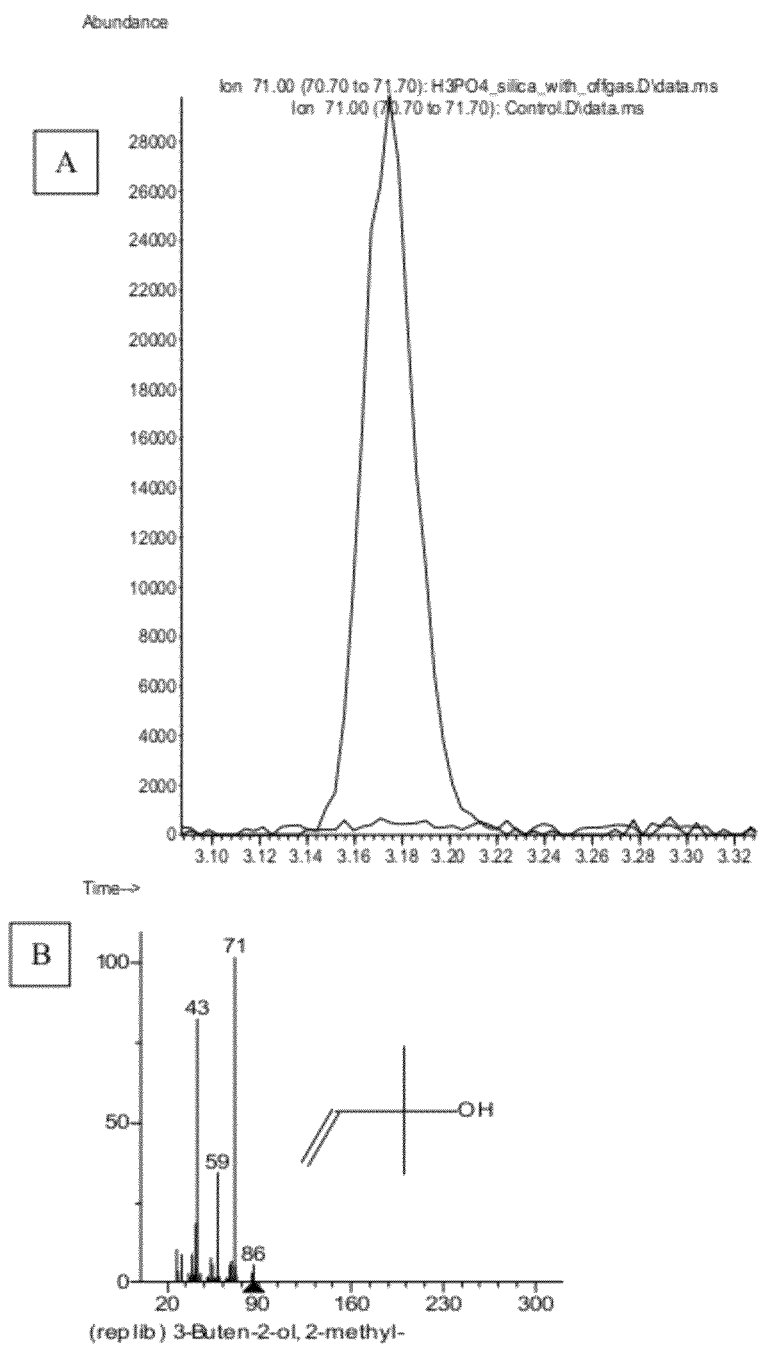
FIG. 19A shows a GC/MS ion extracted chromatogram of the products derived from treatment of fermentation off-gas containing bioisoprene with 10% $H_3PO_4$ on silica, compared to a control. 2-Methyl-3-buten-2-ol elutes at 3.18 minutes.
FIG. 19B shows a structure and mass spectrum of 2-methyl-3-buten-2-ol.

Treatment of fermentation off-gas containing bioisoprene with acid catalysts can result in conversion of a portion of the isoprene to isoprene derivatives at low isoprene concentrations, for example, under 0.02% v/v. Example 7 described the conversion of isoprene in a fermentation off-gas stream to isoprene derivatives using either Amberlyst 15 acid resin or 10% $H_3PO_4$ on silica. The concentration of isoprene in the off-gas stream was approximately 0.02% v/v. The results are shown in FIGS. 18 and 19.

Vapor Pressure

Another factor for consideration is vapor pressure. Typically, vapor pressure is measured in Reid Vapor Pressure (RVP). The fuel constituents of the invention generally have a Reid vapor pressure (RVP) of under 1 psi (6.9 kPa) and thus can be used to reduce vapor pressure in blends for fuel compositions. The RVP of gasoline is regulated according to the Reformulated Gasoline (RFG) Regulatory Requirements dictated by the US EPA. Summer gasoline blends can have a maximum RVP of 9 psi in most states, but cannot exceed 7 psi in some jurisdictions. Fuel constituents with low RVP values are valuable as blending components for the purpose of reducing the RVP value of the resulting fuel blend. See, for example, "Guide on Federal and State Summer RVP Standards for Conventional Gasoline Only" EPA420-B-05-012, November 2005 from the United States Environmental Protection Agency and Cruz et al., *Reactive & Functional Polymers* 67: 210-224 (2007).

The fuel constituents can also be used as a neat jet fuel or a constituent of a jet fuel In one embodiment, saturated, cyclic hydrocarbons in the C10 range are used as jet fuel constituents. Aromatic and unsaturated isoprene derivatives in the C5 to C20 can also be used as jet fuel constituents.

Other Catalysts

In addition to the acid catalysts and other catalysts (e.g., anionic catalysts) described above, shape-selective catalysts can be used as well. One of skill in the art can utilize the general teachings available in the field of shape selective catalysts for making fuel constituent products to minimize or otherwise alter the range of resulting products. See, e.g., Csicsery, et al., *Pure & Appl. Chem*. Vol. 58 No. 6, pp. 841-856 (1986). In particular, shape selective catalysts can be used to produce a desired class of fuel constituent from isoprene, for example isoprene dimers or trimers with reduced branching, or increased linear content. Shape selective catalysts are typically microporous inorganic materials (e.g. zeolites) with restricted pore geometry. The restricted nature of the catalyst structure tends to favor the formation of certain products over others. In one aspect of the invention, a shape selective catalyst is used to produce a C15 isoprene trimer with reduced amounts of branching for use as diesel fuel constituents.

Hydrogenation of Isoprene Derivatives

Any of the isoprene derivatives described herein can be subject to a hydrogenation step or the purpose of saturating carbon-carbon double bonds and the reduction of ketones, aldehydes and other reducible functionalities. Saturation of isoprene derivatives can improve their fuel properties by increasing their chemical stability and lower heating value (LHV) and reducing their ability to form gums and other undesirable byproducts. Hydrogenation of isoprene derivatives may be carried out using a variety of hydrogenation catalysts such as a heterogeneous palladium catalyst, including palladium on carbon (Pd/C), palladium on alumina (Pd/$Al_2O_3$), or palladium on silica (Pd/$SiO_2$) in grades ranging from 0.1% Pd to 20% Pd (w/w) relative to the support material. The hydrogen source can be hydrogen gas or a hydrogen equivalent, for example formic acid. Isoprene derivatives can be fully or partially hydrogenated for use as fuel constituents. A degree of unsaturation can increase the octane rating of a fuel constituent.

Systems and Compositions

Systems for the production of fuel constituents and/or fuel compositions are also contemplated within the scope of the invention.

In one aspect, the invention provides a system for producing a fuel constituent from a bioisoprene composition comprising a bioisoprene composition and: (a) (i) one or more catalysts for catalyzing metathesis of isoprene in the bioisoprene composition to form an olefin product; and (ii) a catalyst capable of hydrogenating the olefin product to form an alkane fuel constituent; (b) (i) a chemical capable of partially hydrogenating isoprene in the bioisoprene composition to produce an isoamylene, and (ii) a isoparaffin for alkylating the isoamylene derived from the bioisoprene composition to produce a fuel constituent; or (c) (i) a chemical capable of partially hydrogenating isoprene in the bioisoprene composition to produce an isoamylene, (ii) one or more catalysts for catalyzing metathesis of the isoamylene produced from partial hydrogenation of the bioisoprene composition to form an olefin product, and (iii) a catalyst capable of hydrogenating the olefin product to form an alkane fuel constituent; wherein a substantial portion of the isoprene in the bioisoprene composition is chemically converted to non-isoprene compounds.

In another embodiment, a system for producing a fuel constituent includes, but is not limited to, (a) a fermentation system comprising bioisoprene composition and (b) (i) one or more catalysts for catalyzing metathesis of isoprene in the bioisoprene composition to form an olefin product, and (ii) a catalyst capable of hydrogenating the olefin product to form an alkane fuel constituent. In another embodiment, a system for producing a fuel constituent includes, but is not limited to, (a) a fermentation system comprising bioisoprene composition and (c) (i) a chemical capable of partially hydrogenating isoprene in the bioisoprene composition to produce an isoamylene, and (ii) a isoparaffin for alkylating the isoamylene derived from the bioisoprene composition to produce a fuel constituent. In another embodiment, a system for producing a fuel constituent includes, but is not limited to, (a) a fermentation system comprising bioisoprene composition and (d) (i) a chemical capable of partially hydrogenating isoprene in the bioisoprene composition to produce an isoamylene, (ii) one or more catalysts for catalyzing metathesis of the isoamylene produced from partial hydrogenation of the bioisoprene composition to form an olefin product, and (iii) a catalyst capable of hydrogenating the olefin product to form an alkane fuel constituent. In any of the above embodiments, a substantial portion of the isoprene in the bioisoprene composition is chemically converted to one or more non-isoprene compounds.

The system can include a continuous fermentation system whereby bioisoprene composition is continuously produced. The off-gas containing the bioisoprene composition can be chemically transformed (e.g., catalysis of the off-gas, metathesis of isoprene in the bioisoprene composition, etc.) to produce fuel constituents that can be used for blending or making fuel compositions. Description of the isoprene content in bioisoprene composition of the gaseous phase is described infra.

In other embodiments, system can include other types of fermentation systems such as batch fermentation, fed-batch fermentation, and continuous with recycle processes fermentation. In another embodiment, chemical transformation of the isoprene can occur during any portion of the production, purification, recovery process, and/or post-recovery process. For example, as described in PCT/US2010/060552, the isoprene present in the recovery between adsorption and stripping may be chemically transformed to produce fuel constituents that can be used for blending or making fuel compositions.

In some embodiments, the metathesis catalyst for the system for producing a fuel constituent from a bioisoprene composition is any of the metathesis catalysts described herein, such as a chloride, oxide, or other compound containing Mo, Ru, W, Re, Os, Ir, Ti, V, Cr, Co, Nb, Rh, or Ta, a Schrock-carbene complex, a Grubbs-class catalyst, or a highly active ruthenium complex. In some embodiments, the SHOP method is used to carry out metathesis in the system. In some embodiments, the olefin metathesis catalyst for isoamylene metathesis is different from the olefin metathesis catalyst for bioisoprene metathesis. In some embodiments, the olefin metathesis catalyst for isoamylene metathesis is the same as the olefin metathesis catalyst for bioisoprene metathesis. In some embodiment, the hydrogenation catalyst for the system is any of the hydrogenation catalysts described herein, such as heterogeneous palladium catalysts including palladium on carbon (Pd/C), palladium on alumina (Pd/$Al_2O_3$), or palladium on silica (Pd/$SiO_2$) in grades ranging from 0.1% Pd to 20% Pd (w/w) relative to the support material. In some embodiments, the chemical capable of partially hydrogenating isoprene in the system is any of the partial hydrogenation catalysts described herein, such as Pd/$CaCO_3$, Pd/$BaSO_4$, Pd/C, Pd black, Pd/$SiO_3$, Pd/$Al_2O_3$, Pd/$SiO_2$, palladium-gold or palladium-silver catalysts, Mo/$Al_2O_3$, or an eggshell Pd/δ-$Al_2O_3$ catalyst. In some embodiments, the alkylation catalyst for the system is any of the alkylation catalysts described herein, such as hydrofluoric acid, sulfuric acid, a fluorosulfuric acid, a perhaloalkylsulfonic acid, an ionic liquid, or a mixture of Bronsted and/or Lewis acids. In some embodiments, the isoparaffin used for alkylation is isobutane or isopentane.

In one aspect, the invention provides a fuel constituent suitable for use as fuel such as an automobile fuel or aviation fuel. In another aspect of the invention, a bioisoprene composition is used as a starting material to generate products or mixtures of products that are useful as fuels or as intermediates for producing fuel constituents ("fuel intermediates"). In some embodiments, the fuel intermediate is of higher molecular weight than isoprene. In some embodiments, the fuel intermediate comprises mono-olefins, di-olefins or tri-olefins of higher molecular weight than isoprene, such as C6-C20, C7-C15, C10-C20, C6-C10, C11-C15, or C16-C20 olefins. In some embodiments, the fuel comprises fully saturated alkylates, such as C6-C20, C7-C15, C10-C20, C6-C10, C11-C15, or C16-C20 alkylates. The fuel or fuel intermediate may also be a mixture of saturated and unsaturated hydrocarbons. The fuel may comprise branched or straight-chain hydrocarbons. In some embodiments, at least 20, 40, 60, or 80% of the carbon atoms in the fuel are branched. In another embodiment, none of the carbon atoms in the fuel are branched. In a particular embodiment, some of the carbon atoms in the fuel are branched but none are quaternary carbons. In some embodiments, the fuel comprises oxygenates, such as 1, 2, 5, 10, 20, 30, 40, or 50% by weight of oxygenates. In other embodiments, the fuel is substantially free of oxygenates. In some embodiments, the fuel comprises at least 50, 60, 70, 80, 90, 95, or 99% by weight of C7-C15 hydrocarbons. In a particular embodiment, the C7-C15 hydrocarbons comprise some branched carbon atoms. In some embodiment, the fuel comprises at least 50, 60, 70, 80, 90, 95, or 99% by weight of C10-C20 hydrocarbons. In a particular embodiment, the C10-C20 hydrocarbons comprise no more than 50, 40, 30, 20, 10, 5, 2, or 1% branched carbon atoms. In some embodiments, the fuel has a high octane rating, such as an octane rating of 80-100, 80-90, 91-95, 95-100, or at least 80, 85, 90, 95, or 100. In some embodiments, the fuel has a high cetane rating, such as a cetane rating of 30-60, 40-60, or at least 30, 40, 50, 60, 70, or 80. In a particular embodiment, the fuel is useful as an automotive fuel, such as for an automobile that typically runs on diesel fuel or for an automobile that typically runs on non-diesel gasoline. In another particular embodiment, the fuel is useful as an aviation fuel. In some embodiments, the fuel may have certain properties that make it particularly useful as a fuel, such as low volatility, presence of oxygenates, absence of oxygenates, or resistance to freezing at low temperatures.

The starting bioisoprene compositions described herein are chemically transformed using each catalyst systems and reaction conditions disclosed in the references cited. Other catalysts and reaction conditions known in the art such as catalysts and reaction conditions applied to chemical transformations of 1,3-butadiene can be adapted to the isoprene starting compositions by one skilled in the art.

Removal of Dienes and Polymers from Fuel Products

Fuel compositions often contain unsaturated compounds (olefins, diolefins and polyolefins) that can form gums, resins, polymers and other undesirable byproducts over time (for example, see Pereira and Pasa (2006) *Fuel*, 85, 1860-1865 and references therein). In general, as the degree of unsaturation increases of a given compound, the more likely that compound is to form such byproducts. Isoprene is a 1,3-diene that readily forms undesirable polymeric byproducts when present in fuel compositions. While there exist fuel additives (anti-oxidants, radical quenchers etc.) that can reduce the extent of byproduct formation, such byproducts can still form over time. Olefins can also contribute to the formation of ground-level ozone when released into the atmosphere upon evaporation from fuels, or as the result of incomplete combustion of olefin-containing fuels.

Accordingly, fuel compositions derived wholly or in part from isoprene should contain little to no free isoprene. A range of methods can be used to either remove isoprene from fuel compositions, such as purification by distillation, reaction with alcohols to form ethers, or hydrogenation to convert isoprene to saturated derivatives. Alternately, isoprene can be treated with a dienophile such as malic anhydride producing inert adducts that do not contribute to the formation of undesirable byproducts.

In one embodiment, a fuel composition can refer to the fuel products which may also be blended or combined into mixtures to obtain an end product. For example, the fuel products may be blended to form gasoline of various grades, gasoline with or without additives, lubricating oils of various weights and grades, kerosene of various grades, jet fuel, diesel fuel, heating oil, and chemicals for making plastics and other polymers. Compositions of the fuel products described herein may be combined or blended with fuel products produced by other means.

Also provided are fuel compositions comprising isoprene derivatives that are substantially free of isoprene. In some embodiments, the fuel composition comprises less than 0.01%, 0.1%, 1%, 2%, 3%, 4%, 5%, 10% or 15% isoprene. Also provided are methods for chemically transforming a bioisoprene composition to a fuel composition comprising one or more isoprene derivatives that are substantially free of isoprene. In some embodiments, a substantial portion of the isoprene from the bioisoprene composition is converted to one or more fuel constituents. In some embodiments, a substantial portion of the isoprene from the bioisoprene composition is converted to one or more intermediates that can be further converted to produce one or more fuel constituents. In some embodiments, a substantial portion of the isoprene from the bioisoprene composition is converted to one or more compounds other than isoprene.

In some instances, isoprene and other conjugated dienes can form one or more polymeric products with gum-like consistencies that can reduce the yields of desired products and/or deactivate catalysts. (See, e.g., R. C. C. Pereira and V. M. D. Pasa. *Fuel* 85 (2006) 1860-1865.) In some embodiments, methods are provided for determining the amount of conjugated diene present in a product mixture. D. F. Andrade et al. describe various methods for determining the amount of conjugated diene present (*Fuel* (2010), doi:10.106/j.fuel/2010.01.003), including the following: 1) UOP-326 method (maleic anhydride method), a semi-quantitative method in which the amount of maleic anhydride consumed via Diels-Alder reaction with the diene is measured; 2) polarography; 3) gas chromatography, in which the diene may be reacted with a derivatization agent, such as 4-methyl-1,2,4-triazoline-3,5-dione (MTAD) or 4-phenyl-1,2,4-triazoline-3,5-dione (PTAD); 4) HPLC; 5) supercritical fluid chromatography; 6) NMR; 7) UV and near IR spectroscopy; and 8) other spectroscopic methods, which may include first derivatizing the diene with p-nitrobenzenediazonium fluoroborate.

Methods are provided herein for minimizing gum-formation and/or reducing the amount of gum that has been produced. In some embodiments, an anti-oxidant is used to minimize gum-formation. In other embodiments, polymeric by-products are recycled back to the process stream. In some embodiments, depolymerization of polymeric by-products is carried out via olefin metathesis. Olefin metathesis can be carried out using a molybdenum or tungsten catalyst, such as 2,6-diisopropylphenylimido neophylidene molybdenum bis(2-tertbutylphenoxide). (See U.S. Pat. No. 5,446,102; "Metathesis polymerization of olefins and polymerization of alkynes", Y. Imamoglu, Ed., NATO ASI Series, Series C: Mathematical and Physical Sciences, Vol. 506, pp. 133-134.)

In some embodiments, any of the methods described herein further include characterizing one or more of the products of these reactions and assessing the potential fuel value. For example, the products can be characterized by standard methods known in the art, e.g., GC/MS, NMR, UV-Vis and IR spectroscopies, boiling temperature, density and other physical properties. The products can be further characterized by dual carbon-isotopic fingerprinting (see, U.S. Pat. No. 7,169,588). The potential fuel value of the products can be assessed by one or more parameters measuring fuel properties, such as the energy density, heating value, water solubility, octane/cetane number, density, viscosity, surface tension, enthalpy of vaporization, vapor diffusivity, flash point, autoignition point, flammability limits, cloud point and chemical stability.

As with commercial petroleum fuels, fuel products derived from isoprene from a bioisoprene composition can be tested for their acidity, density, trace mineral content, benzene, total aromatics content, water content, and corrosivity. To assure that minor impurities in fuel products derived from isoprene from a bioisoprene composition are not adversely affecting their material properties, samples can also be tested for their corrosivity and compatibility with fuel systems by standard ASTM tests such as Karl Fischer for water and copper strip for corrosivity.

Carbon Fingerprinting

Fuels derived from isoprene from a bioisoprene composition can be distinguished from fuels derived from petrochemical carbon on the basis of dual carbon-isotopic fingerprinting. Additionally, the specific source of biosourced carbon (e.g., glucose vs. glycerol) can be determined by dual carbon-isotopic fingerprinting (see U.S. Pat. No. 7,169,588, which is herein incorporated by reference).

This method usefully distinguishes chemically-identical materials, and apportions carbon in products by source (and possibly year) of growth of the biospheric (plant) component. The isotopes, $^{14}C$ and $^{13}C$, bring complementary information to this problem. The radiocarbon dating isotope ($^{14}C$), with its nuclear half life of 5730 years, clearly allows one to apportion specimen carbon between fossil ("dead") and biospheric ("alive") feedstocks [Currie, L. A. "Source Apportionment of Atmospheric Particles," Characterization of Environmental Particles, J. Buffle and H. P. van Leeuwen, Eds., 1 of Vol. I of the IUPAC Environmental Analytical Chemistry Series (Lewis Publishers, Inc) (1992) 3 74]. The basic assumption in radiocarbon dating is that the constancy of $^{14}C$ concentration in the atmosphere leads to the constancy of $^{14}C$ in living organisms. When dealing with an isolated sample, the age of a sample can be deduced approximately by the relationship t=(−5730/0.693)ln(A/$A_O$) (Equation 14) where t=age, 5730 years is the half-life of radiocarbon, and A and $A_O$ are the specific $^{14}C$ activity of the sample and of the modern standard, respectively [Hsieh, Y., Soil Sci. Soc. Am J., 56, 460, (1992)]. However, because of atmospheric nuclear testing since 1950 and the burning of fossil fuel since 1850, $^{14}C$ has acquired a second, geochemical time characteristic. Its concentration in atmospheric $CO_2$—and hence in the living biosphere—approximately doubled at the peak of nuclear testing, in the mid-1960s. It has since been gradually returning to the steady-state cosmogenic (atmospheric) baseline isotope rate ($^{14}C/^{12}C$) of ca. $1.2 \times 10^{-12}$, with an approximate relaxation "half-life" of 7-10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C$, $^{12}C$ isotope ratio HOxI (referenced to AD 1950). This is roughly equivalent to decay-corrected pre-Industrial Revolution wood. For the current living biosphere (plant material), $f_M \approx 1.1$.

The stable carbon isotope ratio ($^{13}C/^{12}C$) provides a complementary route to source discrimination and apportionment. The $^{13}C/^{12}C$ ratio in a given biosourced material is a consequence of the $^{13}C/^{12}C$ ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway. Within the precision of measurement, $^{13}C$ shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "$C_3$" (or Calvin-Benson) photosynthetic cycle and those that incorporate the "$C_4$" (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphoenol-pyruvate carboxylase, is the primary carboxylation reaction. The first stable carbon compound is a 4-carbon acid which is subsequently decarboxylated. The $CO_2$ thus released is refixed by the $C_3$ cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) [Weber et al., J. Agric. Food Chem., 45, 2942 (1997)]. Coal and petroleum fall generally in this latter range. The $^{13}C$ measurement scale was originally defined by a zero set by pee dee belemnite (PDB) limestone, where values are given in parts per thousand deviations from this material. The "$\delta^{13}C$", values are in parts per thousand (per mil), abbreviated ‰, and are calculated as follows:

$$\delta^{13}C \equiv \frac{(^{13}C/^{12}C)_{sample} - (^{13}C/^{12}C)_{standard}}{(^{13}C/^{12}C)_{standard}} \times 100\%$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

For isoprene derived from extractive distillation of $C_5$ streams from petroleum refineries, δ13C is about −22‰ to about −24‰. This range is typical for light, unsaturated hydrocarbons derived from petroleum, and products derived from petroleum-based isoprene typically comprise isoprenic units with the same $\delta^{13}C$. Isoprene from a bioisoprene composition produced by fermentation of corn-derived glucose ($\delta^{13}C$ −10.73‰) with minimal amounts of other carbon-containing nutrients (e.g., yeast extract) produces isoprene which can be polymerized into polyisoprene with $\delta^{13}C$ −14.66‰ to −14.85‰. Products produced from such isoprene from a bioisoprene composition are expected to have $\delta^{13}C$ values that are less negative than those derived from petroleum-based isoprene. For isoprene derived from the reaction of isobutylene with formaldehyde, $\delta^{13}C$ values can be about −34.4‰ because formaldehyde is often derived from feedstocks with much more negative $\delta^{13}C$ values.

The fuels and fuel constituents of this invention which are made with isoprene from the cell cultures that utilize biorenewable carbon sources can be identified as such by virtue of their $\delta^{13}C$ values and other fuel characteristics. In some embodiments, the fuel constituent derived from isoprene from a bioisoprene composition has $\delta^{13}C$ values of greater (less negative) than −22‰. In some embodiments, the fuel constituent derived from isoprene from a bioisoprene composition has $\delta^{13}C$ values of greater than −20, −18, −16, −14, −12, or −10‰. In some embodiments, the fuel constituent derived from isoprene from a bioisoprene composition has a $\delta^{13}C$ value which is within the range of −22 to −10, −21 to −12, or −20 to −14‰. In some embodiments, the fuel constituent derived from isoprene from a bioisoprene composition has a $\delta^{13}C$ value which is within the range of −34 to −24, −34 to −25, −33 to −25, −32 to −24, −32 to −25, −31 to −25, −30 to −29, −30.0 to −29.5, −29.5 to −28.5, or −29.0 to −28.5‰.

In some embodiments, the fuel constituent derived from isoprene from a bioisoprene composition comprises radioactive carbon-14. In some embodiments, the $^{14}C/^{12}C$ ratio is greater than or about $1.0 \times 10^{-12}$, $1.05 \times 10^{-12}$, $1.1 \times 10^{-12}$, $1.15 \times 10^{-12}$, or $1.2 \times 10^{-12}$. In some embodiments, the fuel constituent derived from isoprene from a bioisoprene composition has an $f_M$ value of greater than or about 0.9, 0.95, 1.0, 1.05 or 1.1. In some embodiments, the fuel constituent derived from isoprene from a bioisoprene composition has an $f_M$ value of greater than or about 0.9, 0.95, 1.0, 1.05 or 1.1 and $\delta^{13}C$ values of greater (less negative) than −22‰. In some embodiments, the fuel constituent derived from isoprene from a bioisoprene composition has an $f_M$ value of greater than or about 0.9, 0.95, 1.0, 1.05 or 1.1 and a $\delta^{13}C$ value which is within the range of −22 to −10, −21 to −12, or −20 to −14‰. In some embodiments, the fuel constituent derived from isoprene from a bioisoprene composition has an $f_M$ value of greater than or about 0.9, 0.95, 1.0, 1.05 or 1.1 and a $\delta^{13}C$ value which is within the range of −34 to −24, −34 to −25, −33 to −25, −32 to −24, −32 to −25, −31 to −25, −30 to −29, −30.0 to −29.5, −29.5 to −28.5, or −29.0 to −28.5‰. In other embodiments, the fuel constituent and/or fuel composition is not any of the products described in US 2009/0087890.

The derivatives of isoprene from bioisoprene compositions and the associated fuels, intermediates, and mixtures may be completely distinguished from their petrochemical derived counterparts on the basis of $^{14}C$ ($f_M$) and dual carbon-isotopic fingerprinting, indicating new compositions of matter.

In some embodiments, the fuel constituent of the invention has an energy density higher than that of ethanol. In some embodiments, the fuel constituent boosts the cetane number of a fuel, e.g., a petroleum-based fuel. In some embodiments, the fuel constituent reduces emission of petroleum based fuels. In some embodiments, the fuel composition has an octane number in the range between about 80 to about 120. In some embodiments, the fuel composition has a cetane number in the range between about 30 to about 130.

The invention further provides methods for making a fuel composition comprising obtaining a petroleum distillate and adding a fuel constituent of the invention.

The invention can be further understood by reference to the following examples, which are provided by way of illustration and are not meant to be limiting.

EXAMPLES

Example 1

Recovery of Isoprene from Bioisoprene Compositions

Isoprene was made using the compositions and methods as described in WO 2009/076676 and WO 2010/003007. Isoprene was recovered from a set of four 14-L scale fermentations in a two-step operation involving stripping of isoprene from the fermentation off-gas stream by adsorption to activated carbon, followed by off-line steam desorption and condensation to give liquid isoprene.

Figure 6:
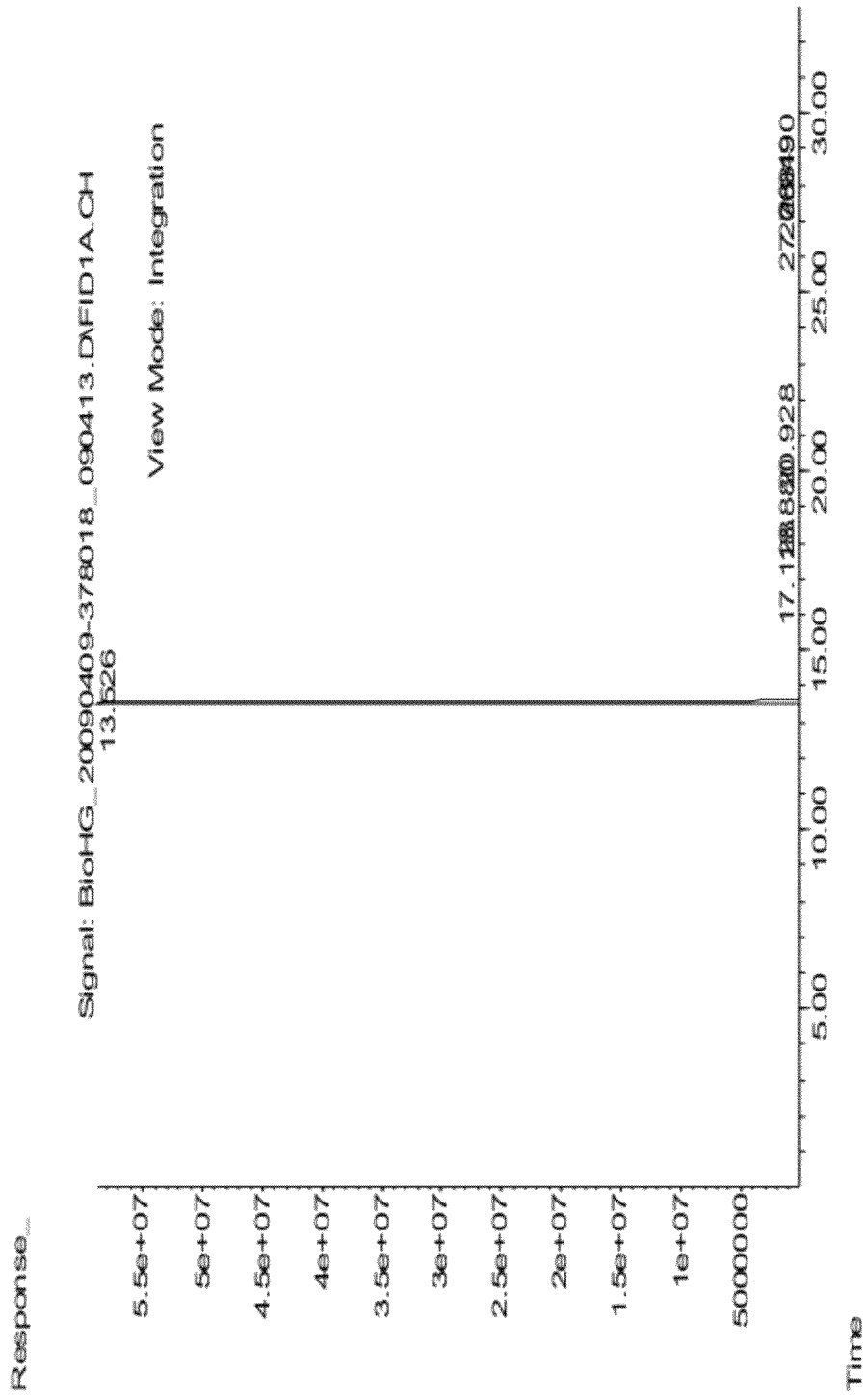
FIG. 6 shows a GC/FID chromatogram of a bioisoprene composition. The material was determined to be 99.7% pure.

Recovered isoprene liquid was analyzed by GC/MS and gas chromatography/flame ionization detection (GC/FID) to determine the nature and levels of impurities. The product was determined to be >99.5% pure and contained several dominant impurities in addition to many minor components. The GC/FID chromatogram is depicted in FIG. 6, and the typical levels of impurities are shown in Table 3. The impurity profile was similar to other batches of bioisoprene composition produced on this scale.

TABLE 3

Summary of the nature and levels of impurities seen in several batches of Bioisoprene composition.

| Compound | Retention Time (min) | | Conc. Range |
|---|---|---|---|
| | GC/MS | GC/FID | |
| Ethanol | 1.59 | 11.89 | <50 ppm |
| Acetone | 1.624 | 12.673 | <100 ppm |
| Methacrolein | 1.851 | 15.369 | <200 ppm |
| Methyl vinyl ketone | 1.923 | 16.333 | <20 ppm |
| Ethyl acetate | 2.037 | 17.145 | 100 to 800 ppm |
| 3-Methyl-1,3-pentadiene | 2.27 | 18.875 | 50 to 500 ppm |
| Methyl vinyl oxirane | 2.548 | 19.931 | <100 ppm |
| Isoprenol | 2.962 | 21.583 | <500 ppm |
| 3-methyl-1-butanol | 2.99 | 21.783 | <50 ppm |
| 3-hexen-1-ol | 4.019 | 24.819 | <100 ppm |
| Isopentenyl acetate | 4.466 | 25.733 | 200 to 1000 ppm |
| 3-hexen-1-yl acetate | 5.339 | 27.223 | <400 ppm |
| limonene | 5.715 | 27.971 | <500 ppm |
| Other cyclics | 5.50-6.50 | 27.5-28.0 | <200 ppm |

Purification of Isoprene from Bioisoprene Compositions by Treatment with Adsorbents Adsorbents are widely used by industry for the removal of trace impurities from hydrocarbon feedstocks. Suitable adsorbents include zeolite, alumina and silica-based materials. Isoprene from bioisoprene compositions can be substantially purified by passage over silica gel, and to a lesser extent with alumina. The Selexsorb™ adsorbent products from BASF is one of the adsorbents of choice for the removal of polar impurities from bioisoprene compositions. Specifically, the Selexsorb CD and CDX products are preferred given their proven utility for removal of polar impurities from isoprene and butadiene feedstocks. However, it is understood that other adsorbent products are contemplated within the scope of the invention.

Example 1A

Purification of BioIsoprene Compositions with Selexsorb® Adsorbents

Isoprene derived from a bioisoprene composition (1 mL with 150 ppm TBC added) was treated with one bead (diameter ⅛", ~90 mg) of either Selexsorb®CD, or Selexsorb® CDX in a GC vial for 1 hour with occasional agitation. The Selexsorb® products changed color from white to yellowish within 10 minutes. Samples were analyzed by GC/MS and the spectra overlaid to highlight the degree to which impurities were removed. The extent of polar impurity removal was determined and the results listed in Table 4.

TABLE 4

Extent of removal of polar impurities from bioisoprene using Selexsorb ® adsorbents.

| Compound | Selexsorb ® CD | Selexsorb ® CDX |
|---|---|---|
| Ethanol | >90% | >90% |
| Acetone | >90% | >90% |
| Methacrolein | >90% | >90% |
| Ethyl acetate | >90% | >90% |
| 3-Methyl-3-buten-2-ol | >90% | >90% |
| Methylvinyl ketone | >90% | >90% |
| 2-vinyl-2-methyloxirane | >90% | >90% |
| 3-methyl-3-buten-1-ol | 94% | 96% |
| 3-methyl-3-buten-1-yl acetate | 68% | 75% |

Example 2

Chemical Transformations of Isoprene from Bioisoprene Compositions

Chemicals and solvents were used as received from Sigma Aldrich Corp (WI, USA). Isoprene was produced by fermentation of *E. coli* BL21 strains expressing isoprene synthase and a heterologous mevalonic acid (MVA) isoprene precursor biosynthetic pathway. Isoprene from bioisoprene compositions was recovered from fermentation off-gas by adsorption to activated carbon, followed by steam desorption and condensation to obtain crude, liquid isoprene. Isoprene was purified by fractional distillation immediately before use.

$^1$H NMR Analysis

Proton ($^1$H) nuclear magnetic resonance (NMR) spectra were recorded on a Varian VNMRS 500 MHz NMR system. All NMR spectra are referenced to tetramethylsilane (TMS, 0 ppm) or chloroform ($CHCl_3$, 7.26 ppm) and peak frequencies were recorded in ppm unless otherwise specified. Samples were run in either deuterated chloroform ($CDCl_3$) or methanol ($CD_3OD$).

GC/MS Analysis

The analysis was performed using an Agilent 6890 GC/MS system interfaced with a CTC Analytics (Switzerland) CombiPAL autosampler operating in headspace mode.

Method A:

An Agilent HP-5MS GC/MS column (30 m×0.25 mm; 0.25 μm film thickness) was used for separation of analytes. The autosampler was set up to inject 1 μL of a liquid sample from a 10 μL liquids syringe. The GC/MS method utilized helium as the carrier gas at a flow of 1 mL/minute. The injection port was held at 250° C. with a split ratio of 20:1. The oven program began at 50° C. for 2 minutes, increasing to 225° C. at a rate of 25° C./min. followed by a 1 minute hold for a total run time of 10 minutes. The Agilent 5793N mass selective detector was run in scan mode from m/z 29 to 500. A solvent delay of 1.5 minutes was employed. Under these conditions isoprene (2-methyl-1,3-butadiene) was observed to elute at 1.675 minutes.

Method B:

An Agilent HP-5MS GC/MS column (30 m×0.25 mm; 1 μm film thickness) was used for separation of analytes. The autosampler was set up to inject 1 μL of a liquid sample from a 10 μL liquids syringe. The GC/MS method utilized helium as the carrier gas at a flow of 1 mL/minute. The injection port was held at 250° C. with a split ratio of 20:1. The oven program began at 50° C. for 2 minutes, increasing to 225° C. at a rate of 25° C./min. followed by a 6 minute hold for a total run time of 15 minutes. The Agilent 5793N mass selective detector was run in scan mode from m/z 29 to 300. A solvent delay of 1.35 minutes was employed. Under these conditions isoprene (2-methyl-1,3-butadiene) was observed to elute at 2.25 minutes. GC/MS method A was employed unless otherwise stated.

Method C:

An Agilent HP-5MS GC/MS column (30 m×0.25 mm; 0.25 μm film thickness) was used for separation of analytes. The autosampler was set up to inject 1 μL of a liquid sample from a 10 μL liquids syringe. The GC/MS method utilized helium as the carrier gas at a flow of 1 mL/minute. The injection port was held at 250° C. with a split ratio of 100:1. The oven program began at 50° C. for 2 minutes, increasing to 225° C. at a rate of 25° C./min. followed by a 1 minute hold for a total run time of 10 minutes. The Agilent 5793N mass selective detector was run in scan mode from m/z 29 to 500. A solvent delay of 1.5 minutes was employed. Under these conditions isoprene (2-methyl-1,3-butadiene) was observed to elute at 0.675 minutes.

GC/FID Analysis

The analysis was performed using an Agilent 6890 GC/FID system interfaced with a CTC Analytics (Switzerland) CombiPAL autosampler operating in liquid mode. An Agilent DB-Petro GC column (100 m×0.25 mm; 0.50 μm film thickness) was used for separation of analytes. The autosampler was set up to inject 1 μL of a liquid sample from a 10 μL liquids syringe. The GC/FID method utilized helium as the carrier gas at a flow of 1 mL/minute. The injection port was held at 200° C. with a split ratio of 50:1. The oven program began at 50° C. for 15 minutes, increasing to 250° C. at a rate of 25° C./min. followed by a 10 minute hold for a total run time of 33 minutes. The FID detector was held at 280° C. in Constant makeup mode with a hydrogen flow of 35 mL/min and air flow of 250 mL/min. Under these conditions isoprene (2-methyl-1,3-butadiene) was observed to elute at 13.54 minutes.

I. General Hydrogenation of Unsaturated Compounds

The mixture of unsaturated compounds is put in a glass chamber equipped with magnetic stirrer and containing an appropriate hydrogenation catalyst. All glassware is vacuum dried prior to carrying out the experiments. Hydrogen gas is introduced into the system and the pressure is kept at 3 atm. After several hours the catalyst is filtered from the reaction mixture and the products are separated using silica gel chromatography. Final analysis is done using GC-MS and NMR.

II. Complete Hydrogenation of Isoprene (A)

Isoprene (10 mL of a 10% solution in absolute ethanol (v/v)) was hydrogenated to 2-methylbutane (isopentane) in a continuous manner using an H-cube hydrogenation instrument (ThalesNano, Princeton, N.J., U.S.A.). The isoprene solution was pumped at 0.5 mL/min through a 10% Pd/C catalyst cartridge held at 70° C. Hydrogen gas was introduced using "full mode" at 1 atm pressure. The product was collected and analyzed by $^1$H NMR and GC/FID which confirmed the conversion of isoprene to 2-methylbutane in over 90% yield, in addition to minor amounts of partially hydrogenated mono-olefins. $^1$H NMR (500 MHz, CDCl$_3$): δ 0.8 (m, 9H, CH$_3$); 1.12 (m, 2H, CH$_2$); 1.37 (m, 1H, CH). GC/FID: 2-methylbutane; retention time=12.69 minutes.

(B)

Figure 7:
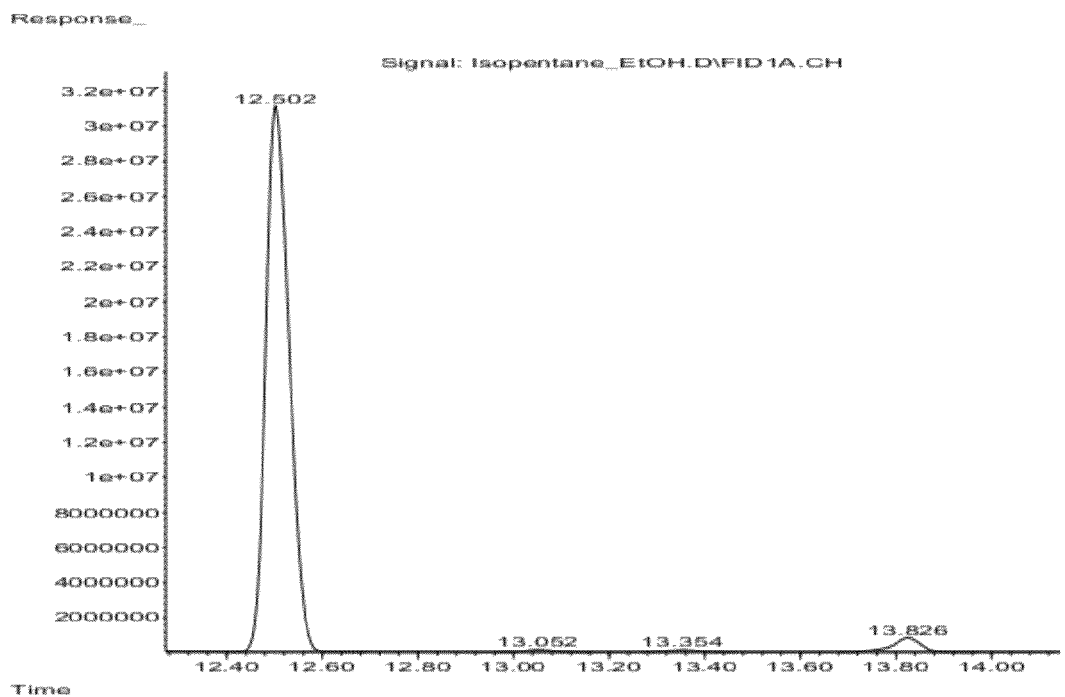
FIG. 7 shows a GC/FID chromatogram of the products of complete hydrogenation of isoprene derived from a bioisoprene composition. Isopentane (2-methylbutane) elutes at 12.502 minutes, 2-methyl-1-butene at 13.052 minutes, isoprene at 13.354 minutes and 2-methyl-2-butene at 13.826 minutes.

A 20% v/v solution of isoprene (100 ml) derived from a bioisoprene composition in absolute ethanol (400 mL) was hydrogenated to 2-methylpentane (isopentane) in a continuous manner using an H-Cube Midi™ hydrogenation instrument (ThalesNano, Princeton, N.J., U.S.A.). The isoprene solution was recirculated at a rate of 5 mL/min through a 5% Pd/C MidiCart™ catalyst cartridge held at a temperature of 70° C. and 30 bar pressure. Hydrogen was supplied at 125 mL/min in 'full' mode. The experiment was continued until excess hydrogen gas was observed at which point the majority of the product consisted of a solution of 2-methylbutane in ethanol as determined by GC/FID and $^1$H NMR spectroscopy (FIG. 7)

III. Partial Hydrogenation of Isoprene

Figure 8:
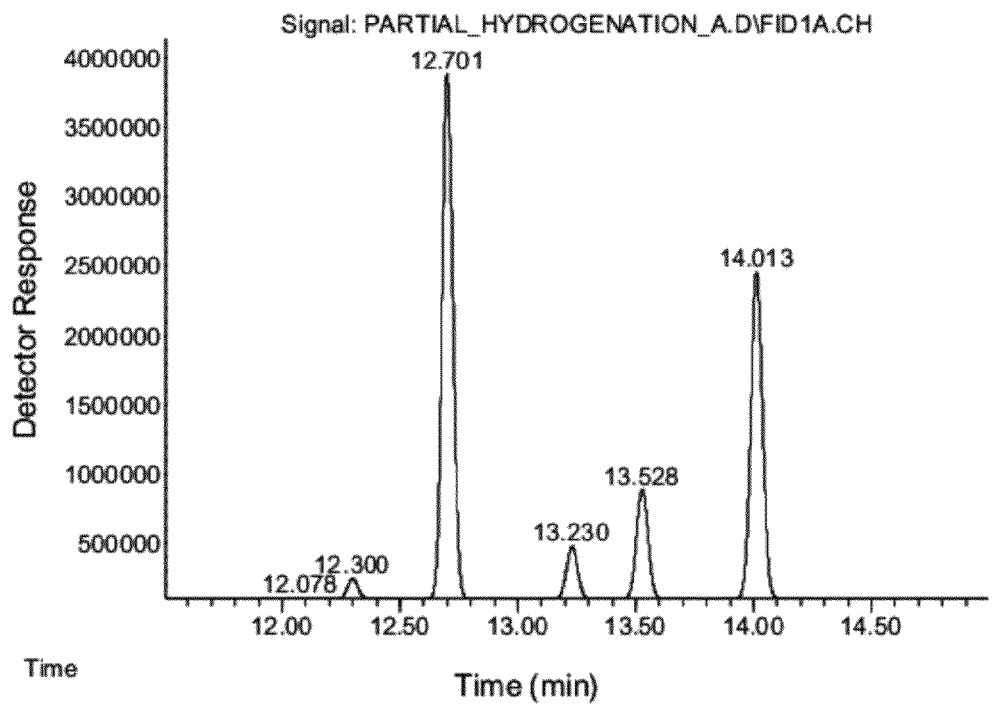
FIG. 8 shows a GC/FID chromatogram of partially hydrogenated bioisoprene composition. Compound 1 (RT=12.30 min)=3-methyl-1-butene, compound 2 (RT=12.70 min)=2-methylbutane, compound 3 (RT=13.23 min)=2-methyl-1-butene, compound 4 (RT=13.53 min)=isoprene, compound 5 (RT=14.01 min)=2-methyl-2-butene).

Isoprene that was obtained from biosoprene composition (50 mL, 0.5 mol) was mixed with toluene (200 mL) and partially hydrogenated over a 5% Pd/C catalyst on an Midi-Cube hydrogenation instrument (ThalesNano, Budapest, Hungary) at 40° C. and 5 bar hydrogen pressure. Substrate flow rate was 10 mL/min and hydrogen was delivered at 125 mL/min (5 mmol/min). The product stream was recycled through the instrument for a period of 2 hours after which time an aliquot of the product was analyzed by GC/MS and GC/FID which showed that the majority of the starting material had been converted to a mixture of isoamylenes (2-methyl-1-butene, 2-methyl-2-butene and 3-methyl-1-butene), in addition to isopentane and some unreacted isoprene (FIG. 8).

IV. Selective Hydrogenation of Isoprene (A)

Isoprene is selectively hydrogenated under the conditions cited in the above example using an eggshell Pd/δ-Al$_2$O$_3$ catalyst giving a mixture of isoamylenes where 2-methyl-2-butene is the dominant product accounting for >50% of the total isoamylenes and 3-methyl-1-butene is the minor product accounting for <25% of the total isoamylene products as determined by GC/MS analysis. The amount of isopentane and residual isoprene account for <10% of the total product stream. A similar result is obtained when a sulfided palladium on carbon catalyst is used to perform the reaction.

(B)

Figure 9:
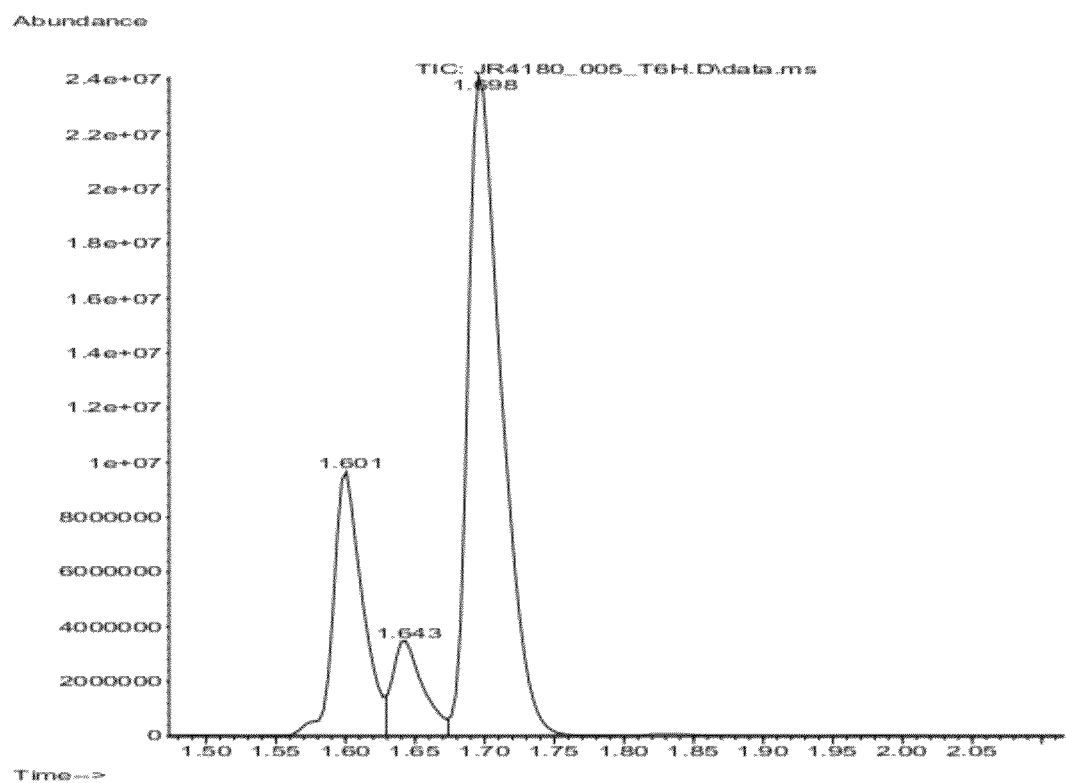
FIG. 9 shows a GC/MS chromatogram of the products of selective hydrogenation of isoprene derived from a bioisoprene composition. Isopentane (2-methylbutane) elutes at 1.601 minutes, 2-methyl-1-butene at 1.643 minutes and 2-methyl-2-butene at 1.698 minutes.

A mixture of isoprene (100 mL, 68.1 g, 1 mol) derived from a bioisoprene composition and water (50 mL) were circulated at a rate of 5 mL/min through a Thales-Nano H-Cube® Continuous-flow Hydrogenation Reactor containing a 5% Pd/Al$_2$O$_3$MidiCart™ catalyst cartridge held at a temperature of 30° C. and under 5 bar pressure for 6 hours. Hydrogen was supplied at 125 mL/min in 'full' mode. Analysis of the product by GC/MS indicated the conversion of the isoprene starting material into 2-methylbutane (isopentane) (~15%) and 2-methyl-2-butene (~85%). The GC/MS Total Ion Chromatogram is shown in FIG. 9.

(C)

A solution of isoprene (Sigma-Aldrich) (320 g) in toluene (1300 g) was passed through an activated, neutral alumina column to remove inhibitor. A Raney® cobalt 2724 hydrogenation catalyst (Grace Davison, USA) (12.8 g) was prepared by washing to neutral pH with deionized water, followed by displacement of water by washing the catalyst with isopropyl alcohol and then toluene. Hydrogenation was conducted in a Parr hydrogenation vessel at 4 to 7 bar pressure and a temperature of 80-85° C. after the addition of one molar equivalent of hydrogen gas. Analysis of the reaction product by GC/MS showed a mixture of isoamylenes (Table 5)

TABLE 5

Products of selective hydrogenation if isoprene with a Raney cobalt catalyst.

| Compound | Percent of total product |
|---|---|
| 3-methyl-1-butene | 29.4% |
| 2-methylbutane | 3.6% |
| 2-methyl-1-butene | 44.3% |
| isoprene | 5.4% |
| 2-methyl-2-butene | 17.3% |

V. Partial Hydrogenation of Isoprene from a Bioisoprene Composition in the Gas Phase A dry gas stream containing isoprene as part of a bioisoprene composition is mixed with a slight excess of hydrogen gas (mol/mol) and the gaseous mixture passed over a heterogeneous hydrogenation catalyst, such as a Group IB-promoted palladium catalyst with high pore volume as described in US Pat. Appl. 20090203520, to produce a mixture of isoamylenes and one or more impurities derived from the fermentation process from which the isoprene was originally derived. The conversion is carried out at pressures ranging from 0.5 to 200 bar, and temperatures from 0° C. to 200° C.

VI. Oligomerization of Isoprene from a Bioisoprene Composition with a Solid Acid Catalyst (A)

A mixture of isoprene (from bioisoprene composition) monomer (1.5 mL) and toluene (4 mL) was stirred at room temperature with Amberlyst 15 acid resin (186 mg) for 12 h at room temperature. An aliquot (500 uL) was removed from the reaction mixture and transferred to a GC vial. Analysis of the mixture was performed by GC/MS (FIG. 4) and revealed a complex mixture of products consisting of isoprene, linear, cyclic and aromatic C10, C15 and higher oligomers.

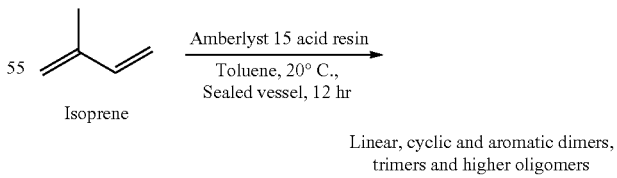

(B)

Figure 10:
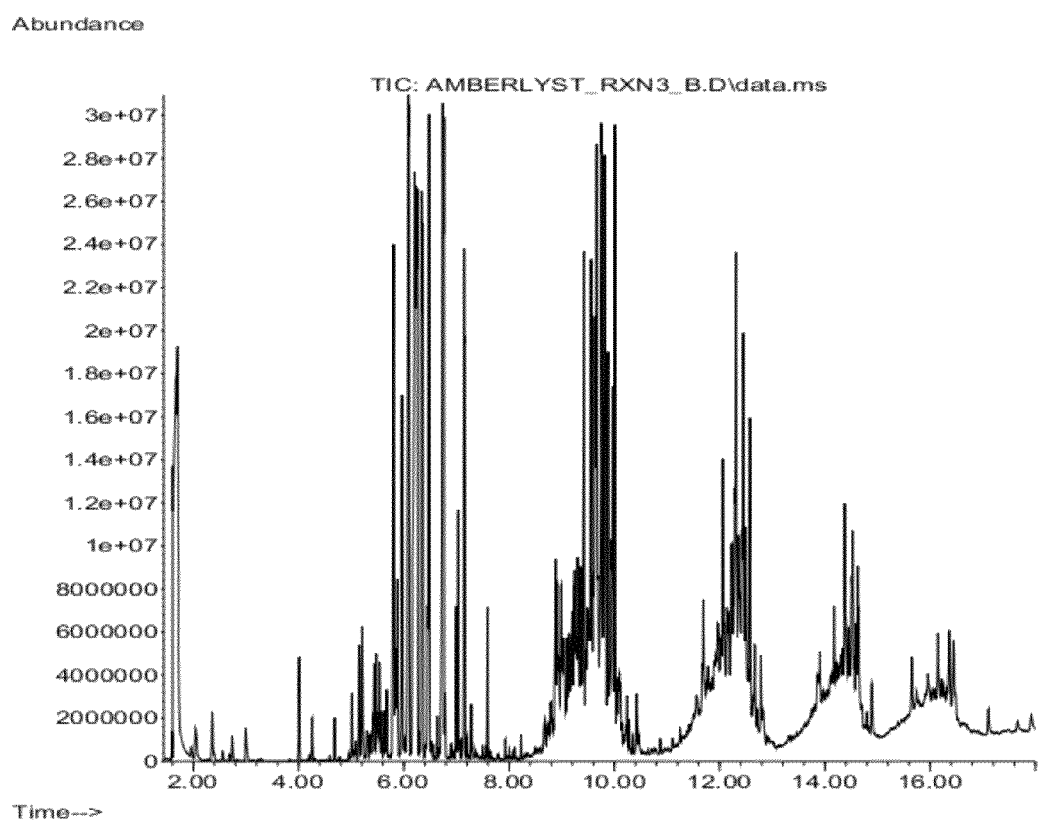
FIG. 10 is the total ion chromatogram showing products derived from oligomerization of isoprene after reflux through a bed of Amberlyst 15 acid resin. Isoprene dimers (10 carbons) elute between approximately 5 and 7.5 minutes, isoprene trimers (15 carbons) elute between 9 and 10.5 minutes, isoprene tetramers (20 carbons) elute between 11 and 13 minutes. Higher isoprene oligomers (>25 carbons) elute after 13 minutes.

Isoprene derived from a bioisoprene monomer (10 mL, 6.81 g) was placed into a 25 mL round bottom flask fitted with a 50 mL dropping funnel with side arm. A glycol cooled (−10° C.) reflux condenser was positioned on top of the dropping funnel and the entire apparatus was held under a blanket of nitrogen gas. The neck of the dropping funnel was plugged with cotton wool and Amberlyst 15 acid resin (2 g) added forming a bed approximately 1 cm thick. The round bottom flask was then placed in an oil bath held at 60° C. in order to bring the isoprene to reflux and resulted in recirculation of the isoprene through the Amberlyst resin bed. The experiment was continued for 2 hours resulting in the formation of a yellow solution in the flask. Analysis of the solution by GC/MS indicated the formation of a mixture of C10 dimers, C15 trimers and higher oligomers (FIG. 10). The mixture was less complex than that obtained through batch-mode oligomerization of BioIsoprene™ monomer (see FIG. 4), contained a greater proportion of C10 dimers, relative to higher isoprene oligomers, and had lower levels of aromatic compounds such as m- and p-cymene.

Figure 11:
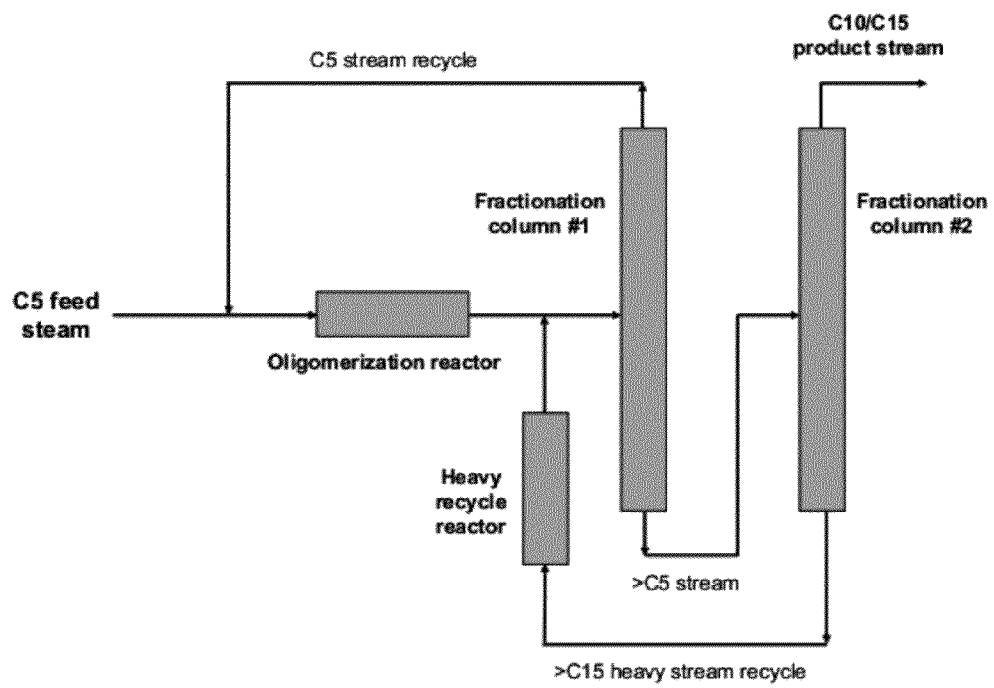
FIG. 11 shows a process flow diagram for the conversion of a C5 stream into a C10/C15 product stream using an oligomerization reactor. The C5 stream containing isoprene from a bioisoprene composition and/or C5 derivatives of isoprene from a bioisoprene composition.

VII. Continuous Oligomerization of Isoprene from a Bioisoprene Composition with a Solid Acid Catalyst Isoprene (from bioisoprene composition) monomer is continuously converted into C10 dimers and C15 trimers in a dimerization reactor containing Amberlyst 15 ion exchange resin or an equivalent catalyst. The feed stream of bioisoprene composition which includes isoprene monomer and optionally C5 derivatives of isoprene and a co-solvent. The process is conducted at temperatures ranging from 20 to 200° C. and pressures from 0.5 to 200 bars. The products of the dimerization step are fractionated in a first fractionation column to separate unreacted isoprene from higher (>C5) oligomers. The C5 fraction is returned to the dimerization reactor and the heavy >C5 fraction is introduced into a second fractionation column in which the desired C10/C15 fraction is collected from the overhead stream. The bottom fraction consisting of >C15 oligomers is fed into a heavy recycle reactor containing a metathesis catalyst such as the Grubbs $2^{nd}$ generation catalyst. The metathesis catalyst converts a portion of the higher oligomer fraction into lighter components by olefin cross-metathesis reactions that are subsequently fed into fractionation column #1 as depicted in FIG. 11.

Overall, the process results in conversion of isoprene monomer into C10 dimer and C15 trimer precursors for fuel constituents derived from biologically produced isoprene, which are then subjected to partial or complete hydrogenation under conditions described in example 2, section I. The resulting partially or fully saturated compounds are suitable as fuel compositions and as fuel blendstocks.

VIII. Metathesis of Isoprene from a Bioisoprene Composition to Mixtures of Higher and Lower Olefins Using the Grubbs $2^{nd}$ Generation Metathesis Catalyst

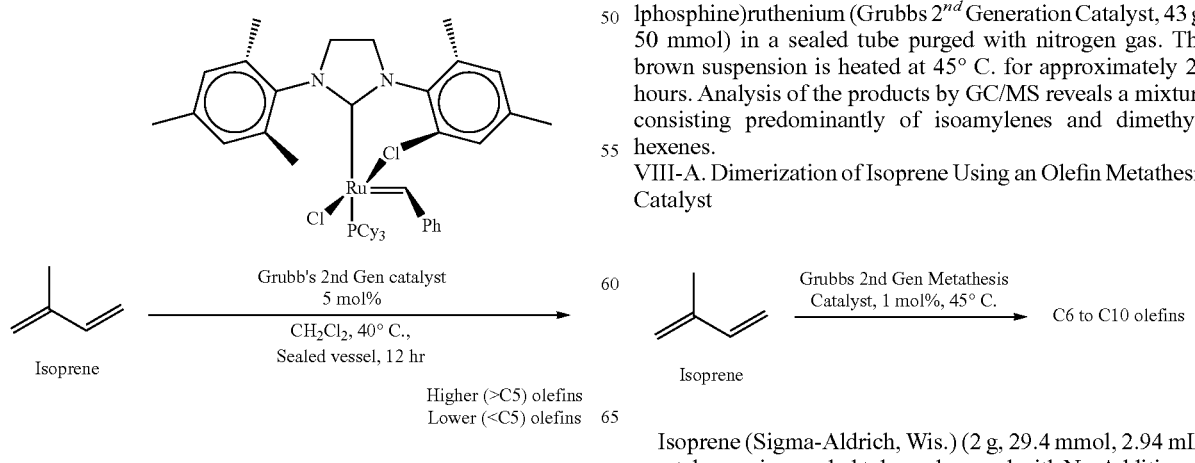

(A)

A bioisoprene composition (10 mL, 100 mmol), dichloromethane (40 mL) and the Grubbs 2nd Generation metathesis catalyst (CAS#246047-72-3) (250 mg) are placed in a 100 mL glass pressure vessel which is then sealed under nitrogen gas and held at 50° C. for 12 hr. An aliquot of the reaction mixture is withdrawn from the glass vessel and analyzed by GC/MS and GC/FID methods revealing the presence of a complex mixture of lower (<C5) and higher (>C5) olefins, in addition to unreacted isoprene. Fractional distillation of the mixture is performed to isolate the higher olefins, which are then subjected to partial or complete hydrogenation under conditions described in Example 2. The resulting partially or fully saturated compounds are suitable as fuel compositions and as fuel blendstocks.

The above example can also be performed with a mixture of a bioisoprene composition and other olefins such as isoamylenes derived from isoprene from a bioisoprene composition through partial hydrogenation. Olefins such as ethylene, propylene, 1,3-butadiene, isobutylene and higher olefins are also suitable as co-substrates. The reactions can be performed at temperatures between 20 and 200° C., at pressures ranging from 0.5 to 200 bars, with co-solvents and using both heterogeneous and homogenous catalysts.

Figure 3:
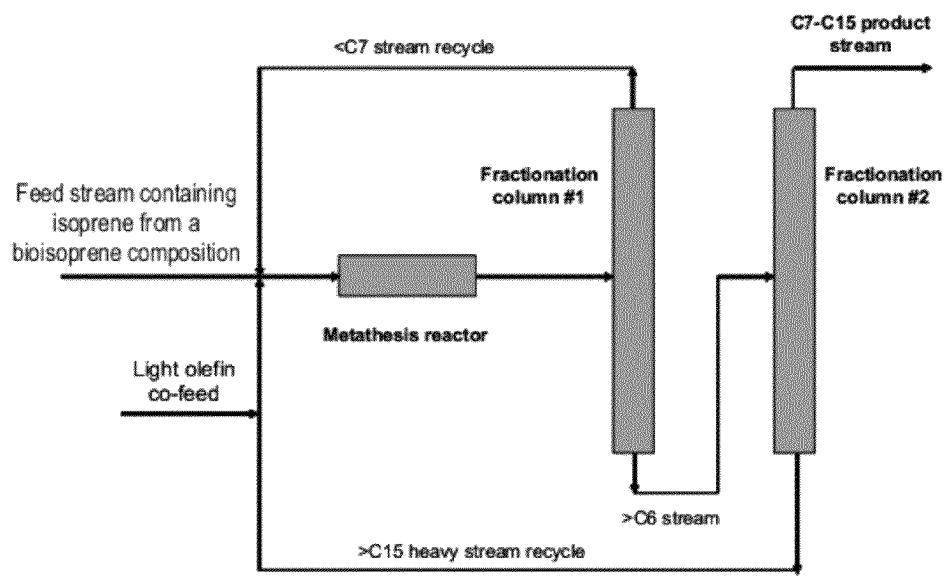
FIG. 3 shows a process flow diagram for the conversion of a bioisoprene composition stream into a C7-C15 fuel product stream using a continuous metathesis reactor.

At larger scales the cross-metathesis reaction is performed in a continuous manner analogous to the Shell Higher Olefin Process (SHOP), the Phillips Triolefin process and similar methods (see, e.g. Mol, J. C. (2004)). Isoprene from a bioisoprene composition is converted into a mixture of lower and higher olefins which are subsequently fractionated in one or more distillation towers. The desired fractions are removed for subsequent hydrogenation to fuel compounds and the higher and lower fractions, in addition to unreacted isoprene, are recycled to the metathesis reactor as shown in FIG. 3.

(B)

Isoprene derived from a bioisoprene composition (320 g, 4.7 mol) in toluene (1300 g) was passed through an activated, neutral alumina column to remove inhibitor. A Raney® cobalt 2724 hydrogenation catalyst (Grace Davison, USA) (12.8 g) was prepared by washing to neutral pH with deionized water, followed by displacement of water by washing the catalyst with isopropyl alcohol and then toluene. Hydrogenation was conducted in a Parr hydrogenation vessel at 4 to 7 bar pressure and a temperature of 80-85° C. after the addition of one molar equivalent of hydrogen gas.

The resulting mixture of isoamylenes (3-methyl-1-butene, 2-methyl-1-butene and 2-methyl-2-butene) is subjected to olefin metathesis using benzylidene[1,3-bis(2,4,6-trimethylphenyl)-2 imidazolidinylidene]dichloro(tricyclohexylphosphine)ruthenium (Grubbs $2^{nd}$ Generation Catalyst, 43 g, 50 mmol) in a sealed tube purged with nitrogen gas. The brown suspension is heated at 45° C. for approximately 24 hours. Analysis of the products by GC/MS reveals a mixture consisting predominantly of isoamylenes and dimethylhexenes.

VIII-A. Dimerization of Isoprene Using an Olefin Metathesis Catalyst

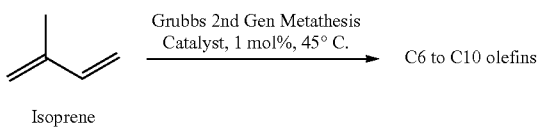

Figure 12:
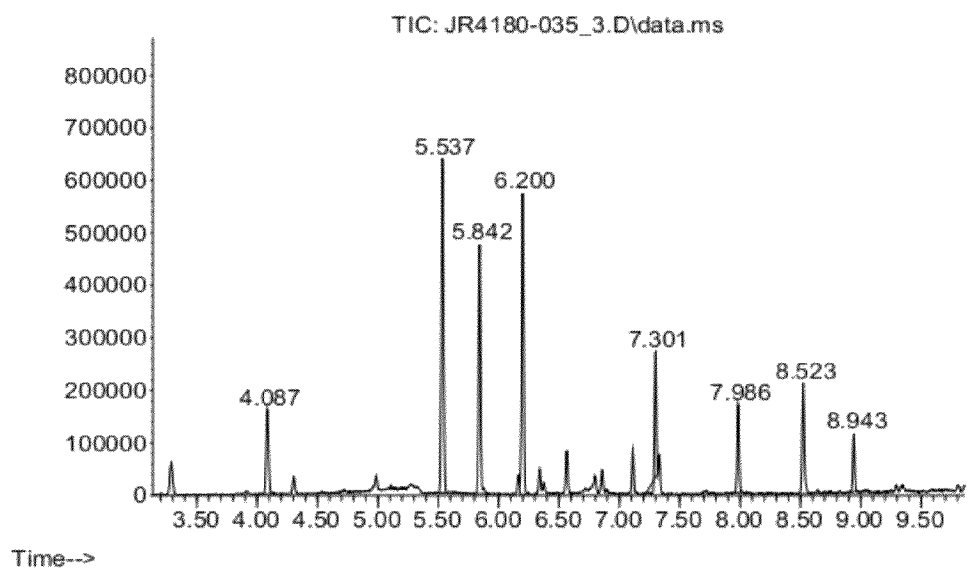
FIG. 12 shows a GC/MS chromatogram of the products of olefin metathesis of isoprene (2-methyl-1,3-butadiene). The mass spectra of the products are listed in Table 6.

Isoprene (Sigma-Aldrich, Wis.) (2 g, 29.4 mmol, 2.94 mL) was taken up in a sealed tube and purged with $N_2$. Addition of Benzylidene[1,3-bis(2,4,6-trimethylphenyl)-2-imidazolidinylidene]-dichloro(tricyclohexylphosphine)ruthenium-Grubbs 2$^{nd}$ generation catalyst (248 mg, 0.30 mmol) all at once was followed by stirring of the resulting burgundy-brown suspension at 45° C. for approximately 24 hours. The resulting dark brown suspension was found by GC/MS Method B (FIG. 12) to contain unreacted isoprene along with several higher molecular weight products identified as consisting of C6 to C10 olefins on the basis of their mass spectra. The mass spectra of the products are listed in Table 6.

TABLE 6

Mass spectra of the products of isoprene metathesis.

| Elution time (min) | Ions observed (m/z) | Carbon atoms |
|---|---|---|
| 4.087 | 96, 81 (BP), 79, 67 | 6 |
| 5.537 | 122, 107 (BP), 91, 79, 67 | 8 |
| 5.842 | 108. 93 (BP), 91, 77, 65 | 8 |
| 6.200 | 104 (BP), 78, 63 | 8 |
| 7.301 | 136, 121, 107, 93 (BP), 79, 68 | 10 |
| 7.986 | 164, 149, 135, 121, 107, 93, 79 (BP), 67 | 12 |
| 8.523 | 161, 148, 134, 119, 108, 93 (BP), 77 | 12 |
| 8.943 | 161, 144, 129 (BP), 115 | 12 |

BP = base peak

IX. Conversion of Isoprene from a Bioisoprene Composition to Fuel Products Using a Metathesis Reactor with Byproduct Recycling.

The conversion of isoprene from a bioisoprene composition to fuel products can be achieved using olefin metathesis (see, e.g., Mol, J. C. (2004)) whereby isoprene is converted to a mixture of higher olefins through the cleavage and reformation of carbon-carbon double bonds. A process flow diagram for the conversion of a stream of isoprene from a bioisoprene composition into a C7-C15 fuel product stream using a continuous metathesis reactor is shown in FIG. 3. The statistical distribution of products so obtained is fractionated in a first distillation column such that the overhead fraction consisting of light components (<C7) are returned to the metathesis reactor. These light components include ethylene, propylene, isobutylene, isoprene and other light olefins. The heavy fraction from the distillation column enters a second fractionation column where the desired linear and cyclic components in the C7 to C15 range are removed in the overhead fraction. These oligomers can be subjected to subsequent hydrotreating to produce fuel products derived from isoprene from a bioisoprene composition.

The heavy fraction from the second distillation column, consisting of C15 to C50 linear and cyclic oligomers, are recycled to the metathesis reactor where they are subjected to olefin disproportionation resulting in a distribution of products in the C2 to C50 range which are then fractionated by distillation as described above. The overall distribution of products produced in the metathesis reactor can be modulated through an optional light-olefin co-feed consisting of ethylene or mixtures of ethylene and other light olefins (<C5). The ratio of light olefin co-feed to feed of isoprene from a bioisoprene composition can range from 1:100 to 2:1. Higher light olefin co-feed to feed of isoprene from a bioisoprene composition ratios tend to lower the average molecular weight of the products and reduce the amount of undesired heavy fractions emerging from the metathesis reactor. A light olefin co-feed can also help prevent the formation of involatile gums and polymers (>C50) in the metathesis reactor that might otherwise deactivate the metathesis catalyst (see Oziomek U.S. Pat. No. 5,446,102).

X. Isoamylene Metathesis (A) Dimerization of 2-methyl-1-butene using an olefin metathesis catalyst Benzylidene[1,3-bis(2,4,6-trimethylphenyl)-2 imidazolidinylidene]dichloro-(tricyclohexylphosphine)ruthenium (Grubbs 2$^{nd}$ Generation Catalyst, 121 mg, 0.14 mmol) was taken up in a sealed tube and purged with nitrogen gas. Addition of 2-Methyl-1-butene (1 g, 1.54 mL, 14.3 mmol) was followed by heating the resulting brown suspension at 45° C. for approximately 24 hours. Analysis of the products by GC/MS Method B indicated the presence of unreacted 2-methyl-1-butene along with the formation of several minor products which included isomers of 3,4-dimethylhexene (m/z 69, 83, 97, 112).

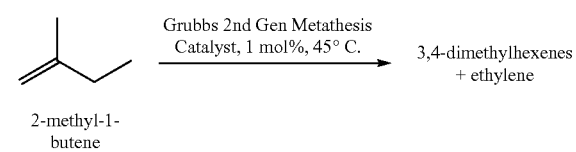

Figure 13A:
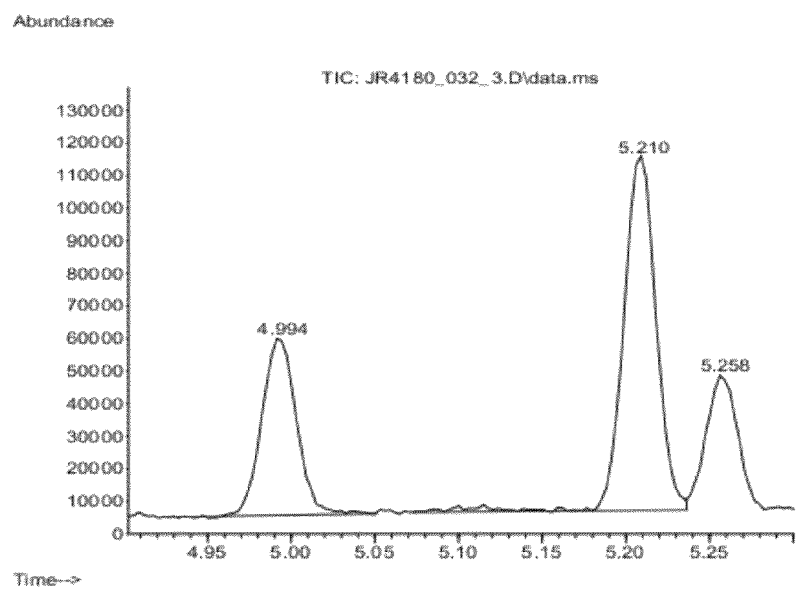
FIG. 13A shows a GC/MS chromatogram of the products of olefin metathesis of 2-methyl-1-butene. The peak at 4.994 minutes is a toluene impurity. The peaks at 5.210 and 5.258 minutes are metathesis products (see FIGS. 13B and 13B).
Figure 13B:
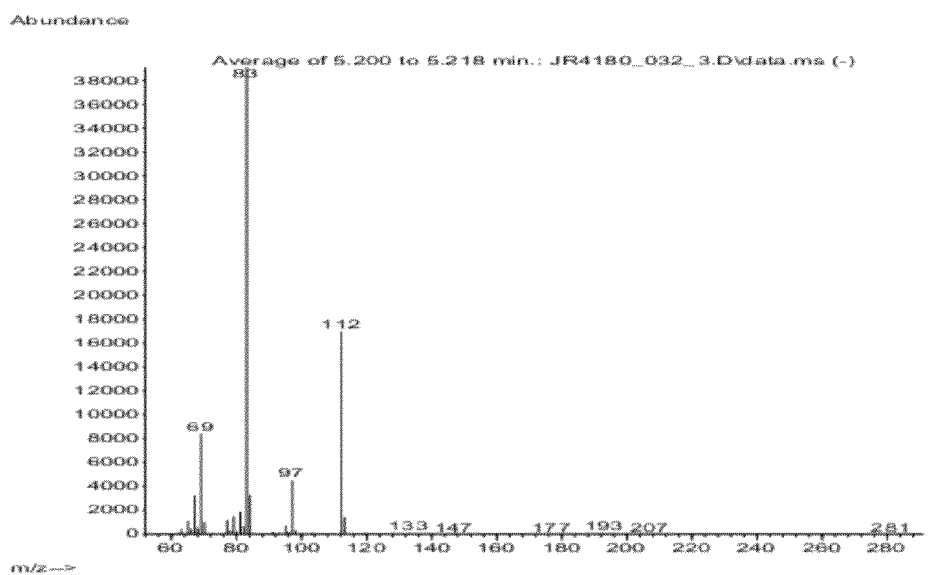
FIG. 13B shows the mass spectrum for the peak eluting between 5.200 and 5.215 minutes in the chromatogram depicted in FIG. 13A. The peak was identified as an isomer of 3,4-dimethyl-3-hexene using the NIST 2.0 GC/MS library.
Figure 13C:
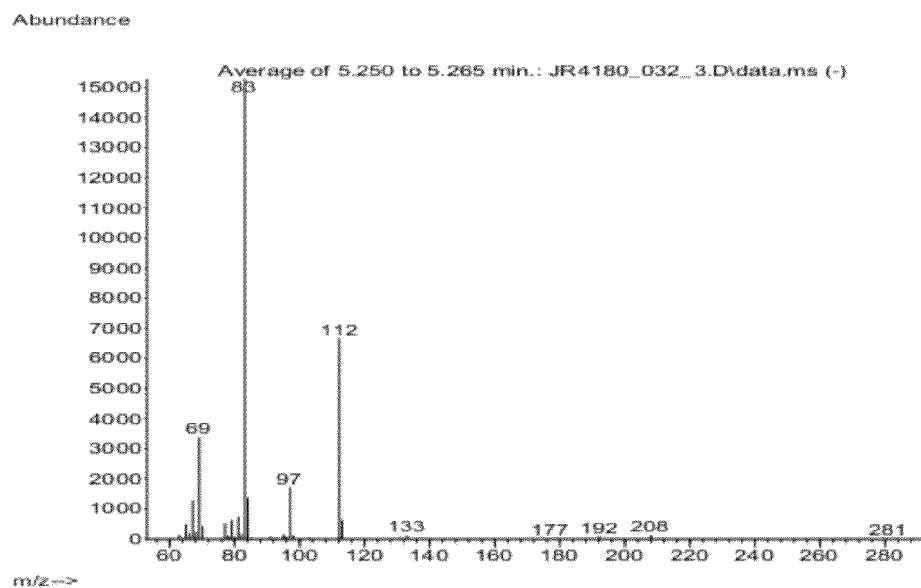
FIG. 13C shows the mass spectrum for the peak eluting between 5.250 and 5.265 minutes in the chromatogram depicted in FIG. 13A. The peak was identified as an isomer of 3,4-dimethyl-3-hexene using the NIST 2.0 GC/MS library.

The GC/MS Total Ion Chromatogram and the corresponding mass spectra for the major product peaks are shown in FIGS. 13A-C.

(B) Dimerization of 3-methyl-1-butene using an olefin metathesis catalyst

3-Methyl-1-butene (1.59 mL, 1 g, 14.3 mmol) was placed in a sealed tube and purged with N$_2$. Addition of Benzylidene [1,3-bis(2,4,6-trimethylphenyl)-2-imidazolidinylidene] dichloro(tricyclohexylphosphine)ruthenium (Grubbs 2$^{nd}$ generation catalyst) (121 mg, 0.14 mmol) all at once was followed by stirring of the resulting burgundy-brown suspension at 25° C. for approximately 24 hours. The resulting dark brown liquid was analyzed by GC/MS Method B and determined to contain dimethylhexenes as the major component (m/z 69, 97, 112).

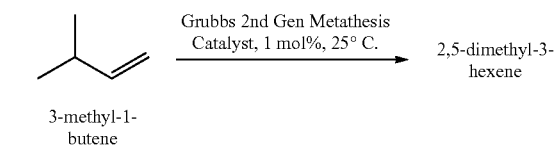

Figure 14A:
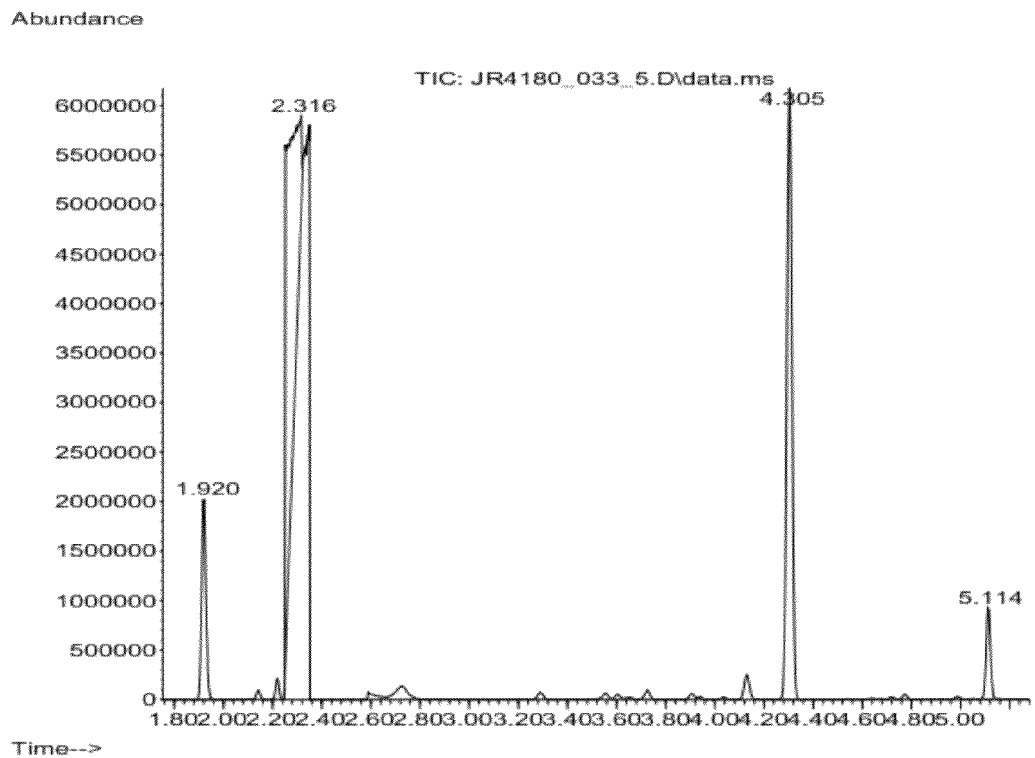
FIG. 14A shows a GC/MS chromatogram of the product of olefin metathesis of 3-methyl-1-butene. The peak at 4.305 minutes is a metathesis product (see FIG. 14B).
Figure 14B:
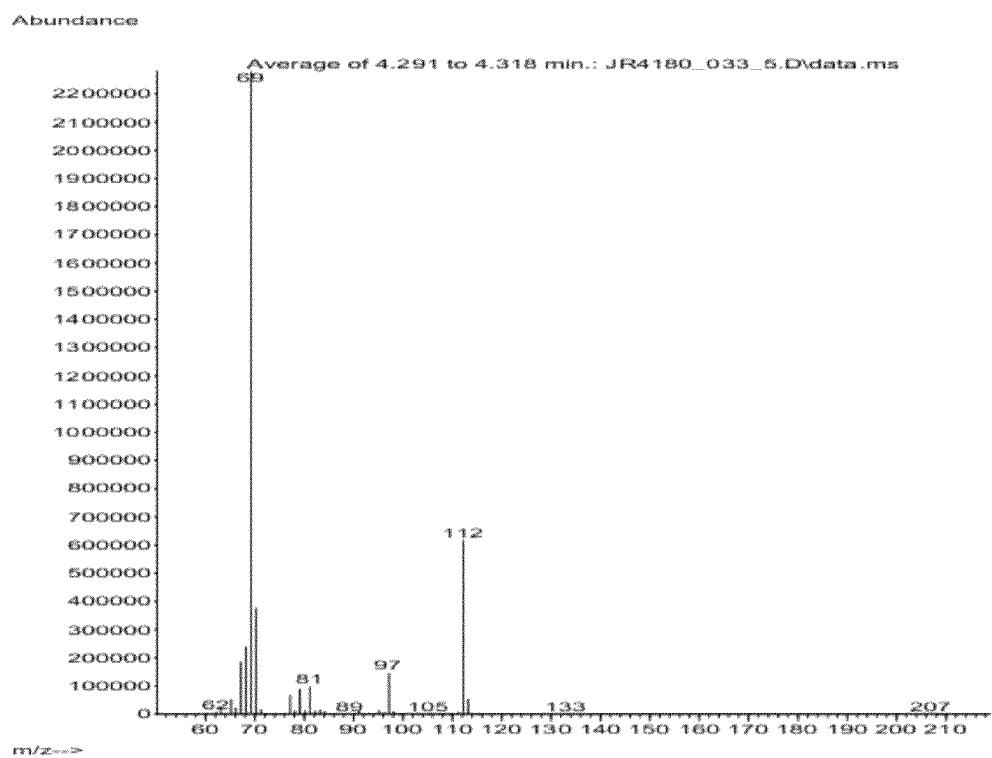
FIG. 14B shows the mass spectrum for the peak eluting between 4.291 and 4.318 minutes in the chromatogram depicted in FIG. 14A. The peak was identified as 2,5-dimethyl-3-hexene using the NIST 2.0 GC/MS library.

The GC/MS Total Ion Chromatogram and the corresponding mass spectrum for the major peak are shown in FIGS. 14A and 14B respectively.

Example 3

$^{13}$C/$^{12}$C Isotope Analysis $^{13}$C analysis can be done by loading 0.5 to 1.0 mg samples into tin cups for carbon isotopic analysis using a Costech ECS4010 Elemental Analyzer as an inlet for a ThermoFinnigan Delta Plus XP isotope ratio mass spectrometer. Samples are dropped into a cobaltous/cobaltic oxide combustion reactor at 1020° C. with combustion gases being passed in a helium stream at 85 mL/min through a copper reactor (650° C.) to convert NO$_x$ to N$_2$. CO$_2$ and N$_2$ are separated using a 3-m 5 Å molecular sieve column. Then, $^{13}C/^{12}C$ ratios are calibrated to the VPDB scale using two laboratory standards (Acetanilide B, −29.52±0.02‰ m and cornstarch A, −11.01±0.02‰) which have been carefully calibrated to the VPDB scale by off-line combustion and dual-inlet analysis using the 2-standard approach of T. B. Coplen et al, New Guidelines for $\delta^{13}C$ Measurements, Anal. Chem., 78, 2439-2441 (2006). The teachings of Coplen are incorporated herein by reference for the purpose of teaching the technique for determining $\delta^{13}C$ values.

U.S. Provisional Patent Application No. 61/133,521 filed on Jun. 30, 2008 and WO 2010/05525 A1 list $\delta^{13}C$ values for feedstock and polymers of isoprene derived from various sources, including ones listed in Table 7.

TABLE 7

| Sample | $\delta^{13}C$ |
|---|---|
| Palm oil | −30.00 |
| Yeast extract | −25.70 |
| Commercial polyisoprene from extractive distillation | −23.83 |
| Sugar from softwood pulp | −23.00 |
| Polyisoprene from Isoprene Sample B (emulsion polymerization) | −19.67 |
| Invert Sugar | −15.37 |
| Polyisoprene from Isoprene Sample A (Neodymium catalyst) | −14.85 |
| Glucose from bagasse | −13.00 |
| Glucose from corn stover | −11.20 |
| Cornstarch | −11.10 |
| Glucose | −10.73 |

Example 4

Exemplary Fuel Properties

Table 8 lists fuel properties of certain reference compounds and compounds that either can be made from a bioisoprene composition using methods described herein or compounds that have structures and/or fuel properties as listed in Table 8 similar to compounds that can be made from a bioisoprene composition using methods described herein.

TABLE 8

| | Formula | | MW (g/mol) | Boiling point (° C.) | Density (g/cm³) | Vapor pressure (Torr, 25° C.)* | ΔHc (kcal/mol) | Lower Heating Value (kBtu/gal) | Higher Heating Value (kBtu/gal) | Octane (Cetane) |
|---|---|---|---|---|---|---|---|---|---|---|
| α-Limonene | $C_{10}H_{16}$ | 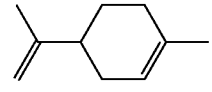 | 136.23 | 177 | 0.8477 | 1.54 | 1474 | 130.6 | 137.9 | 88 |
| 1-Methyl-4-isopropylcyclohexane | $C_{10}H_{20}$ | 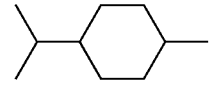 | 140.27 | 170.2 | 0.8060 | 2.16 | 1561 | 126.5 | 134.9 | 75 |
| 2,7-dimethyl-,(4E)-2,4,6-Octatriene | $C_{10}H_{16}$ | 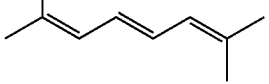 | 136.23 | 186.4* | 0.782 | 0.915 | 1481 | 121.1 | 127.8 | 110 |
| 2,7-dimethyl-octane | $C_{10}H_{22}$ | 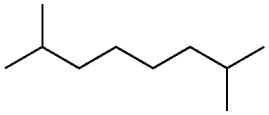 | 142.28 | 160 | 0.728 | 3.35 | 1620 | 116.5 | 124.7 | 97 |
| 3,7-dimethyl-1,5-cyclooctadiene | $C_{10}H_{16}$ |  | 136.23 | 182.7* | 0.860 | 1.09 | 1490 | 134.0 | 141.4 | 95 |
| 1,5-Dimethylcyclooctene (BIF-10) | $C_{10}H_{18}$ | 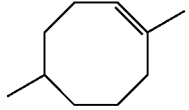 | 138.25 | 178.5* | 0.830 | 1.33 | 1545 | 131.6 | 139.4 | 90 |
| 1,5-Dimethylcyclooctane | $C_{10}H_{20}$ | 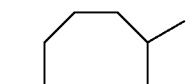 | 140.27 | 158.5 | 0.800 | 1.39 | 1560 | 125.4 | 133.8 | 85 |
| 2,6,11-Trimethyldodecane | $C_{15}H_{32}$ | 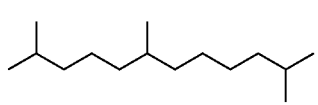 | 212.41 | 247.8* | 0.766 | 0.0396 | 2400 | 121.7 | 130.1 | (65) |

TABLE 8-continued

| | Formula | | MW (g/mol) | Boiling point (° C.) | Density (g/cm³) | Vapor pressure (Torr, 25° C.)* | ΔHc (kcal/mol) | Lower Heating Value (kBtu/gal) | Higher Heating Value (kBtu/gal) | Octane (Cetane) |
|---|---|---|---|---|---|---|---|---|---|---|
| Cyclodo-decane, 1,4,8-trimethyl | $C_{15}H_{30}$ | 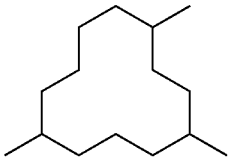 | 210.40 | 278.0* | 0.850 | 7.38E−3 | 2380 | 135.7 | 144.6 | (40) |
| BIF-15 | $C_{15}H_{31.5}$ | 3:1 mixture of linear and cyclic C15 | 211.9 | 255.4 | 0.787 | 0.0315 | 2395 | 125.2 | 133.7 | (58.8) |

Example 5

Figure 15A:
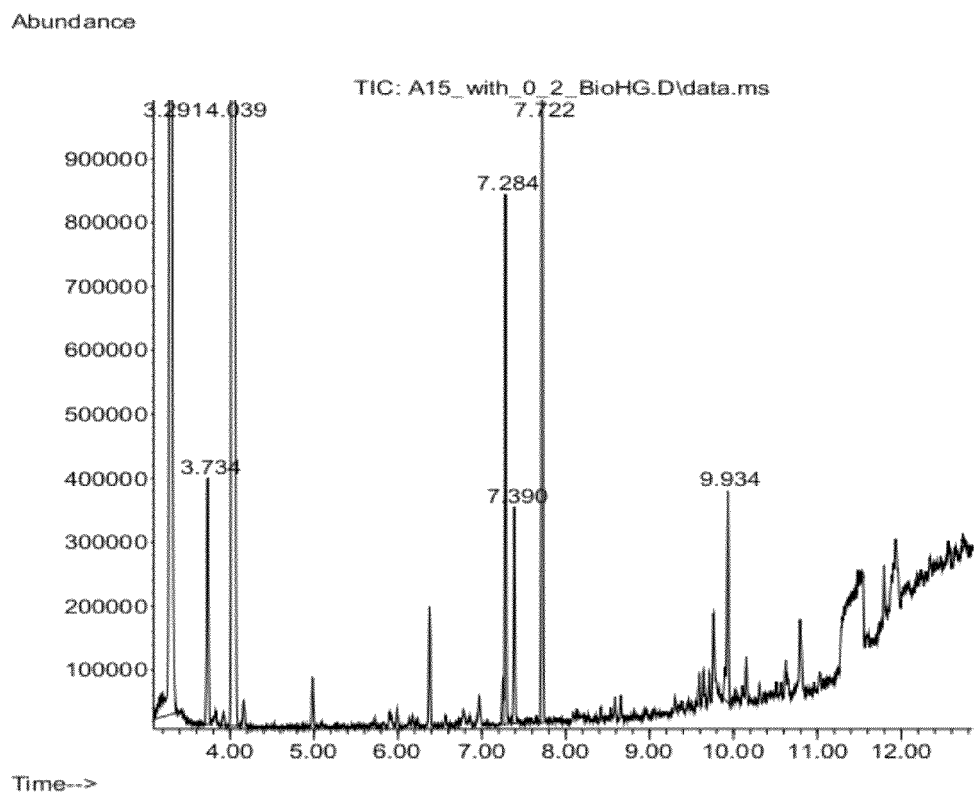
FIG. 15A shows a GC/MS chromatogram of products derived from the gas-phase reaction of isoprene (0.2% v/v) and Amberlyst 15 acid resin. 3-Methyl-2-butanone elutes at 3.734 minutes, isopropyltoluene (cymene) elutes at 7.284 minutes. Isoprene trimers elute at between 9.5 and 10.5 minutes. Peaks at 3.286, 4.035, 7.390 and 7.720 minutes are contaminants in the DCM injection solvent.

Gas-Phase Oligomerization of Isoprene Using Amberlyst 15, H⁺ Resin (A)
Amberlyst 15 acid resin (100 mg) was added to a 20 mL headspace vial (Agilent) filled with air. Isoprene monomer (0.2 µL) (from a bioisoprene composition) was injected into the vial and allowed to vaporize. The initial isoprene concentration was approximately 0.2% v/v. The vial was stored for 12 hours at room temperature, after which an aliquot of dichloromethane (DCM) (500 µL) was added to the vial and gently agitated for 1 minute. The DCM phase was then removed and added to a GC vial, followed by GC/MS analysis using method B. Several compounds were formed including 3-methyl-2-butanone (retention time=3.734 minutes), isopropyltoluene (RT 7.283 min) and isoprene trimers (RT 9 to 11 minutes). The results are depicted in FIG. 15A.

Figure 15B:
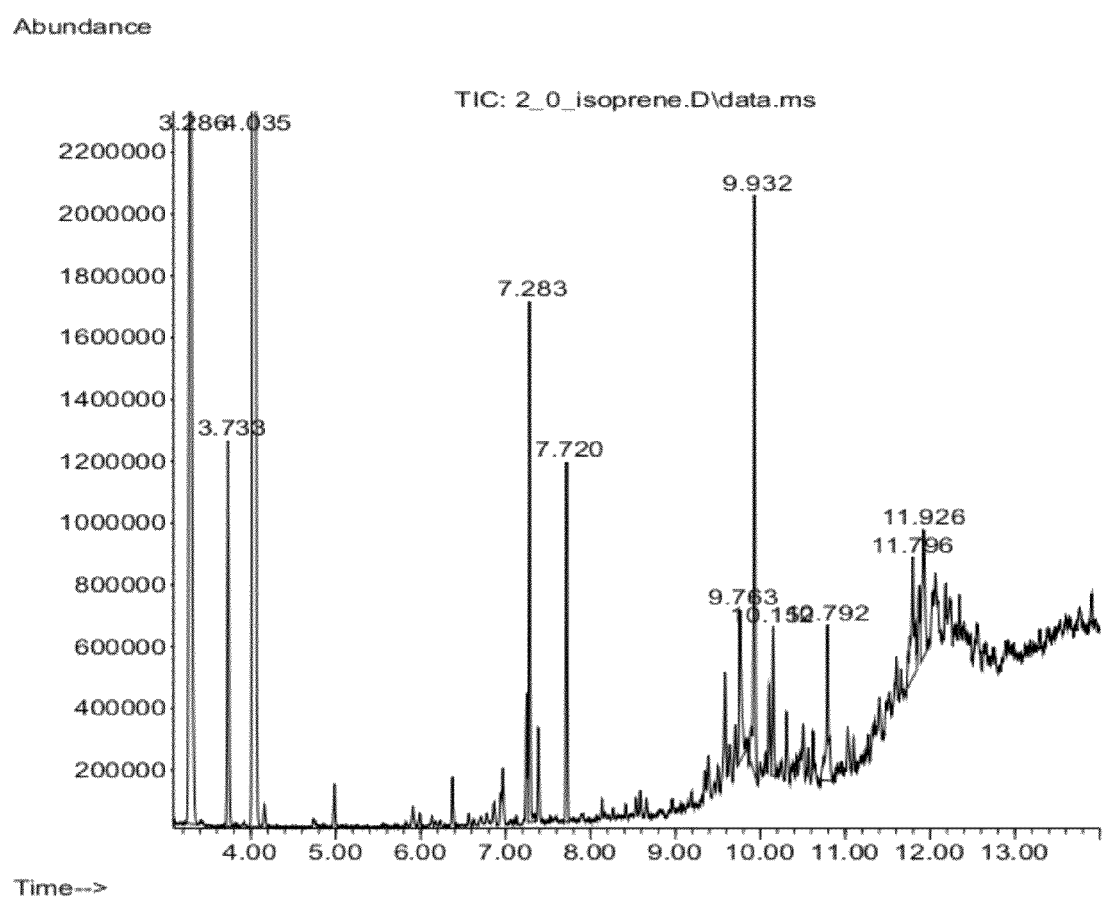
FIG. 15B shows GC/MS chromatograms of products derived from the gas-phase reaction of isoprene (2% v/v) and Amberlyst 15 acid resin. 3-Methyl-3-butanone elutes at 3.734 minutes, isopropyltoluene (cymene) elutes at 7.284 minutes. Isoprene trimers elute at between 9.5 and 10.5 minutes and isoprene tetramers elute between 11.5 and 13 minutes. Peaks at 3.286, 4.035 and 7.720 minutes are contaminants in the DCM injection solvent.
Figure 15C:
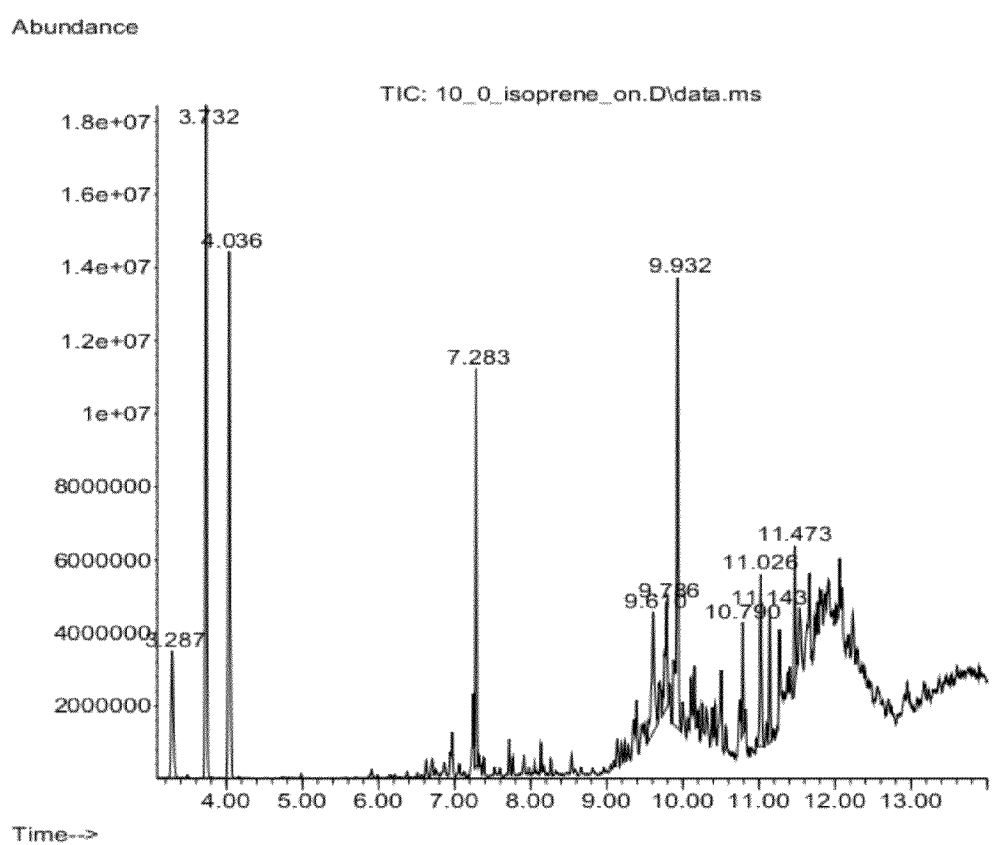
FIG. 15C shows GC/MS chromatograms of products derived from the gas-phase reaction of isoprene (10% v/v) and Amberlyst 15 acid resin. 3-Methyl-3-butanone elutes at 3.732 minutes, isopropyltoluene (cymene) elutes at 7.283 minutes. Isoprene trimers elute at between 9 and 11 minutes and isoprene tetramers elute between 11 and 13 minutes. Peaks at 3.286 and 4.035 minutes are contaminants in the DCM injection solvent.

(B)
The experiment described above was repeated starting using both 2 µL of isoprene (2% v/v) and 10 µL of isoprene (10% v/v). The results are depicted in FIGS. 15B and 15C, respectively. In both cases a range of products was observed including 3-methyl-2-butanone (retention time=3.733 minutes), aromatic C10 compounds (RT 7.283 min), C15 trimers (RT 9 to 11 minutes) and C20 tetramers (11 to 13 minutes).

(C)
The experiment using 10 µL of isoprene (see B) above was repeated, except that the reaction was quenched after 20 minutes by the addition of 500 µL of DCM. Analysis of the DCM extract was conducted using GC/MS method B. A comparison of the results from experiments B and C is shown below in FIG. 16.

Example 6

Figure 17:
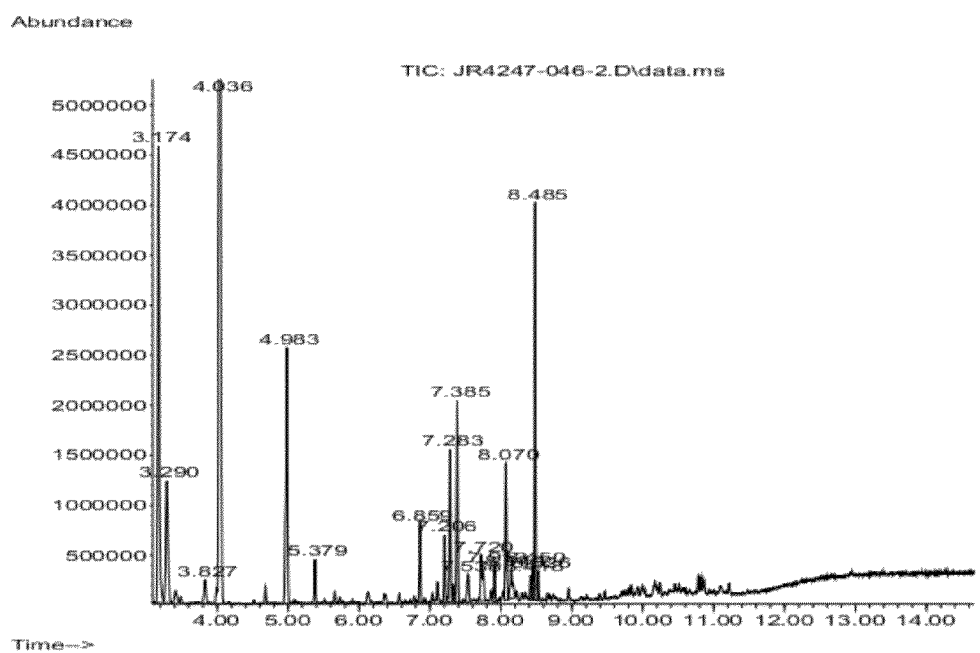
FIG. 17 shows GC/MS chromatogram of the products derived from treatment of bioisoprene vapor with 10% phosphoric acid on silica. The dominant products were 2-methyl-3-buten-2-ol (RT 3.174 minutes) and C10 monooxygenates (RT 6.8-8.5 minutes). Some trimer derivatives are present (9.5-11.5 minutes). No detectable tetramers were observed.

Gas-Phase Conversion of Isoprene to Oxygenated Derivatives (A) Synthesis of 10% Phosphoric Acid on Silica Catalyst
To silica gel (100 g—high-purity grade, pore size 60 Å, 200-400 mesh) was added 85% phosphoric acid (10 mL) with mixing for 3 hours (Note: the initially formed clumps were manually dispersed to allow efficient mixing).
(B) Treatment of Isoprene Vapor with 10% Phosphoric Acid on Silica Catalyst
The phosphoric acid treated silica gel (100 mg) was taken up in a 20 ml headspace vial along with isoprene monomer (10 µL) derived from a bioisoprene composition and sealed. The resulting heterogenous mixture was allowed to sit at 25° C. for approximately 12 hours to produce a light yellow solid. The silica gel was extracted with dichloromethane (DCM) (3 mL) and further analyzed by GC/MS using method B. The results are depicted in FIG. 17.

Example 7

Gas-Phase Conversion of Fermentation Off-Gas Containing Bioisoprene (A) Treatment of Fermentation Off-Gas Containing Bioisoprene with Amberlyst 15 Acid Resin
A fermentation off-gas stream containing bioisoprene was generated by fermentation of a strain of *E. coli* BL21 engineered to produce isoprene from glucose (see, e.g., WO 2009/076676 and WO 2010/003007). The concentration of bioisoprene in the fermentation off-gas was approximately 0.02% v/v for the duration of the experiment. The fermentation off-gas stream containing bioisoprene was passed through a 20 mL headspace vial containing Amberlyst 15 acid resin (100 mg) for 30 minutes. An aliquot of dichloromethane (500 µL) was then added to the vial to extract the silica gel catalyst. The DCM layer was removed and analyzed by GC/MS using method B. The results are depicted in FIG. 18 and indicated the conversion of a portion of the isoprene to 2-methyl-3-buten-2-ol (RT-3.174 minutes).
(B) Treatment of Fermentation Off-Gas Containing Bioisoprene with 10% $H_3PO_4$ on Silica.
The fermentation off-gas stream containing bioisoprene described above was passed through a 20 mL headspace vial containing 10% phosphoric acid on silica (100 mg) for 30 minutes. An aliquot of dichloromethane (500 µL) was then added to the vial to extract the silica gel catalyst. The DCM layer was removed and analyzed by GC/MS using method B. The results are depicted in FIG. 19 and indicated the conversion of a portion of the isoprene to C5 and C10 oxygenated derivatives.

The headings provided herein are not limitations of the various aspects or embodiments of the invention which can be had by reference to the specification as a whole.

All publications, patent applications, and patents cited in this specification are herein incorporated by reference as if each individual publication, patent application, or patent were specifically and individually indicated to be incorporated by reference. In particular, all publications cited herein are expressly incorporated herein by reference for the purpose of describing and disclosing compositions and methodologies which might be used in connection with the invention. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method for producing a fuel constituent from a bioisoprene composition comprising chemically transforming a substantial portion of the isoprene in the bioisoprene composition to one or more non-isoprene compounds by:
   (a) contacting the bioisoprene composition with a catalyst for olefin metathesis to produce one or more olefin products and then catalytically hydrogenating the one or more olefin products to form one or more alkane fuel constituents;
   (b) partially hydrogenating the bioisoprene composition to produce an isoamylene and then alkylating the isoamylene with an isoparaffin to form a high octane alkylate fuel constituent; or
   (c) partially hydrogenating the bioisoprene composition to produce one or more isoamylenes, then contacting the one or more isoamylenes with a catalyst for olefin metathesis to form one or more olefin products, and then catalytically hydrogenating the one or more olefin products to form one or more alkane fuel constituents.

2. The method of claim 1 wherein at least about 95% of isoprene in the bioisoprene composition is converted to non-isoprene compounds.

3. The method of claim 1 wherein the bioisoprene composition comprises or contains greater than about 2 mg of isoprene and comprises or contains greater than or about 99.94% isoprene by weight compared to the total weight of all C5 hydrocarbons in the composition.

4. The method of claim 1 wherein the olefin metathesis catalyst comprises or involves, at least, a metal complex.

5. The method of claim 4 wherein the metal complex is a rhenium complex, a ruthenium complex, a rhodium complex, an osmium complex, a tungsten complex, a molybdenum complex or a titanium complex.

6. The method of claim 1 wherein the olefin product comprises a higher (>C5) olefin or a lower (<C5) olefin or both.

7. The method of claim 6 wherein the one or more olefin products from isoprene metathesis comprise one or more olefins selected from the group consisting of ethylene, isobutylene and olefins containing 6, 8 and 12 carbon atoms (e.g., dimethylhexatrienes).

8. The method of claim 1 wherein the step of partially hydrogenating the bioisoprene composition comprises contacting the bioisoprene composition with hydrogen gas and a catalyst for catalyzing partial hydrogenation of isoprene.

9. The method of claim 8 wherein the catalyst for catalyzing partial hydrogenation of isoprene comprises a palladium catalyst.

10. The method of claim 1 wherein the step of alkylating the isoamylene with an isoparaffin comprises contacting the isoamylene with the isoparaffin in the presence of an acid catalyst.

11. The method of claim 10 wherein the acid catalyst is hydrofluoric acid, sulfuric acid, fluorosulfonic acid or perhaloalkylsulfonic acid.

12. The method of claim 10 wherein the isoparaffin is propane, isobutane or isopentane.

13. The method of claim 1 wherein the olefin metathesis catalyst for isoamylene metathesis is different from the olefin metathesis catalyst for bioisoprene metathesis.

14. The method of claim 1 wherein the olefin metathesis catalyst for isoamylene metathesis is the same as the olefin metathesis catalyst for bioisoprene metathesis.

15. The method of claim 1 wherein the olefin product from isoamylene metathesis comprises one or more olefins selected from the group consisting of ethylene and olefins containing 6, 8 and 12 carbon atoms (e.g., dimethylhexenes).

16. A method for producing a fuel constituent from a bioisoprene composition comprising:
   (a) contacting a bioisoprene composition with an acid catalyst to produce one or more mixed olefin products of C5-C50 olefins wherein the mixed olefin products comprise higher molecular weight olefin products of C16-C50 olefins and lower molecular weight olefin products of C5-C15 olefins;
   (b) converting the higher molecular weight olefin products of C16-C50 olefins to lower molecular weight olefin products of C5-C15 olefins; and
   (c) hydrogenating the lower molecular weight olefin products of C5-C15 olefins to produce saturated hydrocarbon of C5-C15 alkanes fuel constituents; wherein a substantial portion of the isoprene in the bioisoprene composition is chemically converted to one or more non-isoprene compounds.

17. The method of claim 16 wherein the step of converting the higher molecular weight olefin products of C16-C50 olefins to lower molecular weight olefin products of C5-C15 olefins comprises thermal cracking, steam cracking or metathesis.

* * * * *